(12) United States Patent
Demarais et al.

(10) Patent No.: US 7,937,143 B2
(45) Date of Patent: May 3, 2011

(54) METHODS AND APPARATUS FOR INDUCING CONTROLLED RENAL NEUROMODULATION

(75) Inventors: Denise Demarais, Los Gatos, CA (US); Nicolas Zadno, Fremont, CA (US)

(73) Assignee: Ardian, Inc., Mountain View, CA (US)

( * ) Notice: Subject to any disclaimer, the term of this patent is extended or adjusted under 35 U.S.C. 154(b) by 1525 days.

(21) Appl. No.: 11/252,462

(22) Filed: Oct. 18, 2005

(65) Prior Publication Data
US 2007/0066957 A1 Mar. 22, 2007

Related U.S. Application Data

(63) Continuation of application No. 11/233,814, filed on Sep. 23, 2005, now abandoned.

(60) Provisional application No. 60/718,686, filed on Sep. 20, 2005, provisional application No. 60/624,793, filed on Nov. 2, 2004.

(51) Int. Cl.
*A61N 1/30* (2006.01)
(52) U.S. Cl. ............... 604/21; 604/501; 607/44
(58) Field of Classification Search .......... 604/501, 604/20, 21; 607/2, 44
See application file for complete search history.

(56) References Cited

U.S. PATENT DOCUMENTS

| | | |
|---|---|---|
| 2,130,758 A | 9/1938 | Rose |
| 2,276,995 A | 3/1942 | Milinowski |
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens |

(Continued)

FOREIGN PATENT DOCUMENTS

DE 3151180 A1 8/1982

(Continued)

OTHER PUBLICATIONS

U.S. Appl. 60/236,420, Harrison et al.

(Continued)

*Primary Examiner* — Nicholas D Lucchesi
*Assistant Examiner* — Laura A Bouchelle
(74) *Attorney, Agent, or Firm* — Perkins Coie LLP

(57) ABSTRACT

Methods and apparatus are provided for inducing, monitoring and controlling renal neuromodulation using a pulsed electric field to effectuate electroporation or electrofusion. In some embodiments, tissue impedance, conductance or conductivity may be monitored to determine the effects of pulsed electric field therapy, e.g., to determine an extent of electroporation and its degree of irreversibility. Pulsed electric field electroporation of tissue causes a decrease in tissue impedance and an increase in tissue conductivity. If induced electroporation is reversible, upon cessation of the pulsed electric field, tissue impedance and conductivity should approximate baseline levels; however, if electroporation is irreversible, impedance and conductivity changes should persist. Thus, monitoring of impedance or conductivity may be utilized to determine the onset of electroporation and to determine the type or extent of electroporation. Furthermore, monitoring data may be used in one or more manual or automatic feedback loops to control the electroporation.

30 Claims, 15 Drawing Sheets

U.S. PATENT DOCUMENTS

| | | |
|---|---|---|
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,608,985 A | 9/1986 | Crish et al. |
| 4,649,936 A | 3/1987 | Ungar et al. |
| 4,671,286 A | 6/1987 | Renault |
| 4,674,482 A | 6/1987 | Waltonen et al. |
| 4,692,147 A | 9/1987 | Duggan |
| 4,715,852 A | 12/1987 | Reinicke et al. |
| 4,774,967 A | 10/1988 | Zanakis |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,057,318 A | 10/1991 | Magruder et al. |
| 5,058,584 A | 10/1991 | Bourgeois |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,304,120 A | 4/1994 | Crandell et al. |
| 5,304,206 A | 4/1994 | Baker |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,358,514 A | 10/1994 | Schulman et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,472,406 A | 12/1995 | de la Torre et al. |
| 5,478,303 A | 12/1995 | Foley-Nolan et al. |
| 5,494,822 A | 2/1996 | Sadri |
| 5,498,238 A | 3/1996 | Shapland et al. |
| 5,499,971 A | 3/1996 | Shapland et al. |
| 5,507,724 A | 4/1996 | Hofmann et al. |
| 5,507,791 A | 4/1996 | Sit'ko |
| 5,531,778 A | 7/1996 | Maschino et al. |
| 5,540,730 A | 7/1996 | Terry, Jr. et al. |
| 5,540,734 A | 7/1996 | Zabara |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens |
| 5,584,863 A | 12/1996 | Rauch et al. |
| 5,589,192 A | 12/1996 | Okabe et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,792,187 A | 8/1998 | Adams |
| 5,800,464 A | 9/1998 | Kieval |
| 5,807,306 A | 9/1998 | Shapland et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,861,021 A | 1/1999 | Thome et al. |
| 5,865,787 A | 2/1999 | Shapland et al. |
| 5,871,449 A | 2/1999 | Brown |
| 5,891,181 A | 4/1999 | Zhu |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,924,997 A | 7/1999 | Campbell |
| 5,928,272 A | 7/1999 | Adkins et al. |
| 5,935,075 A | 8/1999 | Casscells et al. |
| 5,944,710 A | 8/1999 | Dev et al. |
| 5,983,131 A | 11/1999 | Weaver et al. |
| 5,983,141 A | 11/1999 | Sluijter et al. |
| 6,006,134 A | 12/1999 | Hill et al. |

| | | | | | | |
|---|---|---|---|---|---|---|
| 6,010,613 | A | 1/2000 | Walters et al. | 6,669,655 B1 | 12/2003 | Acker et al. |
| 6,026,326 | A | 2/2000 | Bardy | 6,671,556 B2 | 12/2003 | Osorio et al. |
| 6,051,017 | A | 4/2000 | Loeb et al. | 6,672,312 B2 | 1/2004 | Acker |
| 6,058,328 | A | 5/2000 | Levine et al. | 6,676,657 B2 | 1/2004 | Wood |
| 6,058,331 | A | 5/2000 | King | 6,681,136 B2 | 1/2004 | Schuler et al. |
| 6,073,048 | A | 6/2000 | Kieval et al. | 6,684,105 B2 | 1/2004 | Cohen et al. |
| 6,077,227 | A | 6/2000 | Miesel et al. | 6,690,971 B2 | 2/2004 | Schauerte et al. |
| 6,086,527 | A | 7/2000 | Talpade | 6,692,738 B2 | 2/2004 | MacLaughlin et al. |
| 6,122,548 | A | 9/2000 | Starkebaum et al. | 6,697,670 B2 | 2/2004 | Chomenky et al. |
| 6,123,718 | A | 9/2000 | Tu et al. | 6,718,208 B2 | 4/2004 | Hill et al. |
| 6,146,380 | A | 11/2000 | Racz et al. | 6,735,471 B2 | 5/2004 | Hill et al. |
| 6,161,048 | A | 12/2000 | Sluijter et al. | 6,738,663 B2 | 5/2004 | Schroeppel et al. |
| 6,178,349 | B1 | 1/2001 | Kieval | 6,749,598 B1 | 6/2004 | Keren et al. |
| 6,192,889 | B1 | 2/2001 | Morrish | 6,786,904 B2 | 9/2004 | Doscher et al. |
| 6,205,361 | B1 | 3/2001 | Kuzma et al. | 6,795,728 B2 | 9/2004 | Chornenky et al. |
| 6,208,894 | B1 | 3/2001 | Schulman et al. | 6,845,267 B2 | 1/2005 | Harrison et al. |
| 6,214,032 | B1 | 4/2001 | Loeb et al. | 6,850,801 B2 | 2/2005 | Kieval et al. |
| 6,219,577 | B1 | 4/2001 | Brown, III et al. | 6,865,416 B2 | 3/2005 | Dev et al. |
| 6,238,702 | B1 | 5/2001 | Berde et al. | 6,885,888 B2 | 4/2005 | Rezai |
| 6,245,026 | B1 | 6/2001 | Campbell et al. | 6,916,656 B2 | 7/2005 | Walters et al. |
| 6,246,912 | B1 | 6/2001 | Sluijter | 6,927,049 B2 | 8/2005 | Rubinsky et al. |
| 6,251,130 | B1 | 6/2001 | Dobak, III et al. | 6,939,345 B2 | 9/2005 | KenKnight et al. |
| 6,258,087 | B1 | 7/2001 | Edwards et al. | 6,958,060 B2 | 10/2005 | Mathiesen et al. |
| 6,259,952 | B1 | 7/2001 | Sluijter et al. | 6,972,013 B1 | 12/2005 | Zhang et al. |
| 6,269,269 | B1 | 7/2001 | Ottenhoff et al. | 6,978,174 B2 | 12/2005 | Gelfand et al. |
| 6,272,377 | B1 | 8/2001 | Sweeney et al. | 6,985,774 B2 | 1/2006 | Kieval et al. |
| 6,272,383 | B1 | 8/2001 | Grey et al. | 6,994,700 B2 | 2/2006 | Elkins et al. |
| 6,280,377 | B1 | 8/2001 | Talpade | 6,994,706 B2 | 2/2006 | Chornenky et al. |
| 6,287,304 | B1 | 9/2001 | Eggers et al. | 7,054,685 B2 | 5/2006 | Dimmer et al. |
| 6,287,608 | B1 | 9/2001 | Levin et al. | 7,063,679 B2 | 6/2006 | Maguire et al. |
| 6,292,695 | B1 | 9/2001 | Webster, Jr. et al. | 7,081,114 B2 | 7/2006 | Rashidi |
| 6,304,777 | B1 | 10/2001 | Ben-Haim et al. | 7,081,115 B2 | 7/2006 | Taimisto |
| 6,304,787 | B1 | 10/2001 | Kuzma et al. | 7,083,614 B2 | 8/2006 | Fjield et al. |
| 6,306,423 | B1 | 10/2001 | Donovan et al. | 7,122,019 B1 | 10/2006 | Kesten et al. |
| 6,326,020 | B1 | 12/2001 | Kohane et al. | 2001/0044596 A1 | 11/2001 | Jaafar |
| 6,326,177 | B1 | 12/2001 | Schoenbach et al. | 2002/0026222 A1 | 2/2002 | Schauerte et al. |
| 6,334,069 | B1 | 12/2001 | George et al. | 2002/0026228 A1 | 2/2002 | Schauerte |
| 6,347,247 | B1 | 2/2002 | Dev et al. | 2002/0032468 A1 | 3/2002 | Hill et al. |
| 6,353,763 | B1 | 3/2002 | George et al. | 2002/0038137 A1 | 3/2002 | Stein |
| 6,356,786 | B1 | 3/2002 | Rezai et al. | 2002/0040204 A1 | 4/2002 | Dev et al. |
| 6,356,787 | B1 | 3/2002 | Rezai et al. | 2002/0045853 A1 | 4/2002 | Dev et al. |
| 6,366,808 | B1 | 4/2002 | Schroeppel et al. | 2002/0072782 A1 | 6/2002 | Osorio et al. |
| 6,366,815 | B1 | 4/2002 | Haugland et al. | 2002/0107553 A1 | 8/2002 | Hill et al. |
| 6,393,324 | B2 | 5/2002 | Gruzdowich et al. | 2002/0116030 A1 | 8/2002 | Rezai |
| 6,400,982 | B2 | 6/2002 | Sweeney et al. | 2002/0120304 A1 | 8/2002 | Mest |
| 6,405,079 | B1 | 6/2002 | Ansarinia | 2002/0165586 A1 | 11/2002 | Hill et al. |
| 6,405,732 | B1 | 6/2002 | Edwards et al. | 2002/0169413 A1 | 11/2002 | Keren et al. |
| 6,415,183 | B1 | 7/2002 | Scheiner et al. | 2002/0177846 A1 | 11/2002 | Mulier et al. |
| 6,415,187 | B1 | 7/2002 | Kuzma et al. | 2002/0183684 A1 | 12/2002 | Dev et al. |
| 6,438,423 | B1 | 8/2002 | Rezai et al. | 2002/0188325 A1 | 12/2002 | Hill et al. |
| 6,442,424 | B1 | 8/2002 | Ben-Haim et al. | 2002/0198512 A1 | 12/2002 | Seward |
| 6,449,507 | B1 | 9/2002 | Hill et al. | 2003/0004549 A1 | 1/2003 | Hill et al. |
| 6,450,942 | B1 | 9/2002 | Lapanashvili et al. | 2003/0009145 A1 | 1/2003 | Struijker-Boudier et al. |
| 6,461,314 | B1 | 10/2002 | Pant et al. | 2003/0040774 A1 | 2/2003 | Terry et al. |
| 6,464,687 | B1 | 10/2002 | Ishikawa et al. | 2003/0045909 A1 | 3/2003 | Gross et al. |
| 6,473,644 | B1 | 10/2002 | Terry, Jr. et al. | 2003/0060848 A1 | 3/2003 | Kieval et al. |
| 6,482,619 | B1 | 11/2002 | Rubinsky et al. | 2003/0060857 A1 | 3/2003 | Perrson et al. |
| 6,508,774 | B1 | 1/2003 | Acker et al. | 2003/0060858 A1 | 3/2003 | Kieval et al. |
| 6,514,226 | B1 | 2/2003 | Levin et al. | 2003/0100924 A1 | 5/2003 | Foreman et al. |
| 6,516,211 | B1 | 2/2003 | Acker et al. | 2003/0120270 A1 | 6/2003 | Acker |
| 6,522,926 | B1 | 2/2003 | Kieval et al. | 2003/0150464 A1 | 8/2003 | Casscells |
| 6,522,932 | B1 | 2/2003 | Kuzma et al. | 2003/0199747 A1 | 10/2003 | Michlitsch et al. |
| 6,524,607 | B1 | 2/2003 | Goldenheim et al. | 2003/0199767 A1 | 10/2003 | Cespedes et al. |
| 6,534,081 | B2 | 3/2003 | Goldenheim et al. | 2003/0199768 A1 | 10/2003 | Cespedes et al. |
| 6,536,949 | B1 | 3/2003 | Heuser | 2003/0199806 A1 | 10/2003 | Kieval |
| 6,564,096 | B2 | 5/2003 | Mest | 2003/0204161 A1 | 10/2003 | Ferek-Petric |
| 6,571,127 | B1 | 5/2003 | Ben-Haim et al. | 2003/0216792 A1 | 11/2003 | Levin et al. |
| 6,592,567 | B1 | 7/2003 | Levin et al. | 2003/0220521 A1 | 11/2003 | Reitz et al. |
| 6,599,256 | B1 | 7/2003 | Acker et al. | 2003/0236443 A1 | 12/2003 | Cespedes et al. |
| 6,600,954 | B2 | 7/2003 | Cohen et al. | 2004/0010303 A1 | 1/2004 | Bolea et al. |
| 6,600,956 | B2 | 7/2003 | Maschino et al. | 2004/0019364 A1* | 1/2004 | Kieval et al. .................. 607/9 |
| 6,601,459 | B1 | 8/2003 | Jenni et al. | 2004/0019371 A1 | 1/2004 | Jaafar et al. |
| 6,605,084 | B2 | 8/2003 | Acker et al. | 2004/0064090 A1 | 4/2004 | Keren et al. |
| 6,615,071 | B1 | 9/2003 | Casscells, III et al. | 2004/0064091 A1 | 4/2004 | Keren et al. |
| 6,616,624 | B1 | 9/2003 | Kieval | 2004/0065615 A1 | 4/2004 | Hooper et al. |
| 6,620,151 | B2 | 9/2003 | Blischak et al. | 2004/0073238 A1 | 4/2004 | Makower |
| 6,622,041 | B2 | 9/2003 | Terry, Jr. et al. | 2004/0082978 A1 | 4/2004 | Harrison et al. |
| 6,635,054 | B2 | 10/2003 | Fjield et al. | 2004/0101523 A1 | 5/2004 | Reitz et al. |
| 6,666,845 | B2 | 12/2003 | Hooper et al. | 2004/0106953 A1 | 6/2004 | Yomtov et al. |

| | | | |
|---|---|---|---|
| 2004/0111080 A1 | 6/2004 | Harper et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0220511 A1 | 11/2004 | Scott et al. |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2005/0288730 A1 | 12/2005 | Deem et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0089674 A1 | 4/2006 | Walters et al. |
| 2006/0100667 A1 | 5/2006 | Machado et al. |
| 2006/0111754 A1 | 5/2006 | Rezai et al. |
| 2006/0116720 A1 | 6/2006 | Knoblich |
| 2006/0135998 A1 | 6/2006 | Libbus et al. |
| 2006/0136004 A1 | 6/2006 | Cowan et al. |
| 2006/0155344 A1 | 7/2006 | Rezai et al. |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265014 A1 | 11/2006 | Demarais et al. |
| 2006/0265015 A1 | 11/2006 | Demarais et al. |

FOREIGN PATENT DOCUMENTS

| | | |
|---|---|---|
| EP | 0811395 A2 | 6/1997 |
| WO | WO-85/01213 | 3/1985 |
| WO | WO-91/04725 | 4/1991 |
| WO | WO-93/02740 | 2/1993 |
| WO | WO-93/07803 | 4/1993 |
| WO | WO-94/00188 | 1/1994 |
| WO | WO-96/04957 | 1/1995 |
| WO | WO-95/33514 | 12/1995 |
| WO | WO-96/11723 | 4/1996 |
| WO | WO-97/13550 | 4/1997 |
| WO | WO-97/49453 | 12/1997 |
| WO | WO-98/37926 | 9/1998 |
| WO | WO-98/43700 | 10/1998 |
| WO | WO-98/43701 | 10/1998 |
| WO | WO-98/48888 | 11/1998 |
| WO | WO-99/33407 | 7/1999 |
| WO | W-99/51286 | 10/1999 |
| WO | WO-99/52424 | 10/1999 |
| WO | WO-01/26729 | 4/2001 |
| WO | WO-02/09808 | 2/2002 |
| WO | WO-02/26314 | 4/2002 |
| WO | WO-02/053207 | 7/2002 |
| WO | WO-02/070039 A2 | 9/2002 |
| WO | WO-02/070047 | 9/2002 |
| WO | WO-02/085448 | 10/2002 |
| WO | WO-03/018108 | 3/2003 |
| WO | WO-03/028802 | 4/2003 |
| WO | WO-03/063692 | 8/2003 |
| WO | WO-03/071140 A2 | 8/2003 |
| WO | WO-03/076008 | 9/2003 |
| WO | WO-03/082080 | 10/2003 |
| WO | WO-03/082403 | 10/2003 |
| WO | WO-2004/026370 | 4/2004 |
| WO | WO-2004/026371 | 4/2004 |
| WO | WO-2004/026374 | 4/2004 |
| WO | WO-2004/030718 | 4/2004 |
| WO | WO-2004/032791 | 4/2004 |
| WO | WO-2004/107965 | 12/2004 |
| WO | WO-2005014100 | 2/2005 |
| WO | WO-2005016165 | 2/2005 |
| WO | WO-2005/032646 A2 | 4/2005 |
| WO | WO-2005/065284 | 7/2005 |
| WO | WO-2005/084389 A2 | 9/2005 |
| WO | WO-2005/097256 A2 | 10/2005 |
| WO | WO-2005/123183 | 12/2005 |
| WO | WO-2006/007048 A2 | 1/2006 |
| WO | WO-2006018528 A1 | 2/2006 |
| WO | WO-2006/031899 A2 | 3/2006 |

OTHER PUBLICATIONS

"Atrial Fibrillation" Heart and Vascular Health on Yahoo! Health. 2 pages. <URL: http://health.yahoo.com/topic/heart/overview/article/healthwise/hw160872;_yit=AiBT43Ey74HQ 7ft3jAb4C.sPu7cF>.

"Heart Arrhythmia" Heart and Vascular Health on Yahoo! Health. 13 pages. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF>.

"Isovue: Data Sheet". Regional Health Limited. 8 pages. Mar. 11, 2003.

"Micro ETS Hyperhidrosis USA" Hyperhidrosis USA. 2 pages. <URL: http://www.hyperhidrosis-usa.com/Index.html>.

Amersham Health. "Hypaque-Cysto" 6 pages. 2003.

Arentz, Thomas et al. "Incidence of pulmonary vein stenosis 2 years after radiofrequency catheter ablation of refractory atrial fibrillation." European Heart Journal. 2003. 24; pp. 963-969.

Boehmer, John P. "Resynchronization Therapy for Chronic CHF: Indications, Devices and Outcomes". Penn State College of Medicine: Penn State Heart and Vascular Institute. Transcatheter Cardiovascular Therapeutics 2005. 31 slides.

Bourge, Robert C. "Heart Failure Monitoring Devices: Rationale and Status" 28 pages.

Burkhoff, Daniel. "Interventional Device-Based Therapy for CHF Will Redefine Current Treatment Paradigms". Columbia University. 2004. 32 slides.

Canbaz, Suat et al. "Electrophysiological evaluation of phrenic nerve injury during cardiac surgery—a prospective, controlled clinical study." BioMed Central. 5 pages. 2004.

Carson, Peter. "Device-based Treatment for Chronic Heart Failure: Electrical Modulation of Myocardial Contractility". Transcatheter Cardiovascular Therapeutics 2005. 21 slides.

Chiou, CW et al. "Efferent Vagal Innervation of the Canine Atria and Sinus and Atrioventricular Nodes". Circulation. Jun. 1997. 95(11):2573-2584. Abstract only. 2 pages.

Cryovascular Systems, Inc. "Pre-Clinical Testing Establishing Parameters". PowerPoint Presentation. 18 slides.

Daniel, Alan and Honig, Carl R. "Does Histamine Influence Vasodilation Caused by Prolonged Arterial Occlusion or Heavy Exercise?" The Journal of Pharmacology and Experimental Therapeutics. vol. 215 No. 2. Aug. 21, 1980. pp. 533-538.

Dong, Jun et al. "Incidence and Predictors of Pulmonary Vein Stenosis Following Catheter Ablation of Atrial Fibrillation Using the Anatomic Pulmonary Vein Ablation Approach: Results from Paired Magnetic Resonance Imaging." Journal of Cardiovascular Electrophysiology. vol. 16, No. 8, Aug. 2005. pp. 845-852.

Fava, M. "Clinical Testing Establishing Safety & Efficacy". PowerPoint Presentation. Cryovascular Systems, Inc. 14 slides.

Fava, M. et al. "Initial Human Experience with CryoPlasty™ in the Treatment of Infrainguinal Arterial Disease." Abstract. 1 page.

Fischell, Tim A. et al. "Ultrasonic Energy: Effects on Vascular Function and integrity." Circulation: Journal of the American Heart Association. 1991, 84;pp. 1783-1795.

Hodgkin, Douglas D. et al. "Electrophysiologic Characteristics of a Pulsed Iontophoretic Drug-Delivery System in Coronary Arteries." Journal of Cardiovascular Pharmacology. 29(1):pp. 39-44, Jan. 1997. Abstract. 2 pages.

Jia, Jianping and Pollock, Martin. "The pathogenesis of non-freezing cold nerve injury: Observations in the rat." Brain. 120; pp. 631-646. 1997.

Jia, Jianping et al. "Cold injury to nerves is not due to ischaemia alone." Brain. 121;pp. 989-1001, 1998.

Jin, Yuanzhe. et al. "Pulmonary Vein Stenosis and Remodeling After Electrical Isolation for Treatment of Atrial Fibrillation: Short- and Medium-Term Follow-Up." PACE, vol. 27. pp. 1362-1370. Oct. 2004.

Joye, James D. and Tatsutani, Kristine. "In Vitro Studies of Arterial Freezing Injury". 4 pages.

Joye, James D. And Tatsutani, Kristine. "In Vivo Study of Endovascular Cryotherapy for the Prevention of Restenosis." 4 pages.

Knot, Harm J. and Nelson, Mark T. "Regulation of arterial diameter and wall [Ca2+] in cerebral arteries of rat by membrane potential and intravascular pressure," The Journal of Physiology. 1998. 508; pp. 199-209.

Kok, Lai Chow et al. "Effect of Heating on Pulmonary Veins: How to Avoid Pulmonary Vein Stenosis." Journal of Cardiovascular Electrophysiology. vol. 14, No, 3, Mar. 2003. pp. 250-254.

Lee, Michael A. (editor). SPORTSMed. Connecticut State Medical Society Committee on the Medical Aspects of Sports. Fall/Winter 2005. 10 pages.

Mathur, Vandana S. "Intra-Renal Drug Delivery for Fluid Overload", FlowMedica, Transcatheter Cardiovascular Therapeutics 2005. 31 slides.

Mehran, Roxana. "Renal insufficiency and contrast nephropathy: The most common, least understood risk factor", Cardiovascular Research Foundation. Columbia University Medical Center. 2005. 86 slides.

Packer, Douglas L. et al. "Clinical Presentation, Investigation, and Management of Pulmonary Vein Stenosis Complicating Ablation for Atrial Fibrillation," Circulation: Journal of the American Heart Association. Feb. 8, 2005. pp. 546-554.

Pappone, Carlo and Santinelli, Vincenzo. "[2005][P2-70] Safety Report of Circumferential Pulmonary Vein Ablation. A 9-Year Single-Center Experience on 6,442 Patients with Atrial Fibrillation," Abstract only. 1 page.

Pappone, Carlo et al. "[2004][759] Pulmonary Vein Denervation Benefits Paroxysmal Atrial Fibrillation Patients after Circumferential Ablation." Abstract only. 1 page.

Purerfellner, Helmut and Martinek, Martin. "Pulmonary vein stenosis following catheter ablation of atrial fibrillation." Current Opinion in Cardiology. 20; pp. 484-490. 2005.

Purerfellner, Helmut et al. "Pulmonary Vein Stenosis by Ostial Irrigated-Tip Ablation: Incidence, Time Course, and Prediction." Journal of Cardiovascular Electrophysiology. vol. 14, No. 2, Feb. 2003. pp. 158-164.

Saad, Eduardo B. et al. "Pulmonary Vein Stenosis After Radiofrequency Ablation of Atrial Fibrillation: Functional Characterization, Evolution, and Influence of the Ablation Strategy." Circulation. 108; pp. 3102-3107. 2003.

Sabbah, Hani N. "Animal Models for Heart Failure and Device Development". Henry Ford Health System. 24 slides.

Schauerte, P. et al. "Catheter ablation of cardiac autonomic nerves for prevention of vagal atrial fibrillation," Circulation. 102(22). Nov. 28, 2000. Abstract only. 2 pages.

Schauerte, P et al. "Focal atrial fibrillation: experimental evidence for a pathophysiologic role of the autonomic nervous system." Journal of Cardiovascular Electrophysiology. 12(5). May 2001. Abstract only. 2 pages.

Schauerte, P. et al. "Transvenous parasympathetic nerve stimulation in the inferior vena cava and atrioventricular conduction." Journal of Cardiovascular Electrophysiology. 11(1). Jan. 2000. Abstract only. 2 pages.

Scherlag, BJ and Po, S. "The intrinsic cardiac nervous system and atrial fibrillation." Current Opinion in Cardiology. 21(1):51-54, Jan. 2006. Abstract only. 2 pages.

Schmitt, Joseph et al. "Intravascular Optical Coherence Tomography—Opening a Window into Coronary Artery Disease". LightLab Imaging, Inc. Business Briefing: European Cardiology 2005.

Siegel, RJ et al. "Clinical demonstration that catheter-delivered ultrasound energy reverses arterial vasoconstriction." Journal of the American College of Cardiology. 1992. 20; 732-735. Summary only. 2 pages.

Sobotka, Paul A. "Treatment Strategies for Fluid Overload, CHF Patients". CHF Solutions. Transcatheter Cardiovascular Therapeutics 2005. 20 slides.

Steffen, W. et al. "Catheter-delivered high intensity, low frequency ultrasound induces vasodilation in vivo." European Heart Journal. 1994. 15;pp. 369-376.

Steg, PG. et al. "Pulsed ultraviolet laser irradiation produces endothelium-independent relaxation of vascular smooth muscle". Circulation: Journal of the American Heart Association. 1989. pp. 189-197.

Taka, Tomomi et al. "Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats". Pathophysiology of Haemostasis and Thrombosis. Dec. 23, 2002. pp. 184-189.

Tamborero, David et al. "Incidence of Pulmonary Vein Stenosis in Patients Submitted to Atrial Fibrillation Ablation: A Comparison of the Selective Segmental Ostial Ablation vs. the Circumferential Pulmonary Veins Ablation," Journal of Intervocational Cardiac Electrophysiology. 14; pp. 41-25, 2005.

Yu, Wen-Chung et al. "Acquired Pulmonary Vein Stenosis after Radiofrequency Catheter Ablation of Paroxysmal Atrial Fibrillation," Journal of Cardiovascular Electrophysiology. vol. 12, No. 8, Aug. 2001, pp. 887-892.

U.S. Appl. No. 11/504,117, Demarais et al.
U.S. Appl. No. 11/599,649, Demarais et al.
U.S. Appl. No. 11/599,723, Demarais et al.
U.S. Appl. No. 11/599,882, Demarais et al.
U.S. Appl. No. 11/599,890, Demarais et al.
U.S. Appl. No. 11/688,178, Levin et al.
U.S. Appl. No. 11/233,814, Denise Demarais.
U.S. Appl. No. 11/266,993, Denise Demarais.
U.S. Appl. No. 11/324,188, Denise Demarais.
U.S. Appl. No. 11/363,867, Denise Demarais.
U.S. Appl. No. 11/368,577, Demarais.
U.S. Appl. No. 11/368,809, Denise Demarais.
U.S. Appl. No. 11/368,949, Denise Memarais.
U.S. Appl. No. 11/368,971, Denise Demarais.

"2003 European Society of Hypertension-European Society of Cardiology guidelines for the management of arterial hypertension," Journal of Hypertension 2003, vol. 21, No. 6, pp. 1011-1053.

"Advanced Neuromodulation Systems' Comparison Chart," 1 page.

"Advances in the role of the sympathetic nervous system in cardiovascular medicine," 2001 SNS Report, No. 3, Springer, published with an educational grant from Servier, pp. 1-8.

"Clinical Trials in Hypertension and Renal Diseases," Slide Source, www.hypertensiononline.org, 33 pages.

"ECM 830 Specifications Sheet," tech@genetronics.com, 20-001796-01 Rev D, 2 pages.

"Electrical Stimulation for the Treatment of Chronic Wounds," Radiation Protection Standard, Maximum Exposure Levels to Radiofrequency Fields—KHz to 300 GHz, Radiation Protection Series No. 3, Australian Radiation Protection and Nuclear Safety Agency, Apr. 1996, 322 pages.

"Electropermeabilization (Electroporation)," Cyto Pulse Sciences Inc., http://www.cytopulse.com/electroporation.html (last accessed Mar. 3, 2005), 3 pages.

"Electroporation based Technologies and Treatments," ESPE Newsletter No. 6, QLK 02002-2003, Jan. 2005, www.cliniporator.com, 4 pages.

"End-stage renal disease payment policies in traditional Medicare," Report to the Congress: Medicare Payment Policy, Mar. 2001, Medpac, pp. 123-138.

"Epidemiology of Renal Disease in Hypertension," slide presentation by hypertensiononline.org, 21 pages.

"Fact Book Fiscal Year 2003," National Institutes of Health National Heart, Lung, and Blood Institute, Feb. 2004, 197 pages.

"Heart Disease and Stroke Statistics-2004 update," American Heart Association, American Stroke Association, Dallas, Texas, © 2003 American Heart Association, 52 pages.

"Hypertension and Renal Disease: Mechanisms," Slide Show by www.hypertensiononline.org, 22 pages.

"Hypertension Incidence and Prevalence, Age Specific Rates, by Gender, B.C., 2001/2002," Graph., Chronic Disease Management, May 2003, British Columbia Ministry of Health Services, 1 page.

"Infumedics Inc.," Background and products paper and comparison of Medtronic SynchroMed II and Infumedics Prometra pumps, 3 pages.

"Introduction to Autonomic Pharmacology," Chapter 3, Part 2 Autonomic Pharmacology, pp. 18-26.

"Market for infusion pumps grows with an aging population," NWL 97-01, The BBI Newsletter, vol. 20, No. 2, Feb. 1, 1997, American Health Consultants Inc., 6 pages.

"PHCL 762 Pharmacology of the Autonomic Nervous System," Chapter 2 and 6.8 in Mosby, http://www.kumc.edu/research/medicine/pharmacology/CAI/phc1762.html, last accessed Aug. 24, 2004, 14 pages.

"Programmable Infusion System," Pumps and Pump Selection, Medtronic Pain Therapies, Medtronic, Inc. Sep. 5, 2001, 2 pages.

"Pulmonary Concepts in Critical Care Breath Sounds," http://rnbob.tripod.com/breath.htm, last accessed Aug. 23, 2004, 5 pages.

"Pulmonary Function Testing," http://jan.ucc.nau.edu/~daa/lecture/pft.htm, last accessed Aug. 23, 2004, 8 pages.

"Sensorcaine-MPF Spinal Injection," informational document, AstraZeneca 2001, 2 pages.

"Summary," Critical Reviews in Biomedical Engineering, vol. 17, Issue 5, 1989, pp. 515-529.

"The Antihypertensive and Lipid-Lowering Treatment to Prevent Heart Attack Trial," ALLHAT Research Group, JAMA 2002, vol. 288, pp. 2981-2997.

Aars, H. and S. Akre, "Reflex Changes in Sympathetic Activity and Arterial Blood Pressure Evoked by Afferent Stimulation of the Renal Nerve," Feb. 26, 1999, Acta Physiol. Scand., vol. 78, 1970, pp. 184-188.

Abramov, G.S. et al., "Alteration in sensory nerve function following electrical shock," Burns vol. 22, No. 8, © 1996 Elsevier Science Ltd., pp. 602-606.

Achar, Suraj, M.D. and Suriti Kundu, M.D., "Principles of Office Anesthesia: Part I. Infiltrative Anesthesia," Office Procedures, American Family Physician, Jul. 1, 2002, vol. 66, No. 1, pp. 91-94.

Agnew, William F. et al., "Evolution and Resolution of Stimulation-Induced Axonal Injury in Peripheral Nerve," May 21, 1999, Muscle and Nerve, vol. 22, Oct. 1999, © 1999 John Wiley & Sons, pp. 1393-1402.

Ahadian, Farshad M., M.D., "Pulsed Radiofrequency Neurotomy: Advances in Pain Medicine," Current Pain and Headache Reports 2004, vol. 8, © 2004 Current Science Inc., pp. 34-40.

Alford, J.Winslow, M.D. and Paul. D. Fadale, M.D., "Evaluation of Postoperative Bupivacaine Infusion for Pain Management After Anterior Cruciate Ligament Reconstruction," The Journal of Arthroscopic and Related Surgery October, vol. 19, No. 8, © 2003 Arthroscopy Association of North America, pp. 855-861.

Andrews, B.T. et al., "The use of surgical sympathectomy in the treatment of chronic renal pain," Mar. 5, 1997, British Journal of Urology, vol. 80, © 1997 British Journal of Urology, pp. 6-10.

Archer, Steffan et al., "Cell Reactions to Dielectrophoretic Manipulation," Mar. 1, 1999, Biochemical and Biophysical Research Commuications, 1999 Academic Press, pp. 687-698.

Arias, Manuel J., M.D., "Percutaneous Radio Frequency Thermocoagulation with Low Temperature in the Treatment of Essential Glossopharyngeal Neuralgia," Surg. Neurol. 1986, vol. 25, © 1986 Elsevier Science Publishing Co. Inc., pp. 94-96.

Aronofsky, David H., D.D.S., "Reduction of dental postsurgical symptoms using nonthermal pulsed high-peak-power electromagnetic energy," Oral Surg., Nov. 1971, vol. 32, No. 5, pp. 688-696.

Aspelin, Peter, M.D., Ph.D. et al, "Nephrotoxic Effects in High-Risk Patients Undergoing Angiography," Feb. 6, 2003, New England Journal of Medicine 2003, vol. 348, No. 6, 2003 Massachusetts Medical Society, pp. 491-499.

Awwad, Ziad M., FRCS and Bashir A. Atiyat, GBA, JBA, "Pain relief using continuous bupivacaine infusion in the paravertebral space after loin incision," May 15, 2004, Saudi Med. J. 2004, vol. 25, No. 10, pp. 1369-1373.

Badyal, D.K., H. Lata and A.P. Dadhich, "Animal Models of Hypertension and Effect of Drugs," Aug. 19, 2003, Indian Journal of Pharmacology 2003, vol. 35, pp. 349-362.

Baker, Carol E. et al., "Effect of pH of Bupivacaine on Duration of Repeated Sciatic Nerve Blocks in the Albino Rat," Anesth. Analg, 1991, vol. 72, © 1991 The International Anesthesia Research Society, pp. 773-778.

Balazs, Tibor, "Development of Tissue Resistance to Toxic Effects of Chemicals," Jan. 26, 1974, Toxicology, vol. 2, © 1974 Elsevier/North Holland, Amsterdam, pp. 247-255.

Barrett, Carolyn J. et al., "Long-term control of renal blood flow: what is the role of renal nerves?" Jan. 4, 2001, Am. J. Physiol. Regulatory Integrative Comp. Physiol. 2001, vol. 280, © 2001 the American Physiological Society, pp. R1534-R1545.

Barrett, Carolyn J. et al., "What Sets the Long-Term Level of Renal Sympathetic Nerve Activity?," May 12, 2003, Integrative Physiology, Circulation Research 2003, vol. 92, © 2003 American Heart Association, pp. 1330-1336.

Bassett, C. Andrew L. et al., "Augmentation of Bone Repair by Inductively Coupled Electromagnetic Fields," May 3, 1974, Science, vol. 184, pp. 575-577.

Bassett, C. Andrew L., "Fundamental and Practical Aspects of Therapeutic Uses of Pulsed Electromagnetic Fields (PEMFs)," Critical Reviews in Biomedical Engineering, vol. 17, No. 5, 1989, pp. 451-514.

Beebe, Stephen J. et al., "Nanosecond Pulsed Electric Field (nsPEF) Effects on Cells and Tissues: Apoptosis Induction and Tumor Growth Inhibition," Oct. 11, 2001, IEEE Transactions on Plasma Science, vol. 30, No. 1, Feb. 2002, © 2002 IEEE, pp. 286-292.

Beebe, Stephen J. et al., "Nanosecond pulsed electric fields modulate cell function through intracellular signal transduction mechanisms," Apr. 8, 2004, Physiological Measurement, vol. 25, 2004, © 2004 IOP Publishing Ltd., pp. 1077-1093.

Bhadra, Niloy and Kevin L. Kilgore, "Direct Current Electrical Conduction Block of Peripheral Nerve," Feb. 25, 2004, IEEE Transactions on Neural Systems and Rehabilitation Engineering, vol. 12, No. 3, Sep. 2004, pp. 313-324.

Bhatt, Deepak L. et al., "Rhabdomyolysis Due to Pulsed Electric Fields," May 11, 1989, Plastic and Reconstructive Surgery Jul. 1990, pp. 1-11.

Bigler, D. et al., "Tachyphylaxis during postoperative epidural analgesia-new insights," Apr. 15, 1987, Letter to the Editor, Acta Anesthesiol. Scand. 1987, vol. 31, pp. 664-665.

Binder, Allan et al., "Pulsed Electromagnetic Field Therapy of Persistent Rotator Cuff Tendinitis," The Lancet, Saturday Mar. 31, 1984, the Lancet Ltd., pp. 695-698.

Black, Henry R., M.D., "Resistant Hypertension 2004," presentation at Rush University Medical Center, Jul. 15, 2004, 40 pages.

Blair, M.L. et al., "Sympathetic activation cannot fully account for increased plasma renin levels during water deprivation," Sep. 23, 1996, Am J Physiol 1997, vol. 272, © 1997 the American Physiological Society, pp. R1197-R1203.

Blomberg, Sture G., M.D., Ph.D., "Long-Term Home Self-Treatment with High Thoracic Epidural Anesthesia in Patients with Severe Coronary Artery Disease," Mar. 29, 1994, Anesth. Analg. 1994, vol. 79, © 1994 International Anesthesia Research Society, pp. 413-421.

Cahana, Alex, M.D., "Pulsed Radiofrequency: A Neurobiologic and Clinical Reality," May 17, 2005, Anesthesiology 2005, vol. 103, No. 6, Dec. 2005, © 2005 American Society of Anesthesiologists, Inc., Lippincott Williams & Wilkins, Inc., p. 1311.

Calaresu, F.R. et al., "Haemodynamic Responses and Renin Release During Stimulation of Afferent Renal Nerves in the Cat," Aug. 12, 1975, J. Physiol. 1976, vol. 255, pp. 687-700.

Campese, V.M., "A new model of neurogenic hypertension caused by renal injury: pathophysiology and therapeutic implications," Clin. Exp. Nephrol 2003, vol. 7, © 2003 Japanese Society of Nephroloogy, pp. 167-171.

Campese, V.M., "Neurogenic factors and hypertension in chronic renal failure," Journal of Nephrology, vol. 10, No. 4, © 1997 Societa Italiana di Nefrologia, pp. 184-187.

Carls, G., et al., "Electrical and magnetic stimulation of the intercostal nerves: a comparative study," Electromyogr. clin. Neurophysiol., vol. 37, 1997, pp. 509-512.

Carlson, Scott H. And J. Michael Wyss, "e-Hyertension, Opening New Vistas," Introductory Commentary, Hypertension 2000, vol. 35, American Heart Association, Inc., 2000, p. 538.

Chang, Donald C., "Cell poration and cell fusion using an oscillating electric field," Biophysical Journal, vol. 56, Oct. 1989, Biophysical Society, pp. 641-652.

Chobanian, Aram V. et al., "Seventh Report of the Joint National Committee on Prevention, Detection, Evaluation, and Treatment of High Blood Pressure," Nov. 6, 2003, Hypertension 2003, vol. 42, © 2003 American Heart Association, Inc., pp. 1206-1252.

Codman 3000, Implantable Constant-Flow Infusion Pump Pamphlet, For Continuous Intrathecal Drug Delivery, 2 pages.

Conradi, E., Ines Helen Pages, "Effects of Continuous and Pulsed Microwave Irradiation on Distribution of Heat in the Gluteal Region of Minipigs," Scand. J. Rehab. Med., vol. 21, 1989, pp. 59-62.

Converse Jr., R.L. et al., "Sympathetic Overactivity in Patients with Chronic Renal Failure," New England Journal of Medicine, Dec. 31, 1992, vol. 327 (27), pp. 1912-1918.

Cosman, Eric R., Jr. et al., "Electric and Thermal Field Effects in Tissue Around Radiofrequency Electrodes," Pain Medicine, vol. 6, No. 6, 2005, American Academy of Pain Medicine, pp. 405-424.

Cosman, Eric R., Ph.D., "A Comment on the History of the Pulsed Radiofrequency Technique for Pain Therapy," Anesthesiology Dec. 2005, vol. 103, No. 6, © 2005 American Society of Anesthesiologists, Inc. Lippincott Williams & Wilkins, Inc., p. 1312.

Crawford, William H. et al., "Pulsed Radio Frequency Therapy of Experimentally Induced Arthritis in Ponies," Dec. 18, 1989, Can. J. Vet. Res. 1991, vol. 55, pp. 76-85.

Dahm, Peter et al., "Efficacy and Technical Complications of Long-Term Continuous Intraspinal Infusions of Opioid and/or Bupivacaine in Refractory Nonmalignant Pain . . . ," Oct. 6, 1997, The Clinical Journal of Pain 1998, vol. 14, No. 1, © 1998 Lippincott-Raven Publishers, pp. 4-16.

Dahm, Peter O. et al., "Long-Term Intrathecal Infusion of Opioid and/or Bupivacaine in the Prophylaxis and Treatment of Phantom Limb Pain," Neuromodulation 1998, vol. 1, No. 3, © 1998 International Neuromodulation Society, pp. 111-128.

Dang, Nicholas C. et al., "A Novel Approach to Increase Total Urine Output in Heart Failure: Renal Nerve Blockade," ACC 2005 poster, 1 page.

Davalos, R.V. et al., "Tissue Ablation with Irreversible Electroporation," Sep. 7, 2004, Annals of Biomedical Engineering, vol. 33, No. 2, © 2005 Biomedical Engineering Society, pp. 223-231.

De Leeuw, Peter W. et al., "Renal Vascular Tachyphylaxis to Angiotensin II: Specificity of the Response for Angiotensin," Dec. 28, 1981, Life Sciences, vol. 30, © 1982 Pergamon Press Ltd., pp. 813-819.

Deng, Jingdong et al., "The Effects of Intense Submicrosecond Electrical Pulses on Cells," Nov. 26, 2002, Biophysical Journal, vol. 84, Apr. 2003, © 2003 Biophysical Society, pp. 2709-2714.

Denton, Kate M. et al., "Differential Neural Control of Glomerular Ultrafiltration," Jan. 30, 2004, Proceedings of the Australian Physiological and Pharmacological Society Symposium: Hormonal, Metabolic and Neural Control of the Kidney, Clinical and Experimental Pharmacology and Physiology (2004), 31, pp. 380-386.

Dev, Nagendu B., Ph.D. et al., "Intravascular Electroporation Markedly Attenuates Neointima Formation After Balloon Injury of the Carotid Artery in the Rat," Journal of Interventional Cardiology, vol. 13, No. 5, 2000, pp. 331-338.

Dev, Nagendu B., Ph.D. et al., "Sustained Local Delivery of Heparin to the Rabbit Arterial Wall With an Electroporation Catheter," May 5, 1998, Catheterization and Cardiovascular Diagnosis 1998, vol. 45, © 1998 Wiley-Liss Inc., pp. 337-345.

Dibona, Gerald F. And Linda L. Sawin, "Role of renal nerves in sodium retention of cirrhosis and congestive heart failure," Sep. 27, 1990, Am J Physiol 1991, vol. 260, © 1991 The American Physiological Society, pp. R298-R305.

Dibona, Gerald F. And Ulla C. Kopp, "Neural Control of Renal Function," Physiological Reviews Jan. 1997, vol. 77, No. 1, © 1997 American Physiological Society, pp. 75-197.

Dibona, Gerald F. And Ulla C. Kopp, "Role of the Renal Sympathetic Nerves in Pathophysiological States," Neural Control of Renal Function, vol. 77, pp. 142-197.

Dibona, Gerald F., "Neural Control of the Kidney-Past, Present, and Future," Nov. 4, 2002, Novartis Lecture, Hypertension 2003, vol. 41, part 2, © 2002 American Heart Association, pp. 621-624.

Dibona, Gerald F., "Peripheral and Central Interactions between the Renin-Angiotensin System and the Renal Sympathetic Nerves in Control of Renal Function," Annals New York Academy of Sciences, pp. 395-406.

Dibona, Gerald F., "Renal Innervation and Denervation: Lessons from Renal Transplantation Reconsidered," Artificial Organs, vol. 11, No. 6, Raven Press Ltd., © 1987 International Society for Artificial Organs, pp. 457-462.

Dibona, Gerald F., "The Sympathetic Nervous System and Hypertension," Dec. 4, 2003, Hypertension Highlights, Hypertension Feb. 2004, vol. 43, © 2004 American Heart Association, pp. 147-150.

Dibona, Gerald F., L.L. Sawin, "Effect of renal denervation on dynamic autoregulation of renal blood flow," Feb. 12, 2004, Am J Physiol Renal Physiol 286, pp. F1209-F1218.

Dibona, Gerald F., Susan Y. Jones, "Dynamic Analysis of Renal Nerve Activity Responses to Baroreceptor Denervation in Hypertensive Rats," Sep. 19, 2000, Hypertension Apr. 2001, © 2001 American Heart Association, pp. 1153-1163.

Dorros, Gerald, M.D., "Renal Artery Stenting State of the Art," presentation, TCT, Washington D.C., Sep. 2003, 27 pages.

Dunn, Matthew D. et al., "Laparoscopic Nephrectomy in Patients With End-Stage Renal Disease and Autosomal Dominant Polycystic Kidney Disease," Oct. 25, 1999, American Journal of Kidney Diseases Apr. 2000, vol. 35, No. 4, © 2000 National Kidney Foundation, Inc., pp. 720-725.

Durand, D.M., "Electrical Field Effects in Hyperexcitable Neural Tissue: A Review," Radiation Protection Dosimetry, vol. 106, No. 4, 2003, Nuclear Technology Publishing, pp. 325-331.

Erdine, Serap and Alev Arat-Ozkan, "Resistant Hypertension," European Society of Hypertension Scientific Newsletter: Update on Hypertension Management, 2003, vol. 4, No. 15, 2 pages.

Fareed, Jawad, Ph.D. et al., "Some Objective Considerations for the Use of Heparins and Recombinant Hirudin in Percutaneous Transluminal Coronary Angioplasty," Seminars in Thrombosis and Hemostasis 1991, vol. 17, No. 4, © 1991 Thieme Medical Publishers, Inc., pp. 455-470.

Ferguson, D.R. et al., "Responses of the pig isolated renal artery to transmural electrical stimulation and drugs," Dec. 7, 1984, Br. J. Pharmac. 1985, vol. 84, © 1985 The Macmillan Press Ltd., pp. 879-882.

Fernandez-Ortiz, Antonio et al., "A New Approach for Local Intravascular Drug Delivery—Iontophoretic Balloon,," Intravascular Iontophoretic Local Delivery, Circulation, vol. 89, No. 4, Apr. 1994, pp. 1518-1522.

Fields, Larry E. et al, "The Burden of Adult Hypertension in the United States 1999 to 2000—A Rising Tide," May 18, 2004, © 2004 The American Heart Association, Hypertension Oct. 2004, pp. 1-7.

Freeman, Scott A. et al., "Theory of Electroporation of Planar Bilayer Membranes: Predictions of the Aqueous Area, Change in Capacitance, and Pore-Pore Separation," Feb. 23, 1994, Biophysical Journal, Jul. 1994, vol. 67, © 1994 by the Biophysical Society, pp. 42-56.

Fukuoka, Yuko et al., "Imaging of neural conduction block by neuromagnetic recording," Oct. 16, 2002, Clinical Neurophysiology 2002, vol. 113, © 2002 Elsevier Science Ireland Ltd., pp. 1985-1992.

Gami, Apoor S., M.D. And Vesna D. Garovic, M.D., "Contrast Nephropathy After Coronary Angiography," Mayo Clin Proc. 2004, vol. 79, 2004 Mayo Foundation for Medical Education and Research, pp. 211-219.

Gattone II, Vincent H. et al., "Contribution of Renal Innervation to Hypertension in Polycystic Kidney Disease in the Rat," University of Chicago Section of Urology, 16 pages.

Gaylor, D.C. et al., "Significance of Cell Size and Tissue Structure in Electrical Trauma," Jan. 26, 1998, J. Theor. Biol. 1988, vol. 133, © 1988 Academic Press Limited, pp. 223-237.

Ghoname, El-sayed A. et al., "Percutaneous electrical nerve stimulation: an alternative to TENS in the management of sciatica," Apr. 26, 1999, Pain 1999, vol. 83, © 1999 International Association for the Study of Pain / Published by Elsevier Science B.V., pp. 193-199.

Gimple, M.D., Lawrence et al., "Effect of Chronic Subcutaneous or Intramural Administration of Heparin on Femoral Artery Restenosis After Balloon Angioplasty in Hypercholesterolemic Rabbits" Laboratory Investigation, Circulation, vol. 86, No. 5, Nov. 1992, pp. 1536-1546.

Goldberger, Jeffrey J. et al., "New technique for vagal nerve stimulation," Jun. 2, 1999, Journal of Neuroscience Methods 91, © 1999 Elsevier Science B.V., pp. 109-114.

Gorbunov, F.E. et al., "The Use of Pulsed and Continuous Short Wave Diathermy (Electric Field) in Medical Rehabilitation of the Patients with Guillain-Barre Syndrome and Other Peripheral Myelinopathies," May 6, 1994, 5 pages (most of article in Russian language).

Greenwell, T.J. et al., "The outcome of renal denervation for managing loin pain haematuria syndrome," Oct. 30, 2003, Institute of Urology and Nephrology, London, UK, © 2004 BJU International, 4 pages.

Gruberg, Luis, M.D. et al., "The Prognostic Implications of Further Renal Function Deterioration Within 48 h of Interventional Coronary Procedures in Patients with Pre-existent Chronic Renal Insufficiency," Jun. 19, 2000, Journal of the American College of Cardiology 2000, vol. 36, No. 5, © 2000 by the American College of Cardiology, pp. 1542-1548.

Hajjar, Ihab, M.D., M.S. and Theodore A. Kotchen, M.D., "Trends in Prevalence, Awareness, Treatment, and Control of Hypertension in the United States, 1988-2000," JAMA, Jul. 9, 2003, vol. 290, No. 2, pp. 199-206.

Hamza, M.D., Mohamed A. et al., "Effect of the Duration of Electrical Stimulation on the Analgesic Response in Patients with Low Back Pain," Anesthesiology, vol. 91, No. 6, Dec. 1999, © 1999 American Society of Anesthesiologists, Inc., pp. 1622-1627.

Han, Hyo-Kyung and Gordon L. Amidon, "Targeted Prodrug Design to Optimize Drug Delivery," Mar. 21, 2000, AAPS Pharmsci. 2000, vol. 2, No. 1, article 6, pp. 1-11.

Higuchi, Yoshinori, M.D., Ph.D. et al., "Exposure of the Dorsal Root Ganglion in Rats to Pulsed Radiofrequency Currents Activates Dorsal Horn Lamina I and II Neurons," Dec. 4, 2001, Experimental Studies, Neurosurgery, vol. 50, No. 4, Apr. 2002, pp. 850-856.

Hildebrand, Keith R., D.V.M., Ph.D. et al., "Stability, Compatibility, and Safety of Intrathecal Bupivacaine Administered Chronically via an Implantable Delivery System," May 18, 2001, The Clinical Journal of Pain, vol. 17, No. 3, © 2001 Lippincott Williams & Wilkins Inc., pp. 239-244.

Hing, Esther, M.P.H. and Kimberly Middleton, B.S.N., M.P.H., "National Hospital Ambulatory Medical Care Survey: 2001 Outpatient Department Summary," Aug. 5, 2003, Advance Data From Vital and Health Statistics, No. 338, CDC, 32 pages.

Horwich, Tamara, M.D., "New Advances in the Diagnosis and Management of Acute Decompensated Heart Failure," the Heart.org Satellite program, Rapid Review, CME Symposium presented on Nov. 8, 2004 at the Sheraton New Orleans Hotel, 4 pages.

Huang, Yifei et al., "Remodeling of the chronic severely failing ischemic sheep heart after coronary microembolization: functional, energetic, structural, and cellular responses," Jan. 8, 2004, Am J Physiol. 2004, vol. 286, © 2004 the American Physiological Society, pp. H2141-H2150.

Hughes, Gordon B., M.D. et al., "A Comparative Study of Neuropathologic Changes Following Pulsed and Direct Current Stimulation of the Mouse Sciatic Nerve," Jun. 27, 1980, American Journal of Otolaryngology, Nov. 1980, vol. 1, No. 5, pp. 378-384.

Israili, Z.H., "Clinical pharmacokinetics of angiotensin II (AT) receptor blockers in hypertension," Journal of Human Hypertension 2000, Macmillan Publishers Ltd., vol. 14, pp. S73-S86.

Janssen, Ben J.A. et al., "Effects of complete renal denervation and selective afferent renal denervation on the hypertension induced by intrarenal norepinephrine infusion on conscious rats," Jan. 4, 1989, Journal of Hypertension 1989, vol. 7, No. 6, © 1989 Current Science Ltd., pp. 447-455.

Johansson, Bjorn, "Electrical Membrane Breakdown, A Possible Mediator of the Actions of Electroconvulsive Therapy," Medical Hypotheses 1987, vol. 24, © 1987 Longman Group UK Ltd., pp. 313-324.

Jorgensen, William A. et al, "Electrochemical Therapy of Pelvic Pain: Effects of Pulsed Electromagnetic Fields (PEMF) on Tissue Trauma," Eur. J. Surg. 1994, vol. 160, Suppl. 574, © 1994 Scandinavian University Press, pp. 83-86.

Joshi, R.P. et al., "Improved energy model for membrane electroporation in biological cells subjected to electrical pulses," Apr. 9, 2002, Physical Review E, vol. 65, 041920-1, © 2002 The American Physical Society, 8 pages.

Joshi, R.P. et al., "Self-consistent simulations of electroporation dynamics in biological cells subjected to ultrashort electrical pulses," Jun. 21, 2001, Physical Review E, vol. 64, 011913, © 2001The American Physical Society, pp. 1-10.

Joshi, R.P., K.H. Schoenbach, "Mechanism for membrane electroporation irreversibility under high-intensity, ultrashort electrical pulse conditions," Nov. 11, 2002, Physical Review 2002, E 66, © 2002 The American Physical Society, pp. 052901-1-052901-4.

Kanduser, Masa et al., "Effect of surfactant polyoxyethylene glycol $(C_{12}E_8)$ on electroporation of cell line DC3F," Aug. 20, 2002, Colloids and Surfaces A: Physiochem. Eng. Aspects 2003, vol. 214, © 2002 Elsevier Science B.V., pp. 205-217.

Katholi, Richard E., "Renal nerves in the pathogenesis of hypertension in experimental animals and humans," Am J Physiol., vol. 245, © 1983 the American Physiological Society, pp. Fl-F14.

Kelleher, Catherine L. et al., "Characteristics of Hypertension in Young Adults With Autosomal Dominant Polycystic Kidney Disease Compared With the General U.S. Population," Jun. 9, 2004, American Journal of Hypertension 2004, pp. 1029-1034.

King, Ronald W.P., "Nerves in a Human Body Exposed to Low-Frequency Electromagnetic Fields," Jun. 7, 1999, IEEE Transactions on Biomedical Engineering Dec. 1999, vol. 46, No. 12, © 1999 IEEE, pp. 1426-1431.

Kinney, Brian M., M.D., "High-Tech Healing—The evolution of therapeutic electromagnetic fields in plastic surgery," Plastic Surgery Products, Jun. 2004, pp. 32-36, 3 pages.

Kok, R.J. et al., "Specific Delivery of Captopril to the Kidney with the Prodrug Captopril-Lysozyme," Aug. 16, 1998, The Journal of Pharmacology and Experimental Therapeutics, vol. 288, No. 1, © 1999 by the American Society for Pharmacology and Experimental Therapeutics, pp. 281-285.

Kon, Valentina, "Neural Control of Renal Circulation," Miner Electrolyte Metab 1989, vol. 15, © 1989 S. Karger AG, pp. 33-43.

Koyama, Shozo et al., "Relative Contribution of Renal Nerve and Adrenal Gland to Renal Vascular Tone During Prolonged Canine Hemorrhagic Hypotension," Sep. 24, 1992, Circulatory Shock 1993, vol. 39, © 1993 Wiley-Liss Inc., pp. 269-274.

Kozak, Lola Jean, Ph.D. et al., "National Hospital Discharge Survey: 2001 Annual Summary with Detailed Diagnosis and Procedure Data," Vital Health Statistics, Series 13, No. 156, Jun. 2004, CDC, 206 pages.

Lafayette, Richard A., M.D., "How Does Knocking Out Angiotensin II Activity Reduce Renal Injury in Mice?" Jun. 14, 1999, Journal Club, American Journal of Kidney Diseases, vol. 35, No. 1, Jan. 2000, © 2000 National Kidney Foundation Inc., pp. 166-172.

Lavie, Peretz, Ph.D. And Victor Hoffstein, M.D., "Sleep Apnea Syndrome: A Possible Contributing Factor to Resistant Hypertension," Jun. 2001, Sleep 2001, vol. 24, No. 6, pp. 721-725.

Lee, Raphael C. And Jurgen Hannig, "Membrane Biology and Biophysics," Chapter 25, Surgical Research, © 2001 Academic Press, pp. 297-305.

Lee, Raphael C., M.D., Sc.D. and Michael S. Kolodney, S.B., "Electrical Injury Mechanisms: Electrical Breakdown of Cell Membranes," Oct. 1, 1986, Plastic and Reconstructive Surgery Nov. 1987, vol. 80, No. 5, pp. 672-679.

Ligtenberg, Gerry, M.D. et al., "Reduction of Sympathetic Hyperactivity by Enalapril in Patients with Chronic Renal Failure," Apr. 29, 1999, New England Journal of Medicine 1999, vol. 340, No. 17, © 1999 Massachusetts Medical Society, pp. 1321-1328.

Lin, Vernon W. H. et al, "High intensity magnetic stimulation over the lumbosacral spine evokes antinociception in rats," Apr. 16, 2002, Clinical Neurophysiology, vol. 113, © 2002 Elsevier Science Ireland Ltd., pp. 1006-1012.

Lipfert, Peter, M.D. et al., "Tachyphylaxis to Local Anesthetics Does Not Result From Reduced Drug Effectiveness at the Nerve Itself," August 3, 1988, Anesthesiology 1989, vol. 70, pp. 71-75.

Lohmeier Thomas E. et al, "Baroreflexes prevent neurally induced sodium retention in angiotensin hypertension," Am. J. Physiol. Regulatory Integrative Comp. Physiol., vol. 279, © 2000 the American Physiological Society, pp. R1437-R1448.

Lohmeier, Thomas E. And Drew A. Hildebrandt, "Renal Nerves Promote Sodium Excretion in Angiotensin-Induced Hypertension," Oct. 20, 1997, Hypertension 1998, vol. 31, Part 2, © 1998 American Heart Association, Inc., pp. 429-434.

Lohmeier, Thomas E. et al., "Prolonged Activation of the Baroflex Produces Sustained Hypotension," Harry Goldblatt Award, Nov. 26, 2003, Hypertension 2004, vol. 43, part 2, © 2004 American Heart Association, Inc., pp. 306-311.

Lohmeier, Thomas E. et al., "Renal Nerves Promote Sodium Excretion During Long-Term Increases in Salt Intake," Oct. 23, 1998, Hypertension 1999, vol. 33, part 2, © 1999 American Heart Association, pp. 487-492.

Lohmeier, Thomas E. et al., "Sustained influence of the renal nerves to attenuate sodium retention in angiotensin hypertension," Apr. 13, 2001, Am J Physiol Regulatory Integrative Comp. Physiol., vol. 281, © 2001 the American Physiological Society, pp. R434-R443.

Lohmeier, Thomas E., "Interactions Between Angiotensin II and Baroreflexes in Long-Term Regulation of Renal Sympathetic Nerve Activity," Circulation Research, Jun. 27, 2003, © 2003 American Heart Association Inc., pp. 1282-1284.

Luff, S.E. et al., "Two types of sympathetic axon innervating the juxtaglomerular arterioles of the rabbit and rat kidney differ structurally from those supplying other arteries," May 1, 1991, Journal of Neurocytology 1991, vol. 20, © 1991 Chapman and Hall Ltd., pp. 781-795.

Lundborg, C. et al., "Clinical experience using intrathecal (IT) bupivacaine infusion in three patients with complex regional pain syndrome type I (CRPS-I)," Acta Aneaesthesiol. Scand. 1999, vol. 43, pp. 667-678.

Maeder, Micha, M.D. et al., "Contrast Nephropathy: Review Focusing on Prevention," Jun. 22, 2004, Journal of the American College of Cardiology Nov. 2, 2004, vol. 44, No. 9, © 2004 by the American College of Cardiology Foundation, pp. 1763-1771.

Malpas, Simon C., "What sets the long-term level of sympathetic nerve activity: is there a role for arterial baroreceptors?" Invited Review, Am J Physiol Regul. Integr. Comp. Physiol. 2004, vol. 286, © 2004 the American Physiological Society, pp. R1-R12.

Marenzi, Giancarlo, M.D. et al., "The Prevention of Radiocontrast-Agent-Induced Nephropathy by Hemofiltration," New England Journal of Medicine, Oct. 2, 2003, vol. 349 (14), © 2003 Massachusetts Medical Society, pp. 1333-1340.

Martin, Jason B. et al., "Gene Transfer to Intact Mesenteric Arteries by Electroporation," Mar. 27, 2000, Journal of Vascular Research 2000, vol. 37, 2000 S. Karger AG, Basel, pp. 372-380.

McCreery, Douglas B. et al., "Charge Density and Charge Per Phase as Cofactors in Neural Injury Induced by Electrical Stimulation," IEEE Transactions on Biomedical Engineering, vol. 17, No. 10, Oct. 1990, pp. 996-1000.

McCullough, Peter A., M.D., MPH et al., "Acute Renal Failure after Coronary Intervention: Incidence, Risk Factors and Relationship to Mortality," Apr. 14, 1997, Am J Med. 1997, vol. 103, 1997 Excerpta Medica, Inc., pp. 368-375.

McMurray, John J.V., M.D. And Eileen O'Meara, M.D., "Treatment of Heart Failure with Spironolactone-Trial and Tribulations," Aug. 5, 2004, New England Journal of Medicine, vol. 351, No. 6, © 2004 Massachusetts Medical Society, pp. 526-528.

McRobbie, D. and M.A. Foster, "Thresholds for biological effects of time-varying magnetic fields," Dec. 16, 1983, Clin. Phys. Physiol. Meas. 1984, vol. 5, No. 2, © 1984, The Institute of Physics, pp. 67-78.

Medtronic Neurostimulation Systems, "Expanding the Array of Pain Control Solutions," informational pamphlet, 1999 Medtronic, Inc., 6 pages.

Medtronic, "Spinal Cord Stimulation," Patient Management Guidelines for Clinicians, Medtronic, inc. 1999, 115 pages.

Medtronic, "SynchroMed Infusion System—Clinical Reference Guide for Pain Therapy," Medtronic, Inc. 1998, 198 pages.

Mess, Sarah A., M.D. et al., "Implantable Baclofen Pump as an Adjuvent in Treatment of Pressure Sores," Mar. 1, 2003, Annals of Plastic Surgery, vol. 51, No. 5, Nov. 2003, © 2003 Lippincott Williams & Wilkins, pp. 465-467.

Mihran, Richard T. et al., "Temporally-Specific Modification of Myelinated Axon Excitability in Vitro Following a Single Ultrasound Pulse," Sep. 25, 1989, Ultrasound in Med.& Biol. 1990, vol. 16, No. 3, pp. 297-309.

Mitchell, G.A.G., "The Nerve Supply of the Kidneys," Aug. 20, 1949, Acta Anatomica, vol. 10, Fasc. 1/2, 1950, pp. 1-37.

Moss, Nicholas G., "Renal function and renal afferent and efferent nerve activity," Am J Physiol 1982, vol. 243, © 1982, the American Physiological Society, pp. F425-F433.

Munglani, Rajesh, "The longer term effect of pulsed radiofrequency for neuropathic pain," Jun. 8, 1998, Pain, vol. 80, © 1999 International Association for the Study of Pain, Published by Elsevier Science B.V., pp. 437-439.

Naropin (ropivacaine HCl) injection, Rx only description, AstraZeneca 2001, 3 pages.

National High Blood Pressure Education Program, "1995 Update of the Working Group Reports on Chronic Renal Failure and Renovascular Hypertension," presentation, 13 pages.

National Kidney Foundation, "Are You At Increased Risk for Chronic Kidney Disease?" © 2002 National Kidney Foundation, Inc., 14 pages.

Nikolsky, Eugenia, M.D. et al., "Radiocontrast Nephropathy: Identifying the High-Risk Patient and the Implications of Exacerbating Renal Function," Rev Cardiovasc Med. 2003, vol. 4, Supp. 1, © 2003 MedReviews, LLC, pp. S7-S14.

Palmer, Biff F., M.D., "Managing Hyperkalemia Caused by Inhibitors of the Renin-Angiotensin-Aldosterone System," Aug. 5, 2004, The New England Journal of Medicine 2004, vol. 351, No. 6, © 2004 Massachusetts Medical Society, pp. 585-592.

Peacock, J.M. And R. Orchardson, "Action potential conduction block of nerves in vitro by potassium citrate, potassium tartrate and potassium oxalate," May 6, 1998, Journal of Clinical Periodontology, © 1999 Munksgaard, vol. 26, pp. 33-37.

Pettersson, A. et al., "Renal interaction between sympathetic activity and ANP in rats with chronic ischaemic heart failure," Nov. 25, 1998, Acta Physiol. Scand. 1989, vol. 135, pp. 487-492.

Pliquett, U., "Joule heating during solid tissue electroporation," Oct. 22, 2002, Medical & Biological Engineering and Computing 2003, vol. 41, pp. 215-219.

Popovic, Jennifer .R. And Margaret J. Hall," 1999 National Hospital Discharge Survey," Advance Data, No. 319, CDC, pp. 1-17 & 20.

Practice Guidelines Writing Committee and ESH/ESC Hypertension Guidelines Committee, "Practice Guidelines for Primary Care Physicians: 2003 ESH/ESC Hypertension Guidelines," Published in Journal of Hypertension 2003, vol. 21, No. 10: 1011-1053, © 2003 European Society of Hypertension, pp. 1779-1786.

Pucihar, Gorazd et al., "The influence of medium conductivity on electropermeabilization and survival of cells in vitro," May 31, 2001, Bioelectrochemistry, vol. 54, 2001, Elsevier Science B.V. 2001, pp. 107-115.

Raji, A. R. M. and R. E. M. Bowden, "Effects of High-Peak Pulsed Electromagnetic Field on the Degeneration and Regeneration of the Common Peroneal Nerve in Rats," The Journal of Bone and Joint Surgery Aug. 1983, vol. 65-B, No. 4, © 1983 British Editorial Society of Bone and Joint Surgery, pp. 478-492.

Ram, C. Venkata S., M.D., "Understanding refractory hypertension," May 15, 2004, Patient Care May 2004, vol. 38, pp. 12-16, 7 pages from.

Ribstein, Jean and Michael H. Humphreys, "Renal nerves and cation excretion after acute reduction in functioning renal mass in the rat," Sep. 22, 1983, Am J Physiol, vol. 246, © 1984 the American Physiological Society, pp. F260-F265.

Richebe, Philippe, M.D. et al., "Immediate Early Genes after Pulsed Radiofrequency Treatment: Neurobiology in Need of Clinical Trials," Oct. 13, 2004, Anesthesiology Jan. 2005, vol. 102, No. 1, © 2004 American Society of Anesthesiologists, Inc. Lippincott Williams & Wilkins, Inc., pp. 1-3.

Rihal, Charanjit S. et al., "Incidence and Prognostic Importance of Acute Renal Failure After Percutaneous Coronary Intervention," Mar. 6, 2002, Circulation May 14, 2002, vol. 10, © 2002 American Heart Association, Inc., pp. 2259-2264.

Rosen, S.M. et al., "Relationship of Vascular Reactivity to Plasma Renin Concentration in Patients with Terminal Renal Failure," Proc. Dialysis Transplant Forum 1974, pp. 45-47.

Roth, Bradley J. And Peter J. Basser, "A Model of the Stimulation of a Nerve Fiber by Electromagnetic Induction," IEEE Transactions on Biomedical Engineering, vol. 37, No. 6, Jun. 1990, pp. 588-597.

Rudin, Asa, M.D. et al., "Postoperative Epidural or Intravenous Analgesia after Major Abdominal or Thoraco-Abdominal Surgery," The Journal of the American Society of Anesthesiologists, Inc., Anesthesiology 2001, vol. 95, A-970, 1 page.

Rudnick, Michael R. et al., "Contrast-induced nephropathy: How it develops, how to prevent it," Cleveland Clinic Journal of Medicine Jan. 2006, vol. 73, No. 1, pp. 75-87.

Ruohonen, Jarmo et al., "Modeling Peripheral Nerve Stimulation Using Magnetic Fields," Journal of the Peripheral Nervous System 1997, vol. 2, No. 1, © 1997 Woodland Publications, pp. 17-29.

Scheiner, Avram, Ph.D., "The design, development and implementation of electrodes used for functional electrical stimulation," Thesis paper, Case Western Reserve University, May 1992, 220 pages.

Schoenbach, Karl H. et al., "Intracellular Effect of Ultrashort Electrical Pulses," Dec. 26, 2000, Bioelectromagnetics 2001, vol. 22, © 2001 Wiley-Liss Inc., pp. 440-448.

Schrier, Robert et al., "Cardiac and Renal Effects of Standard Versus Rigorous Blood Pressure Control in Autosomal-Dominant Polycystic Kidney Disease," Mar. 23, 2002, Journal of the American Society of Nephrology, © 2002 American Society of Nephrology, pp. 1733-1739.

Shupak, Naomi M., "Therapeutic Uses of Pulsed Magnetic-Field Exposure: A Review," Radio Science Bulletin Dec. 2003, No. 307, pp. 9-32.

Simpson, B. et al, "Implantable Spinal Infusion Devices for Chronic Pain and Spasticity: An Accelerated Systematic Review," ASERNIP-S Report No. 42, May 2003, 56 pages.

Sisken, B.F. et al., "229.17 Influence of Non-Thermal Pulsed Radiofrequency Fields (PRF) on Neurite Outgrowth," Society for Neuroscience, vol. 21, 1995, 2 pages.

Skeie, B. et al., "Effect of chronic bupivacaine infusion on seizure threshold to bupivacaine," Dec. 28, 1986, Acta Anaesthesiol. Scand. 1987, vol. 31, pp. 423-425.

Skopec, M., "A Primer on Medical Device Interactions with Magnetic Resonance Imaging Systems," Feb. 4, 1997, CDRH Magnetic Resonance Working Group, U.S. Department of Health and Human Services, Food and Drug Administration, Center for Devices and Radiological Health, Updated May 23, 1997, 17 pages, http://www.fde.gov/cdrh/ode/primerf6.html, (last accessed Jan. 23, 2006.

Slappendel, Robert et al., "The efficacy of radiofrequency lesioning of the cervical spinal dorsal root ganglion in a double blinded rendomized study," Jun. 26, 1997, Pain, vol. 73, © 1997 International Association of the Study of Pain, Elsevier Science B.V., pp. 159-163.

Sluijter, M.D., Ph.D., "Pulsed Radiofrequency," May 17, 2005, Anesthesiology Dec. 2005, vol. 103, No. 6, © 2005 American Society of Anesthesiologists, Inc. Lippincott Williams & Wilkins, Inc., pp. 1313-1314.

Sluijter, M.D., Ph.D., "Radiofrequency Part 1: The Lumbosacral Region," Chapter 1 Mechanisms of Chronic Pain and part of Chapter 2 Spinal Pain, © 2001 FlivoPress SA, Meggen (LU), Switzerland, pp. 1-26.

Sluijter, M.D., Ph.D., "The Role of Radiofrequency in Failed Back Surgery Patients," Current Review of Pain 2000, vol. 4, © 2000 by Current Science Inc., pp. 49-53.

Souza, D.R.B. et al., "Chronic experimental myocardial infarction produces antinatriuresis by a renal nerve-dependent mechanism," Oct. 14, 2003, Brazilian Journal of Medical and Biological Research 2004, vol. 37, pp. 285-293.

Standl, Thomas, M.D., et al, "Patient-controlled epidural analgesia reduces analgesic requirements compared to continuous epidural infusion after major abdominal surgery," Aug. 29, 2002, Canada Journal of Anesthesia 2003, vol. 50, No. 3, pp. 258-264.

Stone, Gregg W., M.D. et al., "Fenoldopam Mesylate for the Prevention of Contrast-Induced Nephropathy," JAMA Nov. 5, 2003, vol. 290, No. 17, © 2003 American Medical Association, pp. 2284-2291.

Sung, Duk Hyun, M.D. et al., "Phenol Block of Peripheral Nerve Conduction: Titrating for Optimum Effect," Jun. 27, 2000, Arch. Phys. Med. Rehabil., vol. 82, May 2001, pp. 671-676.

Taler, Sandra J. et al., "Resistant Hypertension, Comparing Hemodynamic Management to Specialist Care," Mar. 12, 2002, Hypertension 2002, vol. 39, 2002 American Heart Association, Inc., pp. 982-988.

Tay, Victoria KM et al., "Computed tomography fluoroscopy-guided chemical lumbar sympathectomy: Simple, safe and effective," Oct. 31, 2001, Diagnositc Radiology, Australasian Radiology 2002, vol. 46, pp. 163-166.

Thompson, Gregory W. et al, "Bradycardia Induced by Intravascular Versus Direct Stimulation of the Vagus Nerve," Aug. 24, 1997, The Society of Thoracic Surgeons 1998, pp. 637-642.

Thrasher, Terry N., "Unloading arterial baroreceptors causes neurogenic hypertension," Dec. 4, 2001, Am J Physiol Regulatory Integrative Comp. Physiol., vol. 282, © 2002 the American Physiological Society, pp. R1044-R1053.

Tokuno, Hajime A. et al., "Local anesthetic effects of cocaethylene and isopropylcocaine on rat peripheral nerves," Oct. 7, 2003, Brain Research 996, 2004, © 2003 Elsevier B.V., pp. 159-167.

Trapani, Angelo J. et al., "Neurohumoral interactions in conscious dehydrated rabbit," Am J Physiol 1988, vol. 254, © 1988 the American Physiological Society, pp. R338-R347.

Trock, David H. et al., "The Effect of Pulsed Electromagnetic Fields in the Treatment of Osteoarthritis of the Knee and Cervical Spine. Report of Randomized, Double Blind, Placebo Controlled Trials," Mar. 22, 1994, The Journal of Rheumatology 1994, vol. 21, pp. 1903-1911.

Troiano, Gregory C. et al., "The Reduction in Electroporation Voltages by the Addition of a Surfactant to Planar Lipid Bilayers," May 12, 1998, Biophysical Journal, vol. 75, Aug. 1998, © the Biophysical Society, pp. 880-888.

Trumble, Dennis R., and James A. Magovern, "Comparison of Dog and Pig Models for Testing Substernal Cardiac Compression Devices," Nov. 2003, ASAIO Journal 2004, pp. 188-192.

Tsai, E., "Intrathecal drug delivery for pain indications, technique, results," Pain Lecture presentation, Jun. 8, 2001, 31 pages.

Uematsu, Toshihiko, M.D., Ph.D., F.I.C.A. et al., "Extrinsic Innervation of the Canine Superior Vena Cava, Pulmonary, Portal and Renal Veins," Angiology-Journal of Vascular Diseases, Aug. 1984, pp. 486-493.

United States Renal Data System, "USRDS 2003 Annual Data Report: Atlas of End-Stage Renal Disease in the United States," National Institutes of Health, National Institute of Diabetes and Digestive and Kidney Diseases, 2003, 593 pages.

Upadhyay, Pramod, "Electroporation of the skin to deliver antigen by using a piezo ceramic gas igniter," January 27, 2001, International Journal of Pharmaceutics, vol. 217, © 2001 Elsevier Science B.V., pp. 249-253.

Valente, John F. et al., "Laparoscopic renal denervation for intractable ADPKD-related pain," Aug. 24, 2000, Nephrology Dialysis Transplantation 2001, vol. 16, European Renal Association-European Dialysis and Transplant Association, p. 160.

Velazquez, Eric J., "An international perspective on heart failure and left ventricular systolic dysfunction complicating myocardial infarction: the VALIANT registry," Aug. 5, 2004, European Heart Journal, vol. 25, © 2004 Elsevier Ltd., pp. 1911-1919.

Velez-Roa, Sonia, M.D., et al., "Peripheral Sympathetic Control During Dobutamine Infusion: Effects of Aging and Heart Failure," Jul. 7, 2003, Journal of the American College of Cardiology 2003, vol. 42, No. 9, © 2003 American College of Cardiology Foundation, pp. 1605-1610.

Villarreal, Daniel et al., "Effects of renal denervation on postprandial sodium excretion in experimental heart failure," Oct. 29, 1993, Am J Physiol 266, 1994, pp. R1599-R1604.

Villarreal, Daniel et al., "Neurohumoral modulators and sodium balance in experimental heart failure," Nov. 6, 1992, Am J Physiol, vol. 264, 1993, pp. H1187-H1193.

Wagner, C.D. et al, "Very low frequency oscillations in arterial blood pressure after autonomic blockade in conscious dogs," Feb. 5, 1997, Am J Physiol Regul Integr Comp Physiol 1997, vol. 272, © 1997 the American Physiological Society, pp. 2034-2039.

Wald, Jan D. Ph.D. et al., "Cardiology Update 2003," Sep. 11, 2003, © 2003 AG Edwards, 120 pages.

Wang, Xi et al., "Alterations of adenylyl cyclase and G proteins in aortocaval shut-induced heart failure," Jul. 2004, Am J Physiol Heart Circ Physiol., vol. 287, © 2004 the American Physiological Society, pp. H118-H125.

Weaver, James C., "Electroporation: A General Phenomenon for Manipulating Cells and Tissues," Oct. 22, 1992, Journal of Cellular Biochemistry, vol. 51, © 1993 Wiley-Liss, Inc., pp. 426-435.

Weiner, Richard L., M.D., "Peripheral nerve neurostimulation," Neurosurgery Clinics of North America 2003, vol. 14, © 2003 Elsevier Inc., pp. 401-408.

Weisbord, Steven D., M.D. And Paul M. Palevsky, M.D., "Radiocontrast-Induced Acute Renal Failure," Jul. 10, 2004, Journal of Intensive Care Medicine 2005, vol. 20 (2), © 2005, Sage Publications, pp. 63-75.

Wolinsky, Harvey, M.D., Ph.D. And Swan N. Thung, M.D., "Use of a Perforated Balloon Catheter to Deliver Concentrated Heparin Into the Wall of the Normal Canine Artery," Aug. 30, 1989, JACC 1990, vol. 15, ©1990 the American College of Cardiology, pp. 475-481.

Wyss, J.Michael et al., "Neuronal control of the kidney: Contribution to hypertension," Apr. 8, 1991, Can. J. Physiol. Pharmacol., vol. 70, 1992, pp. 759-770.

Yamaguchi, Jun-ichi et al., "Prognostic Significance of Serum Creatinine Concentration for In-Hospital Mortality in Patients With Acute Myocardial Infarction Who Underwent Successful Primary Percutaneous Coronary Intervention (from the Heart Institute of Japan Acute Myocardial Infarction [HIJAMI] Registry)," Feb. 24, 2004, The American Journal of Cardiology, vol. 93, Jun. 15, 2004, © 2004 by Excerpta Medica, Inc., pp. 1526-1528.

Ye, Shaohua et al., "Renal Injury Caused By Intrarenal Injection of Phenol Increases Afferent and Efferent Renal Sympathetic Nerve Activity," Mar. 12, 2002, American Journal of Hypertension Aug. 2002, vol. 15, No. 8, © 2002 the American Journal of Hypertension, Ltd. Published by Elsevier Science Inc., pp. 717-724.

Young, James B., M.D., FACC, "Management of Chronic Heart Failure: What Do Recent Clinical Trials Teach Us?" Reviews in Cardiovascular Medicine 2004, vol. 5, Suppl. 1, © 2004 MedReviews, LLC, pp. S3-S9.

Zanchetti, A. et al., "Neural Control of the Kidney—Are There Reno-Renal Reflexes?" Clin. and Exper. Hyper. Theory and Practice, A6 (1&2), © 1984 Marcel Dekker Inc., pp. 275-286.

Zimmermann, Ulrich, "Electrical Breakdown, Electropermeabilization and Electrofusion," Rev. Physiol. Biochem. Pharmacol., vol. 105, © Springer-Verlag 1986, pp. 175-256.

Zucker, Irving H. et al., "The origin of sympathetic outflow in heart failure: the roles of angiotensin II and nitric oxide," Progress in Biophysics & Molecular Biology 2004, vol. 84, © 2003 Elsevier Ltd., pp. 217-232.

Zundert, Jan Van M.D. FIPP andAlex Cahana, M.D. Daapm, "Pulsed radiofrequency in Chronic Pain Management: Looking for the Best Use of Electrical Current," Pain Practice 2005, vol. 5, Issue 2, © 2005 World Institute of Pain, pp. 74-76.

Cameron, Tracy. "Micromodular Implants to Provide Electrical Stimulation of Paralyzed Muslces and Limbs." IEEE Transactions on Biomedical Engineering, vol. 44, No. 9, Sep. 1997. pp. 781-790.

Guimaraes, Sarfim. "Vascular Adrenoceptors: An Update" pp. 319-356.

Hammer, Leah W. "Differential Inhibition of Functional Dilation of Small Arterioles by Indomethacin and Glibenclamide." Hypertension. Feb. 2001 Part II. pp. 599-603.

Hortobagyi, Gabriel N. "Randomized Trial of High-Dose Chemotherapy and Blood Cell Autografts for High-Risk Primary Breast Carcinoma" Journal of the National Cancer Institute, vol. 92, No. 3, Feb. 2, 2000 pp. 225-233.

Janda, J., "Impact of the electrical stimulation apparatus rebox on the course of ischemic renal damage in rats," British Library-"The world's knowledge" pp. 252-254 (translated and untranslated versions).

U.S. Appl. No. 10/900,199, filed Jul. 28, 2004, Gelfand.
U.S. Appl. No. 11/129,765, filed May 13, 2005, Deem.
U.S. Appl. No. 11/133,925, filed May 20, 2005, Gelfand.
U.S. Appl. No. 11/144,173, filed Jun. 3, 2005, Levin et al.
U.S. Appl. No. 11/144,298, filed Jun. 3, 2005, Levin et al.
U.S. Appl. No. 11/145,122, filed Jun. 3, 2005, Levin et al.
U.S. Appl. No. 11/189,563, filed Jul. 25, 2005, Deem.

Augustyniak, R.A. et al., "Sympathetic Overactivity as a Cause of Hypertension in Chronic Renal Failure," Journal of Hypertension, 2002, 20:3-9, Lippincott Williams & Wilkins Press.

Berde, C. et al. "Local Anesthetics," Anesthesia, Chapter 13, 5th addition, pp. 491-521, Churchill-Livingston, Philadelphia 2000.

Blad, B., et al., "An Electrical Impedance index to Assess Electroporation in Tissue," Tissue and Organ (Therapy), pp. 31-34, <http://www.bl.uk> 2001, Oslo.

Braunwald, E., Heart Disease, "A Textbook of Cardiovascular Medicine," 5th Ed., vol. 2, 1997, pp. 480-481, 824-825, 1184-1288 and 1923-1925, W.B. Saunders Company.

Cahana, A. et al., "Acute Differential Modulation of Synaptic Transmission and Cell Survival During Exposure to Pulsed and Continuous Radiofrequency Energy," The Journal of Pain, May 2003, pp. 197-202, vol. 4, No. 4, © 2003 by the American Pain Society.

Campese, V.M. et al., "Renal Afferent Denervation Prevents the Progression of Renal Disease in the Renal Ablation Model of Chronic Renal Failure in the Rat," American Journal of Kidney Diseases, Nov. 1995, pp. 861-865, vol. 26, No. 5.

Davalos, R. et al., "Electrical Impedance Tomography for Imaging Tissue Electroporation," IEEE Transactions on Biomedical Engineering, vol. 51, No. 5, May 2004, pp. 761-767, 2004 IEEE.

DiBona, G., "Neural Control of the Kidney: Functionally Specific Renal Sympathetic Nerve Fibers," Am J Physiol Regulatory Integrative Comp Physiol, 2000, 279: R1517-R1524, The American Physiological Society, Bethesda, MD.

DiBona, G.F. et al., "Nervous Kidney, Interaction Between Renal Sympathetic Nerves and the Renin-Angiotensin System in the Control of Renal Function," Hypertension, 2000, 36:1083-1088, American Heart Association, Inc.

DiBona, G.F., "Functionally Specific Renal Sympathetic Nerve Fibers: Role in Cardiovascular Regulation," American Journal of Hypertension, Jun. 2001, 14:163S-170S.

DiBona, G.F., "Sympathetic Nervous System and the Kidney in Hypertension," Current Opinion in Nephrology and Hypertension, 2002, 11:197-200, Lippincott Williams & Wilkins Press.

Dueck, R. et al., "Noninvasive Cardiac Output Monitoring," The Cardiopulmonary and Critical Care Journal, Chest, 120, 2, Aug. 2001, pp. 339-341, American College of Chest Physicians.

Gehl, J. et al., "In Vivo Electroporation of Skeletal Muscle: Threshold, Efficacy and Relation to Electric Field Distribution," Biochimica et Biophysica Acta, 1428, 1999, pp. 233-240, www.elsevier.com/locate/bba <http://www.elsevier.com/locate/bba>.

Heida, T., et al., "Investigating Membrane Breakdown of Neuronal Cells Exposed to Nonuniform Electric Fields by Finite-Element Modeling and Experiments," IEEE Transactions on Biomedical Engineering, vol. 49, No. 10, Oct. 2002, pp. 1195-1203, © 2002 IEEE.

Hopp, F. A. et al., "Respiratory Responses to Selective Blockade of Carotid Sinus Baroreceptors in the Dog," Am J Physiol Regul Integr Comp Physiol, 1998, 275:10-18, American Physiological Society, Bethesda, MD.

Huang, Wann-Chu et al. "Renal Denervation Prevents and Reverses Hyperinsulinemia—Induced Hypertension in Rats," Hypertension, 1998, 32:249-254, American Heart Association, Inc.

International Search Report, PCT/US04/38498, Mailed Feb. 18, 2005, Applicant: G & L Consulting, LLC (3 pages).

Lee, R. C., et al., "Biophysical Injury Mechanisms in Electrical Shock Trauma," Annu. Rev. Biomed. Eng., 2000. 02:477-509, Copyright © 2000 by Annual Reviews.

Medtronic Inc., MiniMed 2007, Implantable Insulin Pump System, Shoreview, MN (4 pages).

Miklavcic, D. et al, "A Validated Model of in Vivo Electric Field Distribution in Tissues for Electrochemotherapy and for DNA Electrotransfer for Gene Therapy," Biochimica et Biophysica Acta, 1523, 2000, pp. 73-83, www.elsevier.com/locate/bba http://www.elsevier.com/locate/bba.

Nelson, L. et al., "Neurogenic Control of Renal Function in Response to Graded Nonhypotensive Hemorrahage in Conscious Dogs," 1993, pp. R661-R667, American Physiological Society.

Nozawa, T. et al., "Effects of Long Term Renal Sympathetic Denervation on Heart Failure After Myocardial Infarction in Rats," Heart Vessels, 2002, 16:51-56.

Podhajsky, R.J., et al. "The Histologic Effects of Pulsed and Continuous Radiofrequency Lesions at 40° C to Rat Dorsal Root Ganglion and Sciatic Nerve," SPINE, vol. 30, No. 9, pp. 1008-1013, Lippincott Williams & Wilkins Inc.

Rump, L.C., "The Role of Sympathetic Nervous Activity in Chronic Renal Failure," J Clinical Basic Cardiology, 2001, 4:179-182, Department of Internal Medicine, University of Freiburg, Germany.

* cited by examiner

METHODS AND APPARATUS FOR INDUCING CONTROLLED RENAL NEUROMODULATION

CROSS REFERENCE TO RELATED APPLICATION

The present application is a continuation of U.S. application Ser. No. 11/233,814 filed Sep. 23, 2005, now abandoned which claims priority to U.S. Provisional Application No. 60/624,793, filed Nov. 2, 2004, and U.S. Provisional Application No. 60/718,686 filed Sep. 20, 2005. The disclosure of each application is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for renal neuromodulation. More particularly, the present invention relates to methods and apparatus for achieving renal neuromodulation via electroporation or electrofusion. Methods and apparatus for monitoring and controlling neuromodulation, as well as electrical waveforms for inducing such neuromodulation, are provided.

BACKGROUND

Congestive Heart Failure ("CHF") is a condition that occurs when the heart becomes damaged and reduces blood flow to the organs of the body. If blood flow decreases sufficiently, kidney function becomes impaired, which results in fluid retention, abnormal hormone secretions and increased constriction of blood vessels. These results increase the workload of the heart and further decrease the capacity of the heart to pump blood through the kidney and circulatory system.

It is believed that progressively decreasing perfusion of the kidney is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidney can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidney. An increase in renal sympathetic nerve activity leads to vasoconstriction of blood vessels supplying the kidney, decreased renal blood flow, decreased removal of water and sodium from the body, and increased renin secretion. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, co-pending U.S. patent applications Ser. No. 11/129,765, filed on May 13, 2005, and Ser. No. 11/189,563, filed on Jul. 25, 2005, both of which are incorporated herein by reference in their entireties. A pulsed electric field (PEF) may initiate renal neuromodulation, e.g., denervation, via irreversible electroporation. The PEF may be delivered from apparatus positioned intravascularly, extravascularly, transvascularly or a combination thereof.

As used herein, electroporation and electropermeabilization are methods of manipulating the cell membrane or intracellular apparatus. For example, short, high-energy pulses open pores in cell membranes. The extent of porosity in the cell membrane (e.g., size and number of pores) and the duration of the pores (e.g., temporary or permanent) are a function of multiple variables, such as field strength, pulse width, duty cycle, field orientation, cell type and other parameters.

Cell membrane pores will generally close spontaneously upon termination of relatively lower strength fields or relatively shorter pulse widths (herein defined as "reversible electroporation"). However, each cell or cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes.

When a PEF sufficient to initiate irreversible electroporation is applied to renal nerves and/or other neural fibers that contribute to renal neural functions, applicants believe that denervation induced by the PEF would result in increased urine output, decreased renin levels, increased urinary sodium excretion and/or controlled blood pressure that would prevent or treat CHF, hypertension, renal system diseases, and other renal anomalies. PEF systems could be used to modulate efferent or afferent nerve signals, as well as combinations of efferent and afferent signals.

A potential challenge of using PEF systems for treating renal disorders is monitoring the onset and the extent of electroporation, such as determining whether the electroporation is reversible or irreversible. Furthermore, it may also be challenging to selectively electroporate target cells without affecting other cells. For example, it may be desirable to irreversibly electroporate renal nerve cells that travel along or in proximity to renal vasculature, but it may not desirable to damage the smooth muscle cells of which the vasculature is composed. As a result, an overly aggressive course of PEF therapy may damage the renal vasculature, but an overly conservative course of PEF therapy may not achieve the desired renal neuromodulation.

In view of the foregoing, it would be desirable to provide methods and apparatus for monitoring and controlling renal neuromodulation, as well as electrical waveforms for achieving desired neuromodulatory effects.

SUMMARY

The present invention provides methods and apparatus for monitoring and controlling pulsed electric field (PEF) renal neuromodulation, e.g., denervation, as well as PEF waveforms for inducing desired neuromodulatory effects. Embodiments of the invention may be configured for intravascular, extravascular and/or transvascular inducement, monitoring and control of renal neuromodulation.

Pulsed electric field parameters can include, but are not limited to, voltage, field strength, pulse width, pulse duration, the shape of the pulse, the number of pulses and/or the interval between pulses (e.g., duty cycle). Suitable field strengths include, for example, strengths of up to about 10,000 V/cm. Suitable pulse widths include, for example, widths of up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, combinations thereof, etc. Suitable numbers of pulses include, for example, at least one pulse. Suitable pulse intervals include, for example, intervals less than about 10 seconds. These parameters are provided for the sake of illustration and should in no way be considered limiting. Any combination of parameters may be utilized, as desired. PEF waveforms for inducing desired neuromodulatory effects are provided.

Tissue impedance or conductivity may be monitored to determine the effects of pulsed electric field therapy, e.g., to determine an extent of electroporation and its degree of irreversibility. Pulsed electric field electroporation of tissue causes a decrease in tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after terminating the pulsed electric field. Thus, monitoring the impedance or conductivity of the target structure may be utilized to determine the onset of electroporation and to determine the type or extent of electroporation. Furthermore, monitoring data may be used in one or more manual or automatic feedback loops to control the electroporation.

Monitoring elements preferably are in electrical contact or in close proximity with the tissue being monitored. Thus, intravascular and/or extravascular monitoring elements may be utilized to monitor electroporation of smooth muscle cells and/or of the vessel wall. Likewise, transvascular and/or extravascular elements may be utilized to monitor electroporation of neural fibers that contribute to renal function and/or of surrounding tissues.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

The present invention relates to methods and apparatus for monitoring and controlling pulsed electric field (PEF) renal neuromodulation, e.g., denervation, as well as PEF waveforms for inducing desired neuromodulatory effects. Embodiments of the invention may be configured for intravascular, extravascular and/or transvascular inducement, monitoring and control of renal neuromodulation. A combination of intravascular, extravascular and/or transvascular elements optionally may be utilized. The apparatus and methods described herein may exploit any suitable electrical signal or field parameters, e.g., any electric field that will achieve the desired neuromodulation (e.g., electroporative effect). To better understand the structures of devices of the present invention and the methods of using such devices for neuromodulation and monitoring, it is instructive to examine the renal anatomy in humans.

B. Selected Embodiments of Methods for Neuromodulation

Figure 1:
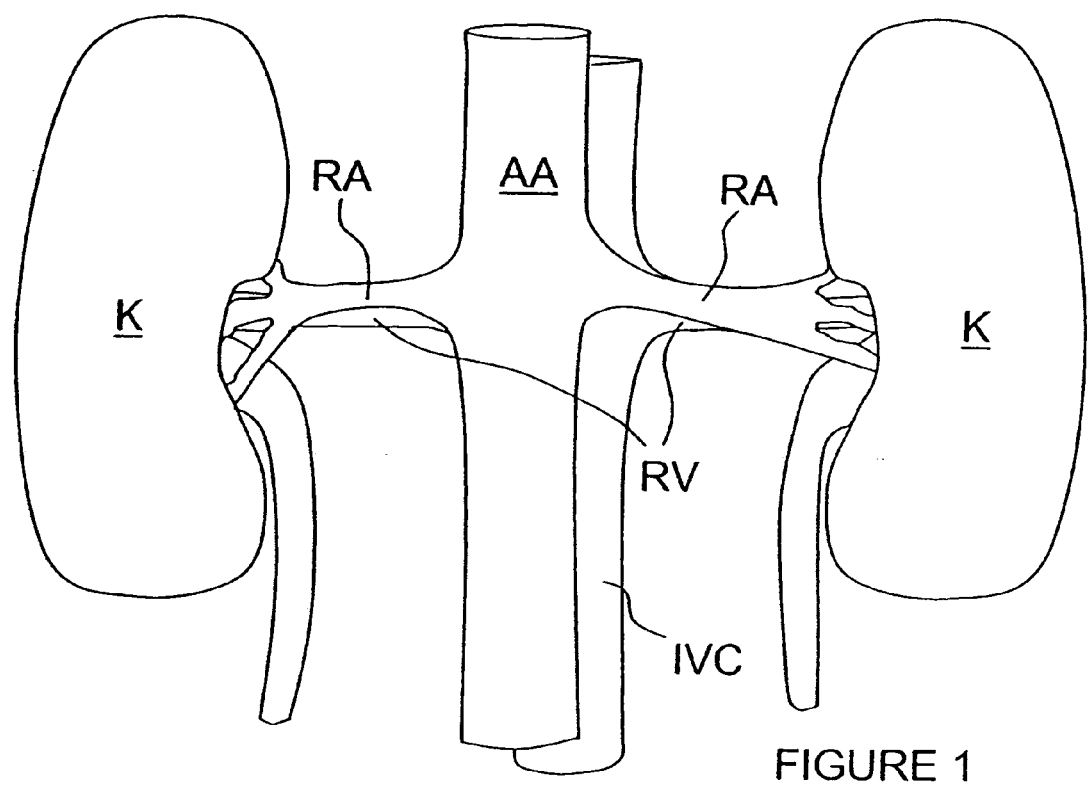
FIG. 1 is a schematic view illustrating human renal anatomy.
Figure 2:
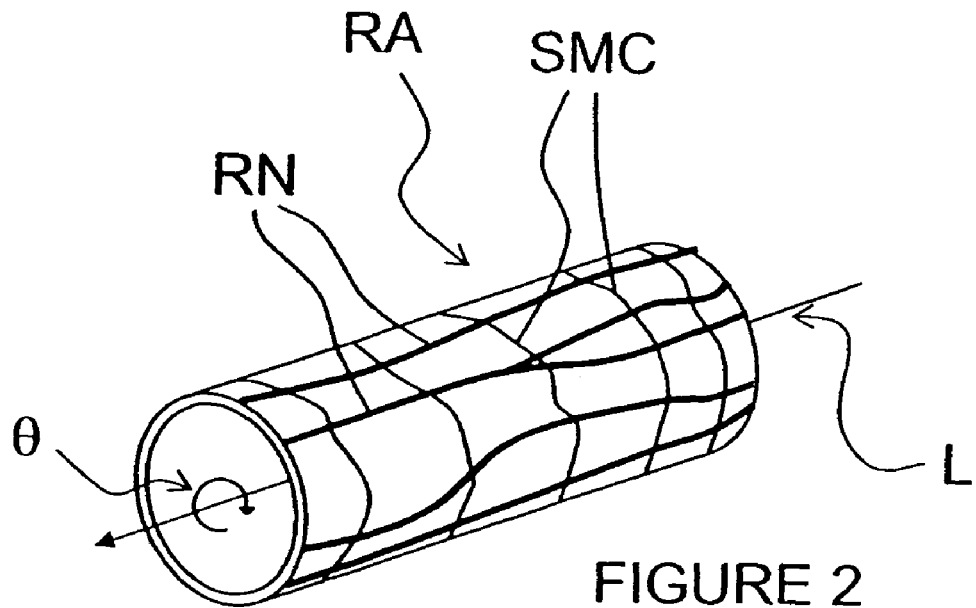
FIG. 2 is a schematic detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
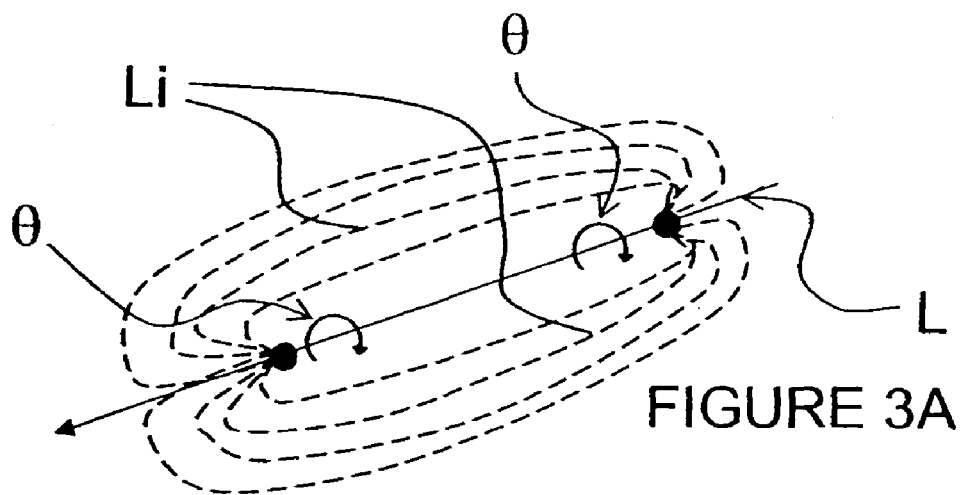
FIGS. 3A and 3B are schematic side- and end-views, respectively, illustrating orienting of electrical current flow for selectively affecting renal nerves.
Figure 3B:
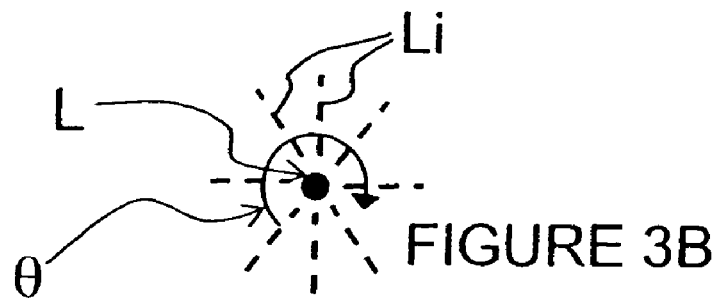

Referring to FIG. 3, the cellular misalignment of the renal nerves and the smooth muscle cells may be exploited to selectively affect renal nerve cells with reduced effect on smooth muscle cells. More specifically, because larger cells require less energy to exceed the irreversibility threshold of electroporation, several embodiments of electrodes of the present invention are configured to align at least a portion of an electric field generated by the electrodes with or near the longer dimensions of the cells to be affected. In specific embodiments, the device has electrodes configured to create an electrical field aligned with or near the lengthwise dimension L of the renal artery RA to affect renal nerves RN. By aligning an electric field so that the field preferentially aligns with the lengthwise aspect of the cell rather than the diametric or radial aspect of the cell, lower field strengths may be used to affect target neural cells, e.g., to necrose or fuse the target cells and/or to induce apoptosis. As mentioned above, this is expected to reduce power consumption and mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning the PEF with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIG. 3, applying a PEF with propagation lines Li generally aligned with the longitudinal dimension L of the renal artery RA is expected to preferentially cause electroporation, electrofusion, denervation or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment θ through a range of 0°-360°.

A PEF system placed exterior to, within, and/or at least partially across the wall of the renal artery may propagate an electric field having a longitudinal portion that is aligned to run with the longitudinal dimension of the artery in the region of the renal nerves RN and the smooth muscle cell SMC of the vessel wall so that the wall of the artery remains at least substantially intact while the outer nerve cells are destroyed or fused. Monitoring elements may be utilized to assess an extent of, e.g., electroporation, induced in renal nerves and/or in smooth muscle cells, as well as to adjust PEF parameters to achieve a desired effect.

Figure 4:
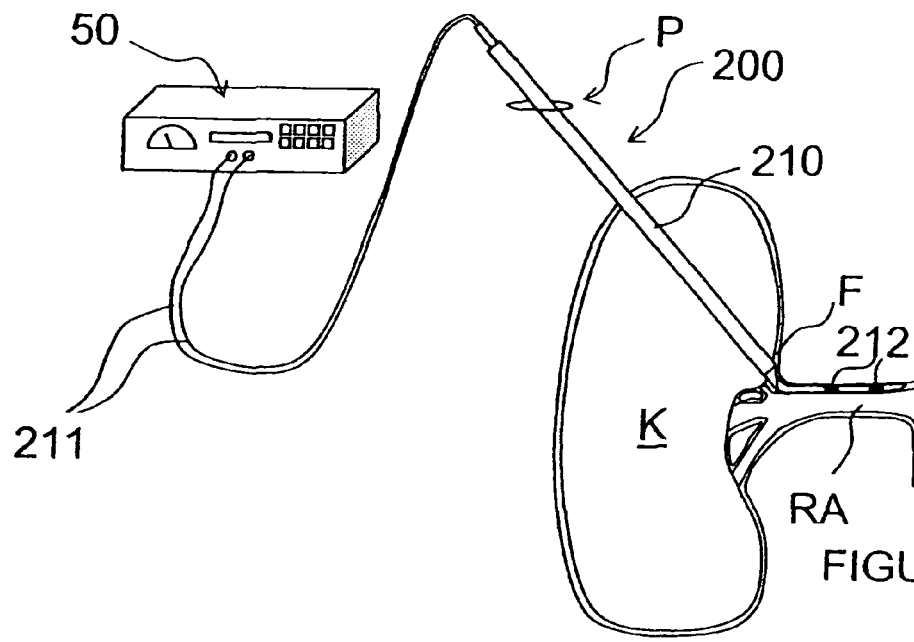
FIG. 4 is a schematic view illustrating an exemplary extravascular method and apparatus for renal neuromodulation.

C. Exemplary Embodiments of Systems and Additional Methods for Neuromodulation With reference to FIGS. 4 and 5, exemplary embodiments of PEF systems and methods are described. FIG. 4 shows one embodiment of an extravascular pulsed electric field apparatus 200 that includes one or more electrodes configured to deliver a pulsed electric field to renal neural fibers to achieve renal neuromodulation. The apparatus of FIG. 4 is configured for temporary extravascular placement; however, it should be understood that partially or completely implantable extravascular apparatus additionally or alternatively may be utilized.

In FIG. 4, apparatus 200 comprises a laparoscopic or percutaneous PEF system having probe 210 configured for insertion in proximity to the track of the renal neural supply along the renal artery or vein or hilum and/or within Gerota's fascia under, e.g., CT or radiographic guidance. At least one electrode 212 is configured for delivery through probe 210 to a treatment site for delivery of pulsed electric field therapy. The electrode(s) 212 may comprise a catheter and are electrically coupled to pulse generator 50 via wires 211. In an alternative embodiment, the distal section of probe 210 may comprise the at least one electrode 212, and the probe may have an electrical connector to couple the probe to the pulse generator 50 for delivering a PEF to the electrode(s) 212.

The pulsed electric field generator 50 is located external to the patient. The generator, as well as any of the PEF-delivery electrode embodiments described herein, may be utilized with any embodiment of the present invention for delivery of a PEF with desired field parameters. It should be understood that PEF-delivery electrodes of embodiments described hereinafter may be electronically connected to the generator even though the generator is not explicitly shown or described with each embodiment.

The electrode(s) 212 can be individual electrodes that are electrically independent of each other, a segmented electrode with commonly connected contacts, or a continuous electrode. A segmented electrode may, for example, be formed by providing a slotted tube fitted onto the electrode, or by electrically connecting a series of individual electrodes. Individual electrodes or groups of electrodes 212 may be configured to provide a bipolar signal. The electrodes 212 may be dynamically assignable to facilitate monopolar and/or bipolar energy delivery between any of the electrodes and/or between any of the electrodes and an external ground pad. Such a ground pad may, for example, be attached externally to the patient's skin, e.g., to the patient's leg or flank. In FIG. 4, the electrodes 212 comprise a bipolar electrode pair. The probe 210 and the electrodes 212 may be similar to the standard needle or trocar-type used clinically for pulsed RF nerve block, such as those sold by Valleylab (a division of Tyco Healthcare Group LP) of Boulder, Colo. Alternatively, the apparatus 200 may comprise a flexible and/or custom-designed probe for the renal application described herein.

In FIG. 4, the percutaneous probe 210 has been advanced through percutaneous access site P into proximity with renal artery RA. The probe pierces Gerota's fascia F, and the electrodes 212 are advanced into position through the probe and along the annular space between the patient's artery and fascia. Once properly positioned, pulsed electric field therapy may be applied to target neural fibers across the bipolar electrodes 212. Such PEF therapy may, for example, denervate the target neural fibers through irreversible electroporation. Electrodes 212 optionally also may be used to monitor the electroporative effects of the PEF therapy, as described hereinbelow. After treatment, the apparatus 200 may be removed from the patient to conclude the procedure.

Figure 5:
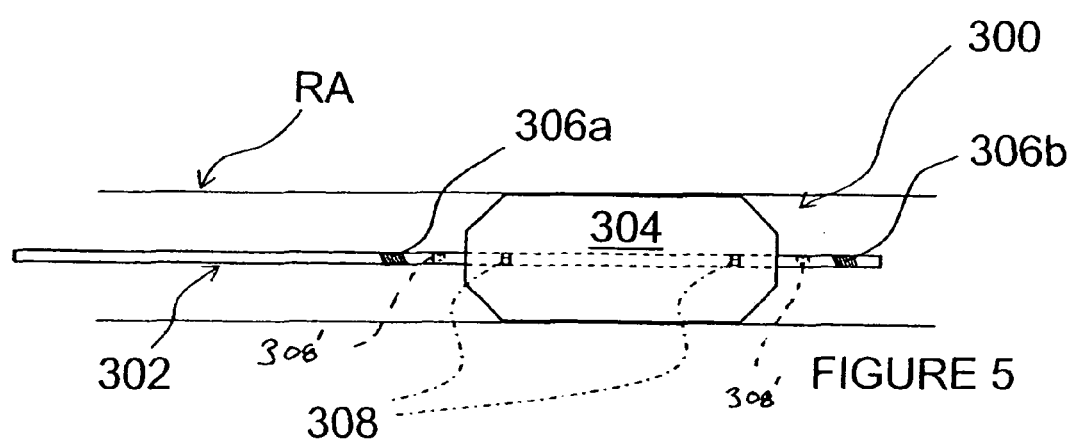
FIG. 5 is a schematic view illustrating an exemplary intravascular method and apparatus for renal neuromodulation.

Referring now to FIG. 5, another embodiment of an intravascular PEF system is described. This embodiment includes an apparatus 300 comprising a catheter 302 having a centering element 304 (e.g., a balloon, an expandable wire basket, other mechanical expanders, etc.), shaft electrodes 306a and 306b disposed along the shaft of the catheter, and optional radiopaque markers 308 disposed along the shaft of the catheter in the region of the centering element 304. The electrodes 306a-b, for example, can be arranged such that the electrode 306a is near a proximal end of the centering element 304 and the electrode 306b is near the distal end of the centering element 304. Electrodes 306 are electrically coupled to pulse generator 50 (see FIG. 4), which is disposed external to the patient, for delivery of PEF therapy. The radiopaque markers can alternatively be located along the shaft outside of the centering element 304 as shown by optional markers 308', or the electrodes can be made from a radiopaque material (e.g., platinum) to eliminate the separate markers 308.

Electrodes 306 can be individual electrodes (i.e., independent contacts), a segmented electrode with commonly connected contacts, or a single continuous electrode. Furthermore, electrodes 306 may be configured to provide a bipolar signal, or electrodes 306 may be used together or individually in conjunction with a separate patient ground for monopolar use. When centering element 304 comprises an inflatable balloon, the balloon may serve as both a centering element for electrodes 306 and as an electrical insulator for directing an electric field delivered across the electrodes, e.g., for directing the electric field into or across the vessel wall for modulation of target neural fibers. Electrical insulation provided by element 304 may reduce the magnitude of applied voltage or other parameters of the pulsed electric field necessary to achieve desired field strength at the target tissue.

As an alternative or in addition to placement of electrodes 306 along the central shaft of catheter 302, electrodes 306 may be attached to centering element 304 such that they contact the wall of renal artery RA (e.g., surface contact and/or penetration). In such a variation, the electrodes may, for example, be affixed to the inside surface, outside surface or at least partially embedded within the wall of the centering element. The electrodes optionally may be used to monitor the effects of PEF therapy, as described hereinafter. As it may be desirable to reduce or minimize physical contact between the PEF-delivery electrodes and the vessel wall during delivery of PEF therapy in order to reduce the potential for injuring the wall. The electrodes 306 may, for example, be a first set of electrodes attached to the shaft of the catheter for delivering the PEF therapy, and the device may further include a second set of electrodes optionally attached to centering element 304 for monitoring the effects of PEF therapy delivered via electrodes 306, as discussed hereinbelow with respect to FIG. 7.

In use, catheter 302 may be delivered to renal artery RA as shown, or it may be delivered to a renal vein or to any other vessel in proximity to neural tissue contributing to renal function, in a low profile delivery configuration, for example, through a guide catheter. Once positioned within the renal vasculature, optional centering element 304 may be expanded into contact with an interior wall of the vessel. A pulsed electric field then may be generated by the PEF generator 50, transferred through catheter 302 to electrodes 306, and delivered via the electrodes 306 across the wall of the artery. The PEF therapy modulates the activity along neural fibers that contribute to renal function, e.g., denervates the neural fibers. This may be achieved, for example, via irreversible electroporation, electrofusion and/or inducement of apoptosis in the nerve cells. In many applications, the electrodes are arranged so that the pulsed electric field is aligned with the longitudinal dimension of the renal artery to facilitate modulation of renal nerves with little effect on non-target smooth muscle cells or other cells.

It is expected that PEF therapy, whether delivered extravascularly, intravascularly, transvascularly or a combination thereof, will alleviate clinical symptoms of CHF, hypertension, renal disease and/or other cardio-renal diseases for a period of months, potentially up to six months or more. This time period might be sufficient to allow the body to heal; for example, this period might reduce the risk of CHF onset after an acute myocardial infarction, thereby alleviating a need for subsequent re-treatment. Alternatively, as symptoms reoccur, or at regularly scheduled intervals, the patient might return to the physician for a repeat therapy.

The apparatus described above with respect to FIGS. 4 and 5 may be used to quantify the efficacy, extent, or cell selectivity of PEF therapy to monitor and/or control the therapy. When a pulsed electric field initiates electroporation, the impedance of the electroporated tissue begins to decrease and the conductivity of the tissue begins to increase. If the electroporation is reversible, the tissue electrical parameters will return or approximate baseline values upon cessation of the PEF. However, if the electroporation is irreversible, the changes in tissue parameters will persist after termination of the PEF. These phenomena may be utilized to monitor both the onset and the effects of PEF therapy. For example, electroporation may be monitored directly using, for example, conductivity measurements or impedance measurements, such as Electrical Impedance Tomography ("EIT") and/or other electrical impedance/conductivity measurements like an electrical impedance or conductivity index. Such electroporation monitoring data may be used in one or more feedback loops to better control delivery of PEF therapy.

For the purposes of the present invention, the imaginary part of impedance is ignored and impedance is defined as voltage divided by current, while conductance is defined as the inverse of impedance (i.e., current divided by voltage), and conductivity is defined as conductance per unit distance.

The distance between monitoring electrodes preferably is known prior to therapy delivery and may be used to determine conductivity from impedance or conductance measurements.

Figure 6:
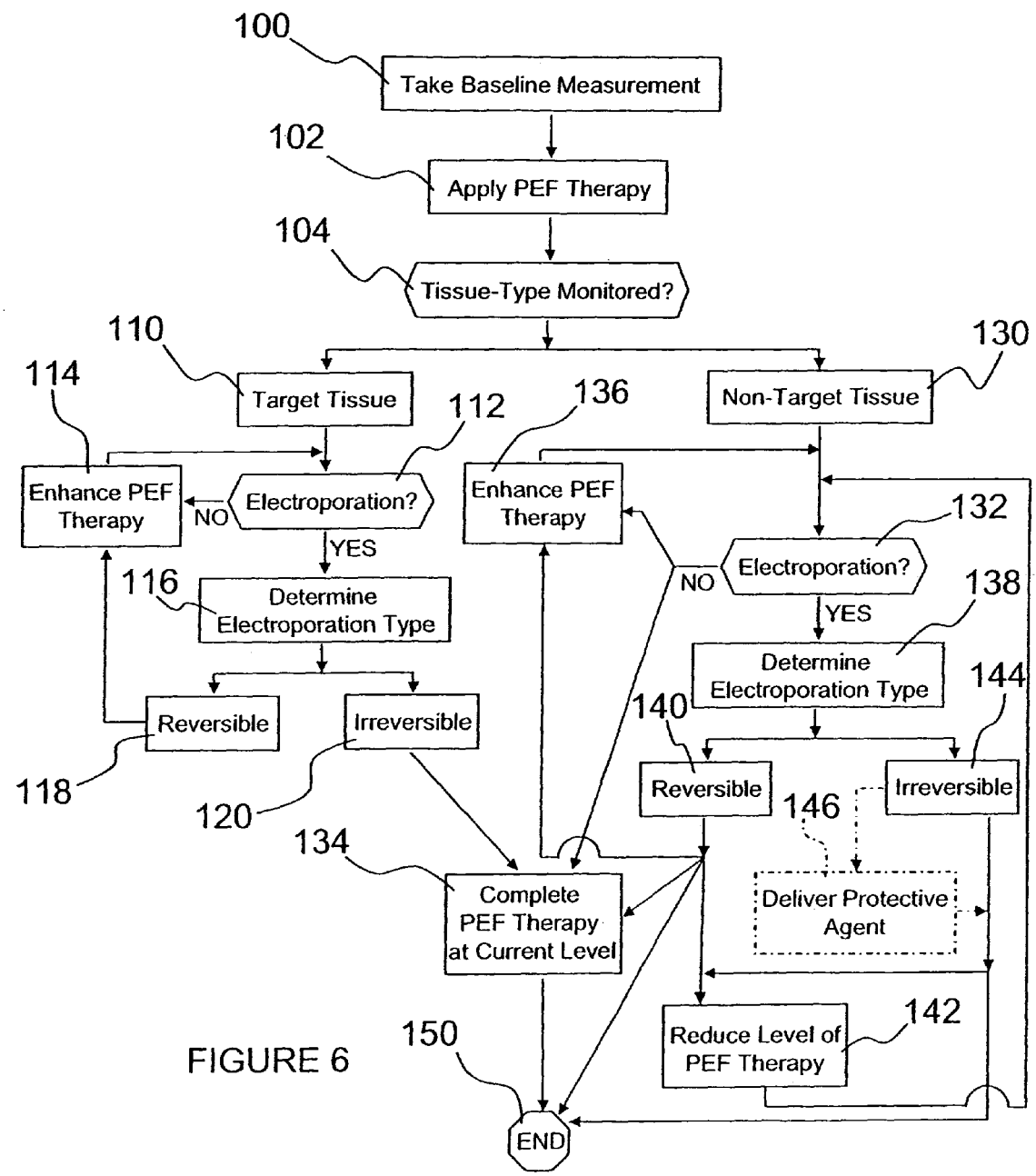
FIG. 6 is a schematic flowchart illustrating methods of controlling pulsed electric field renal neuromodulation in response to electroporation monitoring feedback.

FIG. 6 provides a schematic flowchart illustrating methods of controlling pulsed electric field renal neuromodulation in response to electroporation monitoring feedback. These methods may be utilized intravascularly, extravascularly, transvascularly or a combination thereof. In FIG. 6, Step 100 comprises taking a baseline measurement of impedance and/or conductivity for the tissue being monitored, e.g., by emitting a low voltage pulse through the tissue (for example, a voltage less than about 20 volts) and measuring the response. This baseline may be utilized as a reference against which changes in impedance or conductivity may be compared upon application of a pulsed electric field to the tissue being monitored. As discussed previously, electroporation of tissue causes tissue impedance to decrease and causes tissue conductivity to increase.

With the baseline established, Step 102 comprises applying PEF therapy in the vicinity of the tissue being monitored. As seen in Step 104, the desired response of monitored tissue to such therapy depends upon whether the tissue being monitored is the target tissue of Routine 110 or the non-target tissue of Routine 130. Generally, it is desirable to electroporate or irreversibly electroporate the target tissue of Routine 110, while it may be undesirable to electroporate or irreversibly electroporate the non-target tissue of Routine 130. The target tissue of Routine 110 may comprise, for example, neural fibers that contribute to renal function, while the non-target tissue of Routine 130 may comprise, for example, the interior or exterior wall of renal vasculature and/or of smooth muscle cells.

Monitoring elements preferably are in physical contact or in close proximity with the tissue being monitored. For example, non-target tissue may be monitored intravascularly or extravascularly; i.e., within, or exterior and in close proximity to, renal vasculature. Target tissue may, for example, be monitored extravascularly or may be monitored transvascularly, for example, by placing monitoring elements in the vascular adventitia. Other alternative monitoring arrangements may be provided.

For the target tissue of Routine 110, after application of PEF therapy during Step 102, Step 112 comprises monitoring the impedance and/or conductivity of the target tissue, e.g., emitting a low voltage pulse through the tissue and measuring the response, to determine whether the tissue has been electroporated. As mentioned, electroporation increases tissue conductivity and decreases tissue impedance. If the tissue has not been electroporated, then PEF therapy should be enhanced, as in Step 114. PEF enhancement comprises increasing the strength, intensity, duration, positioning, etc., of any of the parameters of the pulsed electric field that contribute to inducement of tissue electroporation. Additionally, PEF can be enhanced by providing agents that impart beneficial properties to the tissue (e.g., conductivity). Suitable agents include saline, hypertonic saline, and other compounds.

If the target tissue has been electroporated, Step 116 comprises determining what type of electroporation has occurred, i.e. reversible electroporation of Step 118 or irreversible electroporation of Step 120. For example, an absolute or a threshold relative change in tissue impedance or conductivity from the baseline measurement taken in Step 100 may be indicative of the type of electroporation. Additionally or alternatively, the persistence of changes in monitored electrical parameters after cessation of PEF therapy may be used to determine electroporation type. For example, changes in impedance or conductivity that persist after termination of the PEF are indicative of the irreversible electroporation of Step 120; conversely, a return of impedance or conductivity to or approximate the baseline value obtained during Step 100 is indicative of the reversible electroporation of Step 118.

For target tissue, if it is determined that induced electroporation is reversible, then PEF therapy should be enhanced, as in the feedback loop of Step 114, until irreversible electroporation is achieved. Likewise, if it is determined that the electroporation is irreversible, then the procedure may be completed at its current level, as in Step 134, then concluded in Step 150.

If the tissue being monitored is the non-target tissue of Routine 130, Step 132 comprises determining whether the PEF therapy of Step 102 has induced or is presently inducing electroporation in the non-target tissue. This may be achieved by monitoring the impedance or conductivity of the non-target tissue of Routine 130, e.g., by emitting a low voltage pulse through the tissue and measuring the response, and comparing measured values to the baseline measurement of Step 100. Measurements preferably are taken and analyzed in real time.

As discussed, electroporation, and especially irreversible electroporation, generally is not desirable in non-target tissue. However, reversible electroporation and/or a limited amount of irreversible electroporation of non-target tissue may be acceptable in order to irreversibly electroporate the target tissue. The potential for undesirably injuring the non-target tissue should be weighed against the expected benefits of irreversibly electroporating the target tissue.

If it is determined that electroporation of the non-target tissue has not occurred, then the medical practitioner (or, alternatively, the system in an automatic feedback loop via pre-programmed instructions) has a few options. The practitioner may complete PEF therapy at the current electrical parameters without altering the position of the PEF system and apparatus, as in Step 134. This may be desirable, for example, if the PEF therapy is of sufficient magnitude and is delivered in a manner sufficient to initiate irreversible electroporation in target tissue without electroporating the non-target tissue. After completion of the PEF therapy, the procedure may be concluded, as in Step 150.

The practitioner alternatively may enhance the PEF therapy, as in the feedback loop of Step 136. This may be desirable, for example, if the PEF therapy is insufficient to initiate irreversible electroporation in the target tissue, as determined, for example, via (a) optional concurrent monitoring of target tissue, (b) predictions from modeling simulations, (c) statistical reference to previously conducted PEF therapy with similar waveform parameters, etc. After enhancement of the PEF therapy, Step 132 may be repeated to determine whether the enhanced PEF therapy induces electroporation in the non-target tissue of Routine 130.

If, Step 132 establishes that PEF therapy has induced electroporation in the non-target tissue (either at the initial PEF therapy levels of Step 102 or after enhancement of the PEF therapy via Step 136), then Step 138 comprises determining the type of electroporation that has occurred. Step 138, for example, can utilize the techniques described previously with respect to target tissue monitoring. If it is determined that the electroporation comprises the reversible electroporation of Step 140, then the medical practitioner or an automated control system has four options. The first option is to immediately terminate PEF therapy, as in Step 150. This is the most conservative course of action for reducing potential injury to the non-target tissue monitored in Step 130. However, this may not be sufficient to achieve a desired level of, e.g., irreversible electroporation in the target tissue of Step 110.

Another option is to proceed to the feedback loop of Step 142, which comprises reducing the level or magnitude of the PEF therapy along non-target tissue. This may comprise repositioning elements of the PEF system and/or altering electrical parameters of the pulsed electric field. Reducing the magnitude of the PEF therapy may be sufficient to reduce or stop electroporation of the non-target tissue. However, reductions in the magnitude of the therapy should be weighed against the effect of the reductions on desired electroporation of target tissue. Overly aggressive reduction in the pulsed electric field may negate the field's ability to advantageously electroporate the target tissue of Step 110.

Alternatively, PEF therapy may be completed at the then-current levels or magnitude, as in Step 134. If the monitored electrical parameters indicate that electroporation of the non-target tissue is reversible, then the potential for sustained injury to the non-target tissue of Step 130 associated with continuing the PEF therapy may be relatively low and may support continued therapy at the then-current levels, as needed, to achieve desired effects on the target tissue of Step 110. However, continuation of the PEF therapy should be weighed against the potential for non-target tissue injury. After completion of PEF therapy under Step 134, the procedure may be concluded in Step 150.

Another alternative is to enhance the magnitude of PEF therapy, as in the feedback loop of Step 136, then repeat the electroporation monitoring and decision process to ensure that the new level of PEF therapy still has an acceptably low potential for inducing sustained injury in the non-target tissue. It may, for example, be desirable to enhance PEF therapy until a therapy level sufficient to induce irreversible electroporation in the target tissue of Step 110 is achieved. Alternatively or additionally, PEF therapy may be enhanced until the non-target tissue of Step 130 is reversibly electroporated and/or until the monitored parameter(s) of the non-target tissue are altered by a threshold amount, e.g., until a threshold change in tissue impedance is observed.

The PEF therapy optionally may be progressively and gradually ramped up from a low level to the desired level while monitoring non-target tissue in order to reduce the potential for sustained injury to the non-target tissue. Ramping of the PEF therapy may be discontinued or reversed at any time, for example, when the potential for sustained injury to the non-target tissue outweighs the potential benefits of therapy at a given level of PEF magnitude. Additional PEF waveforms, as well as techniques for altering the waveforms in response to monitoring data, are described hereinafter.

If it is determined that electroporation of the non-target tissue of Step 130 comprises undesirable irreversible electroporation, as in Step 144, then the medical practitioner or automated control system (e.g., auto-feedback loop) may reduce the level of PEF therapy, preferably to a level that does not continue to irreversibly electroporate the non-target tissue, as in the feedback loop of Step 142. Alternatively, the medical practitioner or automated control system may halt PEF therapy and conclude the procedure, as in Step 150. In some embodiments, such reduction or termination of PEF therapy may be implemented automatically by the PEF system whenever irreversible electroporation of non-target tissue is observed. The medical practitioner optionally might deliver, e.g., inject, a protective agent, such as Poloxamer-188, to irreversibly electroporated non-target tissue in order to reduce the potential for, or the degree of, sustained injury to the non-target tissue, as in Step 146.

Figure 7:
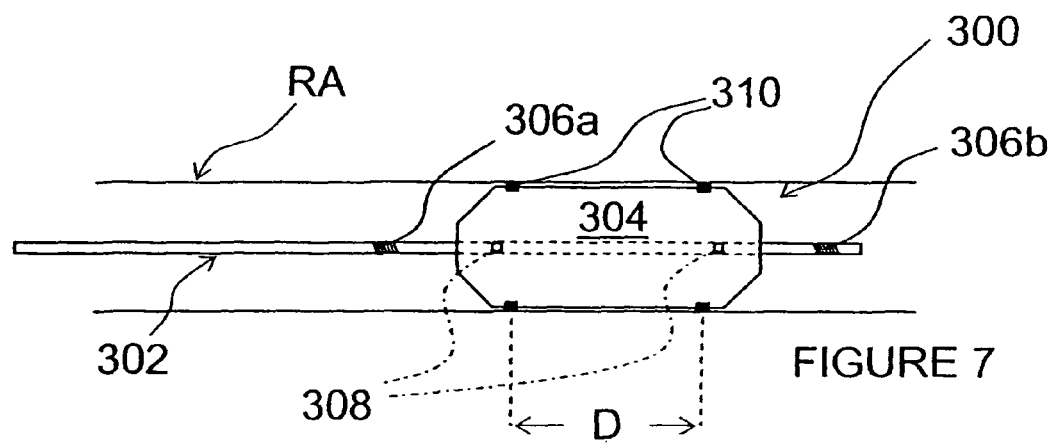
FIG. 7 is a side view, partially in section, of an alternative embodiment of the intravascular apparatus of FIG. 5 having independent monitoring elements, illustrating a method of monitoring and controlling PEF therapy at a target site within a patient's blood vessel.

With reference now to FIG. 7, an alternative embodiment of previously-described apparatus 300 comprising monitoring elements is described. In FIG. 7, apparatus 300 comprises monitoring electrodes 310 coupled to centering element 304. Monitoring electrodes 310 may be utilized to monitor the effects of PEF therapy delivered via electrodes 306, e.g., by emitting a low voltage pulse across monitoring electrodes 310 and through the monitored tissue, and then measuring the impedance or conductivity of the monitored tissue. The separation distance D between the monitoring electrodes 310 preferably is known in order to facilitate determination of tissue conductivity (conductance per unit distance) from tissue conductance or impedance measurements. Electrodes 310 optionally may be electrically coupled to pulse generator 50, for example, in a feedback loop, and/or may be electrically coupled to other external element(s) for emitting the low voltage monitoring pulse, or for recording, displaying and/or processing monitoring data collected via the electrodes. Although the apparatus 300 shown in FIG. 7 comprises separate electrode pairs for PEF therapy delivery and for monitoring of PEF effects, the same electrodes alternatively may be used both for delivery of PEF therapy and for monitoring of the effects of such therapy.

In use, electrodes 310 directly contact the vessel wall, as seen in FIG. 7. A baseline conductivity or impedance measurement may be made to determine steady-state tissue parameters prior to PEF therapy, e.g., by emitting a low voltage pulse across the monitoring electrodes and through the tissue, and then measuring the response of the monitored tissue. Once the baseline has been established, a pulse train may be applied to the tissue via bipolar electrode pair 306 to cause electroporation, and the effects of such electroporation may be monitored via monitoring electrodes 310, e.g., by applying another low voltage pulse across the electrodes 310 and examining changes in tissue impedance or conductivity from the baseline values.

The time between each PEF pulse, or after two or more PEF pulses, optionally may be sufficient to assess the status of the electroporative effect on the vessel wall via the monitoring electrodes. Monitoring alternatively or additionally may be conducted before and after application of PEF therapy to ensure the desired effect. To prevent circuit disruption, monitoring electrodes 310 optionally may be electrically disconnected during activation of PEF-delivery electrodes 306.

In some embodiments, it may be desirable to avoid irreversible electroporation of the vessel wall. In such an embodiment, PEF therapy may be interrupted should a target level of impedance decrease or conductivity increase occur at the vessel wall. This would provide a feedback system to ensure that non-target cells are not irreversibly electroporated during irreversible electroporation of target cells, such as nerve cells that contribute to renal function.

Additionally or alternatively, a treatment algorithm may be employed wherein the PEF pulse train starts out with a relatively small field strength [voltage/unit distance] that gradually increases based upon monitoring feedback. For example, the treatment may be initiated with relatively small field strength, $E_1$, delivered by electrodes 306. If monitoring data collected via monitoring electrodes 310 indicates that the application of $E_1$ does not alter the impedance or conductivity of the vessel wall, it is unlikely that electroporation has been initiated in the vessel wall. Thus, the field strength may be increased to $E_2$, etc., until electroporation is initiated. As electroporation is initiated, the impedance decreases and the conductivity increases, but these parameters should recover their baselines values once the field is no longer applied. If this recovery occurs, electroporation was reversible and an even larger field, $E_3$, optionally may be applied. Alternatively, a percent change or an absolute change in tissue impedance or conductivity may be used which predicts the outcome of reversible or irreversible electroporation. This monitoring technique may be used to prevent or reduce unwanted injury to the vessel wall. The flowchart of FIG. 6 may be used as a decision tree to guide delivery of the ramping pulsed electric field.

Figure 8A:
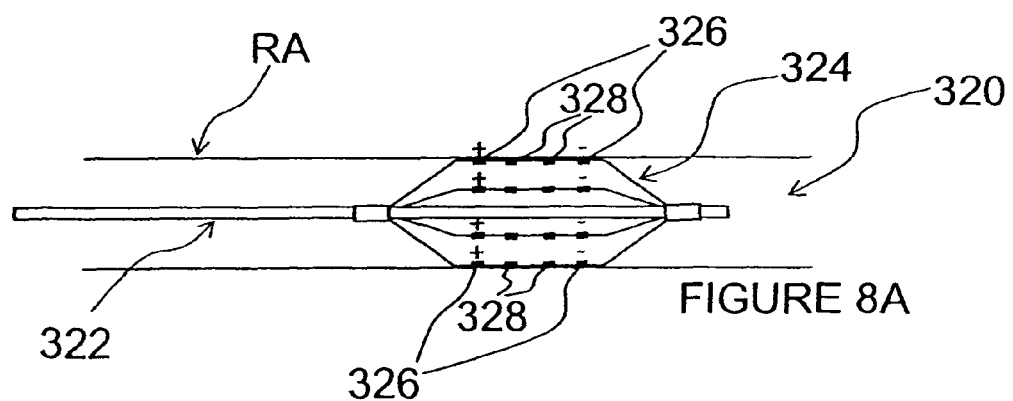
FIGS. 8A and 8B are schematic side views of embodiments of a catheter with a centering element having both monitoring electrodes and PEF-delivery electrodes.
Figure 8B:
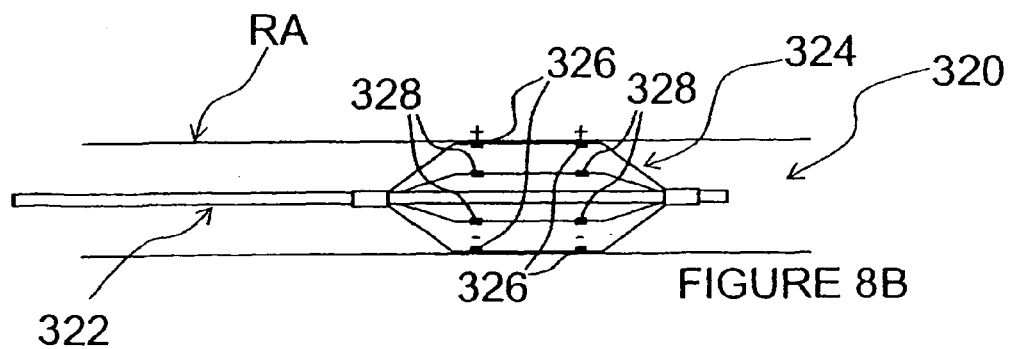

With reference now to FIG. 8, an alternative apparatus 320 for delivering and monitoring PEF therapy is described. Apparatus 320 comprises intravascular catheter 322 having centering element 324 with PEF-delivery electrodes 326 and monitoring electrodes 328. Centering element 324 may, for example, comprise a balloon or an expandable basket. FIG. 8A illustrates an embodiment wherein the source and sink of the PEF-delivery electrodes 326 and the electrode pairs of the monitoring electrodes 328 are separated from one another along the longitudinal axis of centering element 324, and FIG. 8B illustrates an embodiment wherein the electrode pairs are separated from one another along the radial axis of the centering element. As will be apparent, the source and sink of the PEF-delivery electrodes, and/or the electrodes of the monitoring electrode pairs, may be separated from one another along both the longitudinal and the radial axis of the centering element. As also will be apparent, the electrodes alternatively may be utilized in an extravascular or transvascular embodiment of the present invention; for example, the electrodes may be integrated into an external cuff electrode.

In FIGS. 8A and 8B, apparatus 320 comprises a plurality of PEF-delivery electrodes and a plurality of monitoring electrodes. In such a configuration, a multiplexer may be used to deliver PEF therapy across a desired pair or plurality of PEF-delivery electrodes 326; likewise, a multiplexer may be utilized to deliver the low voltage signal and facilitate conductivity or impedance measurements across a desired pair or plurality of monitoring electrodes 328. A matrix of PEF therapy and/or monitoring configurations may be used to facilitate PEF delivery or monitoring as desired. Such a multiplexer may be used to deliver PEF therapy with other embodiments of apparatus set forth herein.

Figure 9:
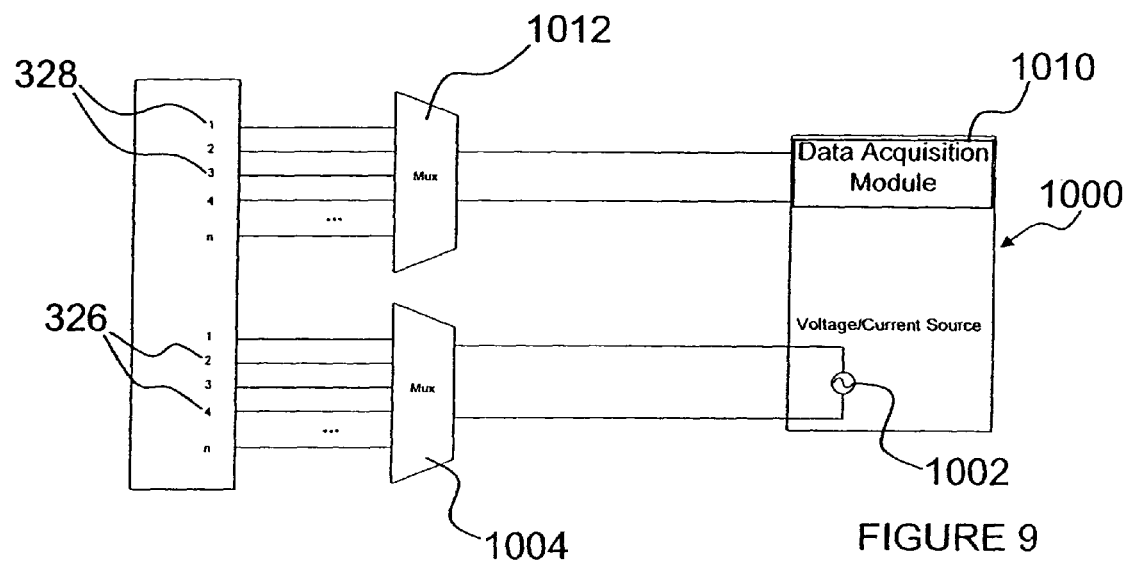
FIG. 9 is a schematic view of an exemplary circuit diagram for a PEF system comprising PEF-delivery electrodes and monitoring electrodes.

FIG. 9 illustrates an embodiment of a circuit diagram for such a multiplexed configuration. External control apparatus 1000, which may, for example, comprise an embodiment of pulse generator 50 described previously, a computer, a data acquisition module, etc., comprises voltage or current source 1002 coupled to multiplexer 1004. The multiplexer routes PEF waveforms generated by source 1002 to desired PEF-delivery electrodes 326. Apparatus 1000 further comprises data acquisition module 1010 coupled to multiplexer 1012, which delivers the low voltage signal, then measures and monitors data from selected monitoring electrodes 328.

Multiplexed PEF therapy delivery and monitoring facilitates optional formation of a 3-dimensional conductivity or impedance map based on multiple electrode measurements. This map may be used to determine the type and/or extent of electroporation throughout the target region, rather than providing an average conductivity or impedance value indicative of overall tissue characteristics. Multiplexed therapy and monitoring may, for example, comprise switching through each PEF-delivery and/or monitoring electrode pair. Data acquisition module 1010 may measure the potential across all pairs, or a desired subset, of the monitoring electrodes.

In embodiments that monitor PEF therapy with the same electrodes that deliver the PEF, conductivity or impedance may be determined by measuring the current draw across the electrodes under a voltage source, or by measuring the voltage applied under a constant current output. A differential potential measurement additionally or alternatively may be taken across the electrodes by delivering a low voltage signal before, during (e.g., between pulses) or after PEF delivery, as with the stand-alone monitoring electrodes.

Figure 10:
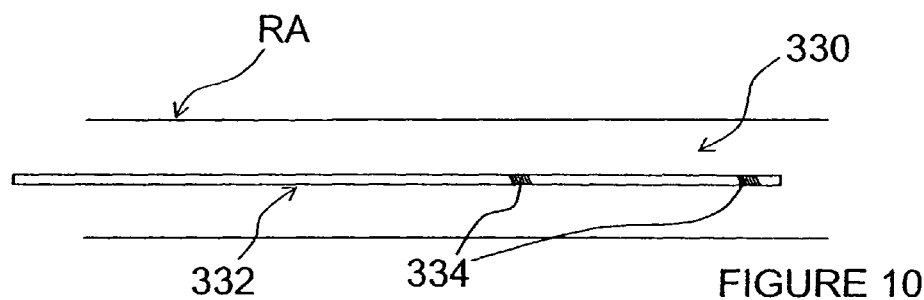
FIG. 10 is a side view, partially in section, of a catheter comprising combination monitoring and PEF-delivery electrodes.

Referring now to FIG. 10, another use for impedance or conductivity monitoring may be to ensure that intravascular electrodes used for applying a PEF pulse train do not come into direct contact with the vessel wall. In some indications, it may be desirable to position the PEF-delivery electrodes such that there is at least some spacing from the vessel wall, for example, to reduce a potential for injury to the vessel wall during PEF therapy. As seen in FIG. 10, apparatus 330 comprises catheter 332 having bipolar electrode pair 334 that may be used both for PEF therapy delivery and for monitoring of tissue parameters at a treatment site before, during or after PEF therapy.

Since the impedance of blood generally is lower than the impedance of the vessel wall, the observed impedance discontinuity between the blood and the wall may be used as a feedback mechanism to determine whether the electrodes are in contact with the vessel wall, i.e., to ensure proper positioning of the electrodes prior to or during delivery of PEF therapy. In FIG. 10, the catheter 332 is positioned such that electrodes 334 do not contact the wall of renal artery RA. Thus, impedance measurements across the electrodes are relatively low and indicate that the electrodes generally are not in contact with the vessel wall. If the electrodes were to contact the wall of the vessel before or during PEF therapy, the increased impedance levels would indicate such contact and optionally might immediately terminate or preclude PEF therapy until relatively lower impedance values are once again observed.

Figure 11:
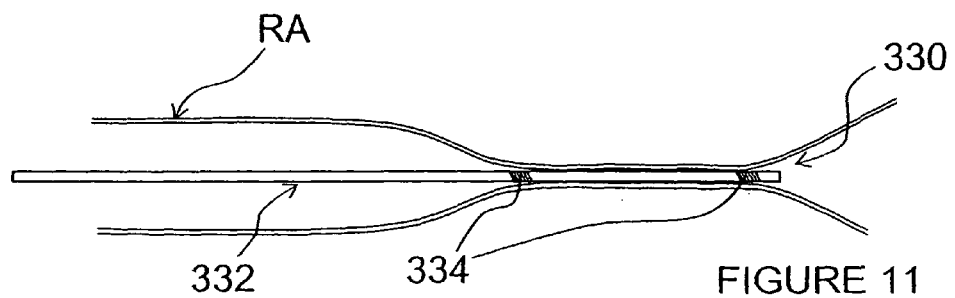
FIG. 11 is a side view, partially in section, illustrating a method of using the apparatus of FIG. 10 to reduce vessel trauma in the event of a vessel spasm.

As seen in FIG. 11, in some patients, PEF therapy might induce spasm in the vessel wall. If this were to occur, the vessel might prolapse against catheter 332. The increased impedance observed across electrodes 334 would indicate that the electrodes were in contact with the vessel wall. In response, PEF therapy could be terminated, either manually or automatically. Termination of the pulsed electric field might reduce injury to the vessel wall, as compared to continued delivery of PEF therapy.

Figure 12A:
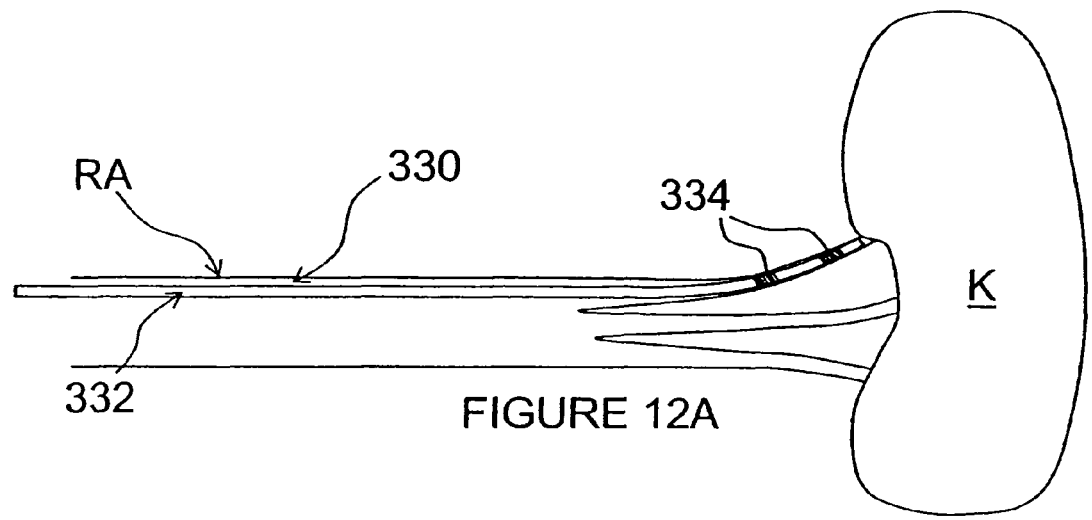
FIGS. 12A and 12B are side views, partially in section, illustrating a method of using the apparatus of FIG. 10 to ensure that the electrodes are not in contact with the vessel wall prior to, or during, PEF therapy.
Figure 12B:
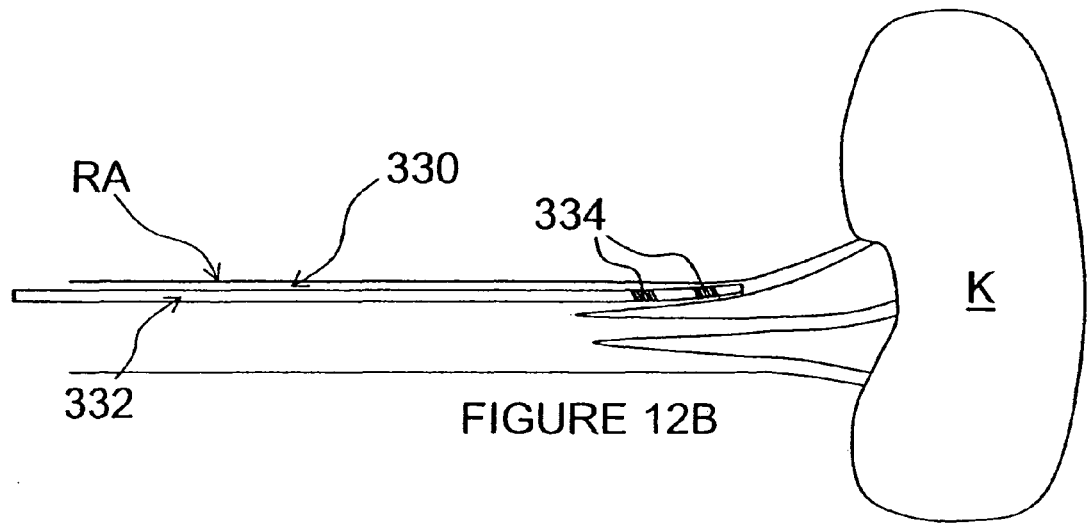

Referring now to FIG. 12, impedance measurements also may be used to ensure that catheter 332 isn't positioned in a vessel too small to accommodate electrodes 334 without the electrodes contacting the vessel wall. As seen in FIG. 12A, catheter 332 is disposed in a branch of renal artery RA that is too small to accommodate the electrodes. The increased impedance levels associated with contacting the vessel wall and observed across electrodes 334 would indicate to a medical practitioner that the catheter was not properly positioned for PEF therapy. In some embodiments, apparatus 330 may comprise features that preclude delivery of a pulsed electric field when electrodes 334 are in contact with the vessel wall. As seen in FIG. 12B, the catheter may be withdrawn to a more proximal position within the artery where the electrodes do not contact the vessel wall; the relatively low impedance levels observed across the electrodes when positioned as in FIG. 12B would indicate that PEF therapy could proceed.

Figure 13:
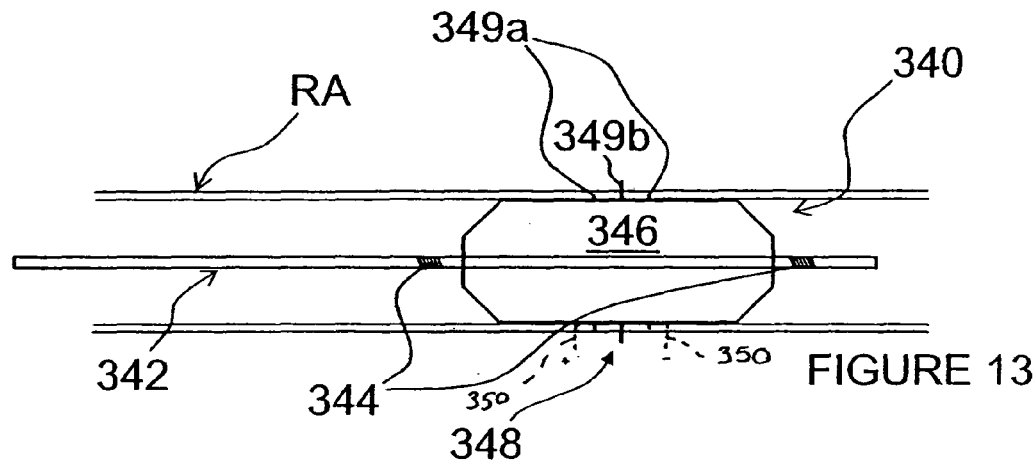
FIG. 13 is a side view, partially in section, of a PEF system illustrating a method for transvascular monitoring and control of PEF therapy.

With reference now to FIG. 13, it may be desirable to monitor electrical parameters within or external to the vessel wall, for example, within the adventitia of the vessel wall. Neural fibers that contribute to renal function may be positioned in or around the adventitia. Apparatus 340 of FIG. 13 is configured for intravascular delivery to a treatment site and for transvascular monitoring of PEF therapy. Apparatus 340 comprises catheter 342 having PEF-delivery electrodes 344 coupled to the shaft of catheter 342, as well as micro-puncture needle electrodes 348 coupled to expandable centering element 346.

Needle electrodes 348 may be configured to penetrate to various depths within a vessel wall for monitoring the impedance or conductivity of target or non-target tissue within or exterior to the wall, for example, for monitoring smooth muscle tissue of the vessel wall, for monitoring renal nerves in the adventitia, or for monitoring surrounding tissue, e.g., surrounding fat. The micro-puncture needle electrodes illustratively comprise non-target tissue monitoring electrodes 349a that are configured to penetrate within the vessel wall for monitoring of tissue within the wall, such as smooth muscle cells, as well as target tissue monitoring electrodes 349b that are configured to penetrate deeper into the vascular adventitia for monitoring of the neural fibers or tissue continuing neural fibers that contribute to renal function. In addition, or as an alternative, to their use in monitoring electrical characteristics of tissue, micro-puncture needles 348 may be used to inject agents transvascularly, such as protective agents, neurotoxins, PEF enhancing agents (e.g., saline or hypertonic saline), etc. Additional and alternative agents are described hereinbelow.

In use, catheter 342 is delivered to a treatment site, for example, within a patient's renal artery. The centering element 346 is expanded into contact with the wall of the vessel, which acts to center PEF-delivery electrodes 344 within the vessel, as well as to transvascularly position micro-puncture needle electrodes 348. Baseline measurements of impedance or conductivity are obtained via needle electrodes 348, i.e., for the non-target tissue with electrodes 349a and for the target tissue with electrodes 349b. PEF therapy then is delivered via electrodes 344, and the therapy is monitored and controlled via feedback data received from electrodes 348, for example, according to the guidelines of the flowchart of FIG. 6. As mentioned, agents additionally or alternatively may be injected through electrodes 348. After completion of the PEF therapy, balloon 346 is deflated (the centering element is collapsed), which removes the needle electrodes from the vessel wall, and catheter 342 is removed from the patient.

The apparatus 340 can further include electrodes/needles configured to deliver a PEF and/or agents to the target tissue in lieu of or in addition to monitoring the target tissue. For example, the apparatus can include additional electrodes or needles 350 that deliver the PEF and/or agents to the target tissue transvascularly. Alternatively, the electrodes 349b can be configured to deliver the PEF and/or agents transvascularly in addition to monitoring the tissue outside of the vessel.

Figure 14:
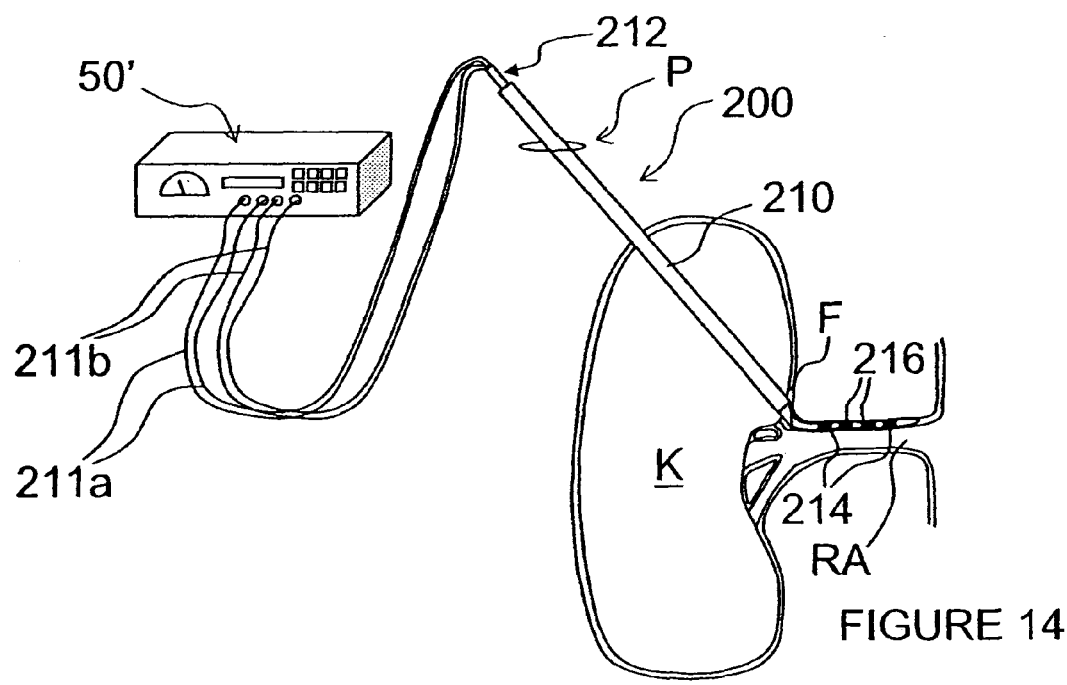
FIG. 14 is a side view, partially in section, of an alternative embodiment of the extravascular apparatus of FIG. 4 having independent monitoring elements, illustrating a method of extravascularly monitoring and controlling PEF therapy.

With reference now to FIG. 14, an alternative embodiment of the extravascular PEF system of FIG. 4 is described comprising monitoring elements. In FIG. 14, electrode catheter 212 comprises bipolar PEF-delivery electrodes 214 and monitoring electrodes 216, which also may be used in a bipolar fashion. The monitoring electrodes and the PEF-delivery electrodes are electrically coupled to modified pulse generator 50' by wires 211a and 211b, respectively. In use, PEF therapy is delivered via the PEF-delivery electrodes, and electroporation induced by the PEF therapy is monitored via the monitoring electrodes 216. The PEF therapy preferably is adjusted or controlled in response to the monitoring data received from electrodes 216. Modified pulse generator 50' is configured to deliver the PEF therapy across the PEF-delivery electrodes and to deliver low voltage signals across the monitoring electrodes, as well as to collect and analyze the monitoring data collected with the monitoring electrodes.

Figure 15:
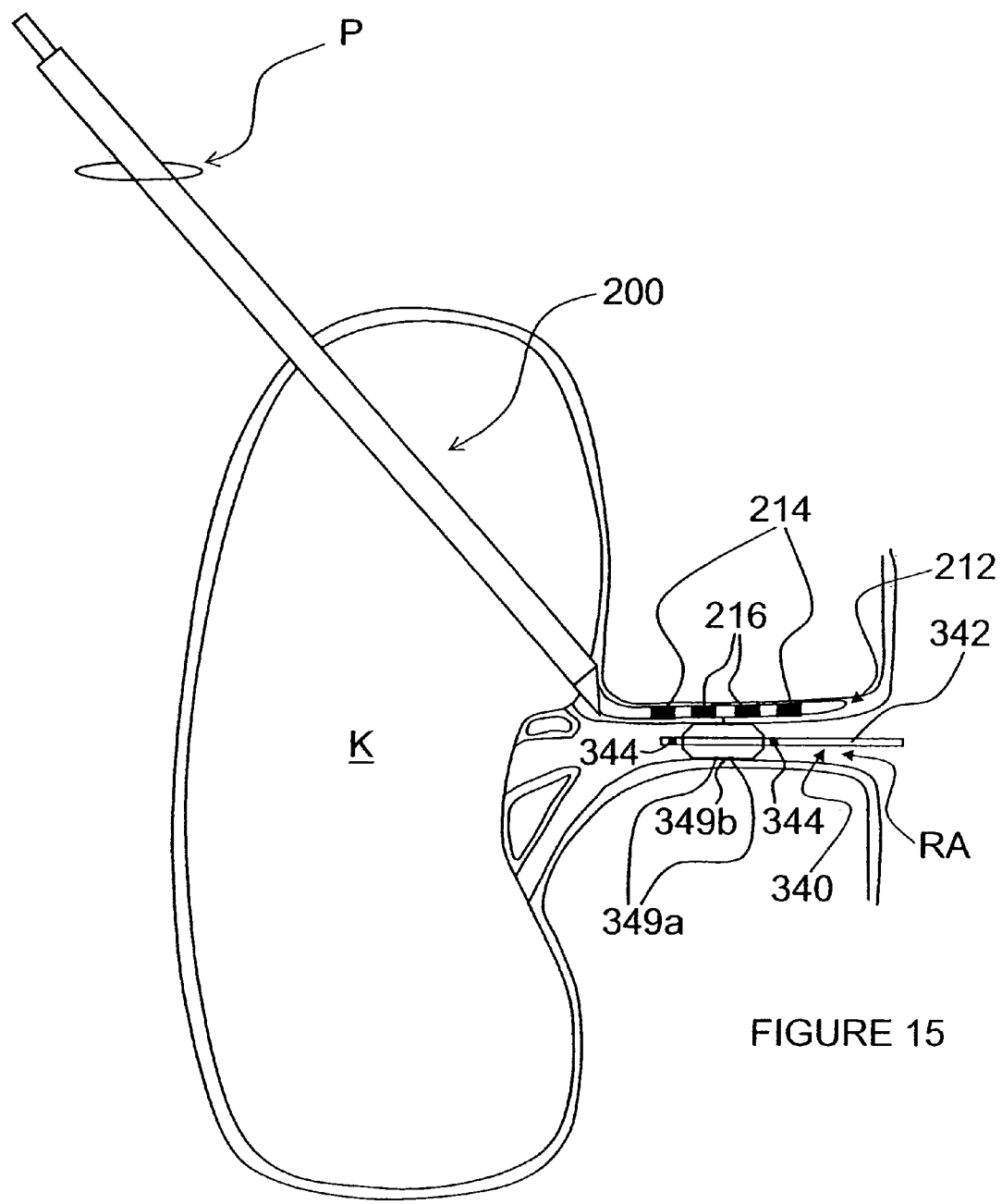
FIG. 15 is a side view, partially in section, of apparatus and a method for intravascular, extravascular and/or transvascular delivery, monitoring and control of PEF therapy.

Referring now to FIG. 15 in conjunction with FIGS. 13 and 14, combination intravascular, transvascular and extravascular apparatus for inducing, monitoring and controlling PEF therapy is described. In FIG. 15, apparatus 200 of FIG. 14 has been positioned extravascularly, while a variation of apparatus 340 of FIG. 13 is positioned intravascularly and transvascularly. In FIG. 15, non-target tissue monitoring electrodes 349a of catheter 342 contact, but do not penetrate, the vessel wall, while target tissue monitoring electrodes 349b are positioned transvascularly within the adventitia.

The apparatus of FIG. 15 facilitates monitoring of both intravascular and extravascular non-target tissue, as well as adventitially-disposed target tissue. Specifically, monitoring electrodes 216 are positioned for monitoring of the external wall of the vessel, while monitoring electrodes 349a are positioned for monitoring of the internal wall of the vessel. Furthermore, monitoring electrodes 349b are transvascularly positioned for monitoring of target neural tissue within the adventitia. PEF therapy may be delivered intravascularly via PEF-delivery electrodes 344, extravascularly via bipolar electrodes 214, or a combination thereof.

Although FIG. 15 illustratively comprises combination apparatus having intravascular, extravascular and transvascular components, it should be understood that any desired subset of intra-, extra- and transvascular components may be utilized, as desired. Furthermore, although the transvascular components of the apparatus of FIG. 15 illustratively originate intravascularly, it should be understood that the components alternatively may originate extravascularly. Further still, although the apparatus of FIG. 15 illustratively is configured to deliver PEF therapy both intravascularly and extravascularly, it should be understood that the apparatus alternatively may be configured for delivering the therapy solely intravascularly or solely extravascularly. PEF therapy also may be delivered transvascularly. Additionally, PEF therapy may be delivered from within one vessel in the renal vasculature and monitored from within a different vessel in the renal vasculature. For example, PEF therapy may be delivered from electrodes positioned within or across a renal artery and monitored via electrodes positioned within or across a renal vein.

Figure 16:
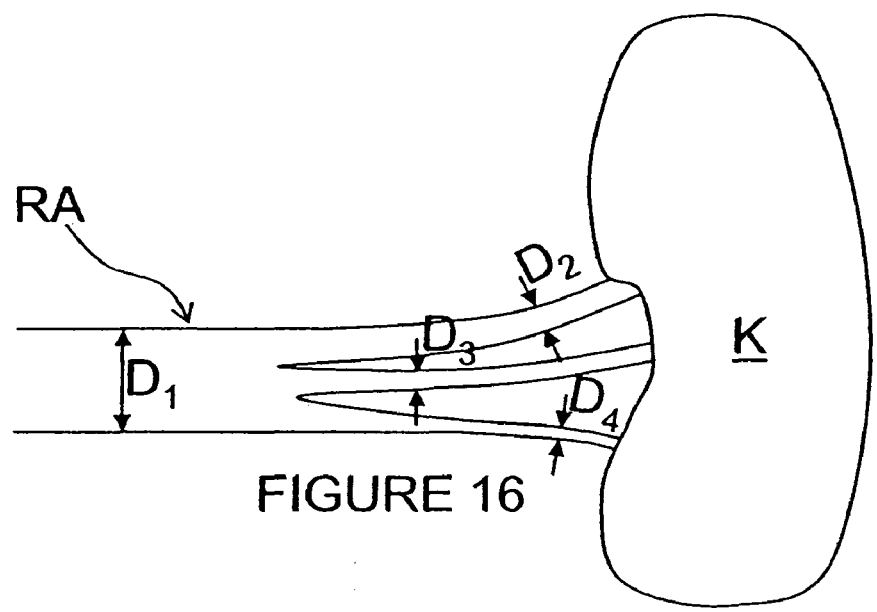
FIG. 16 is a side view, partially in section, of a patient's renal vasculature, illustrating geometric variation along the vasculature.
Figure 17:
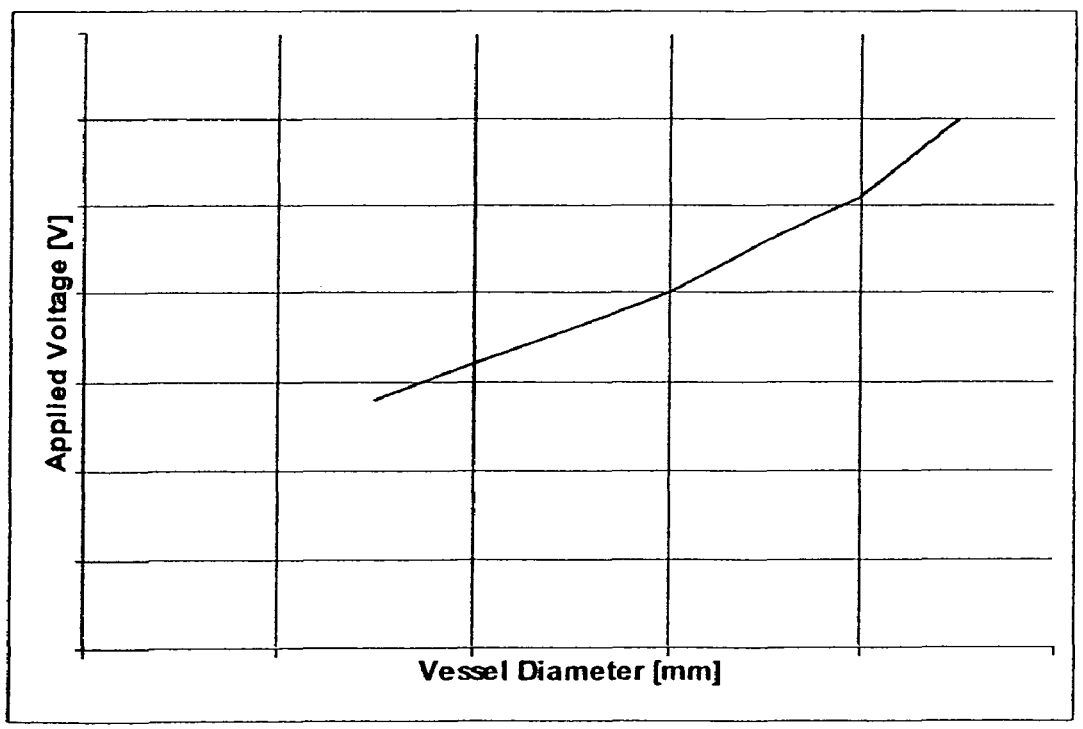
FIG. 17 is a schematic graph illustrating an upward-sloping relationship between required applied voltage and vessel diameter for a desired field strength in target neural fibers that contribute to renal function.

With reference now to FIGS. 16 and 17, an upward-sloping relationship between vessel diameter and required applied voltage necessary to achieve a desired field strength in target neural fibers that contribute to renal function from an intravascularly-delivered PEF therapy is described in order to apply a relatively consistent field strength to neural fibers that contribute to renal function, it may be necessary to apply a PEF with greater voltage in larger vessels. This upward-sloping relationship between voltage and vessel size allows for customization of the pulsed electric field based on the vessel size to be treated. Customization may be performed for each individual patient based on his or her specific vessel size, may be performed based on an average vessel size for a given location within renal vasculature, may be performed based on a combination of these factors or on other factors.

As seen in FIG. 16, the renal vasculature may have a variety of branches requiring treatment (for the purposes of illustration, the vasculature comprises three distal branches; however, any alternative number of branches may be present). The main branch of the renal artery RA generally has a diameter $D_1$ that is larger than the diameters $D_2$, $D_3$ and $D_4$ of the distal branches. In FIG. 16, $D_1 > D_2 > D_3 > D_4$, though the diameters may vary in a different manner, and/or a different number of branches may be present. The PEF system or the medical practitioner may determine these vessel sizes and modify the PEF therapy, as appropriate. Thus, when treating the patient of FIG. 16, voltage would be increased in the main branch of the renal artery having diameter $D_1$ and sequentially lowered in the distal branches having diameters $D_2$, $D_3$ and $D_4$.

For a known separation distance between the PEF-delivery electrodes, FIG. 17 schematically illustrates the upward-sloping relationship between internally-applied voltage and vessel diameter for a given expected field strength [V/cm] near the adventitia of the vessel. Once a desired adventitial field strength is selected and the vessel diameter is determined, the necessary applied voltage may be determined for the given electrode spacing. Optionally, a three-dimensional graph may be utilized that plots field strength, applied voltage and vessel diameter against one another. PEF-delivery electrode separation distance also may be plotted or examined against any or all of field strength, applied voltage and vessel diameter.

As an example, modeling indicates that, for a pair of bipolar PEF-delivery electrodes spaced 5 mm apart and centered within the vessel, in order to achieve field strength of 180V/cm in the adventitia of a 6 mm vessel, an applied voltage of about 200V would be required, while the same field strength in a vessel 4 mm in diameter would require an applied voltage of about 160V. These values are provided only for the purposes of illustration and should in no way be construed as limiting.

Temporarily blocking blood flow between the intravascular PEF-delivery electrodes, e.g., via an inflatable balloon, may locally increase impedance relative to regular blood flow. This may preferentially direct PEF therapy delivered across the electrodes into or through the vessel wall. This, in turn, may reduce the voltage required to achieve a desired field strength in the adventitia in a vessel of a given diameter, relative to unimpeded blood flow.

Referring now to FIGS. 18-27, illustrative PEF waveforms or pulse trains for inducing desired electroporative effects are described, such as in vivo, irreversible electroporation of nerves innervating the kidney. The PEF waveforms preferably do not electroporate or irreversibly electroporate non-target surrounding tissue, such as renal vasculature, kidney tissues, adrenal glands, lymph nodes, etc. These waveforms also may be applied in other in vivo applications wherein target tissue is more susceptible to electroporation than surrounding tissue. The waveforms, may, for example, be delivered via any of the previously described intravascular, extravascular or transvascular techniques.

Figure 18:
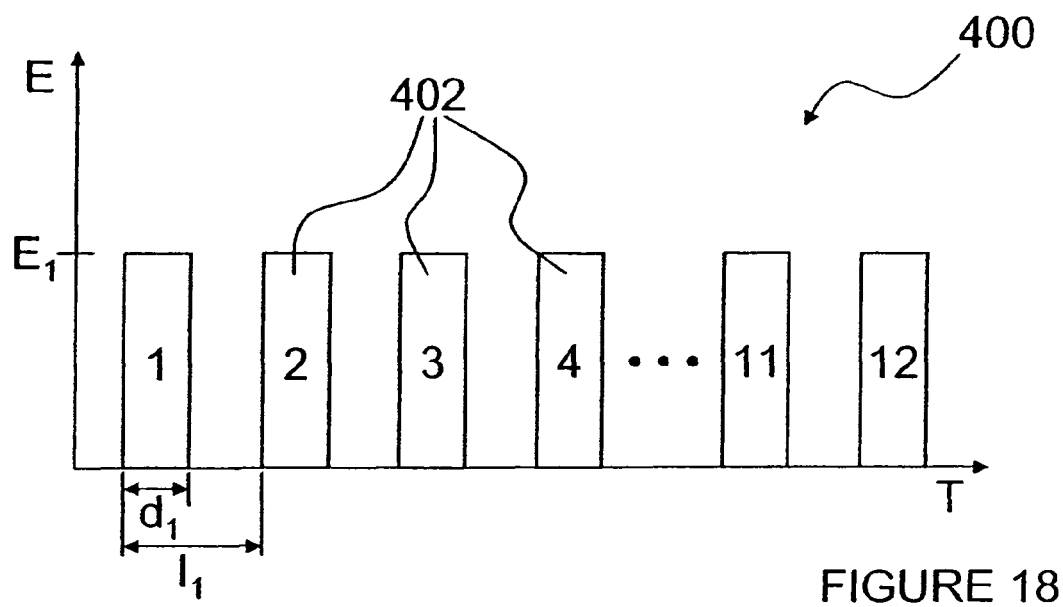
FIG. 18 is a schematic view of an illustrative PEF waveform comprising a pulse train with one or more pulses of constant amplitude (voltage) or field strength, duration, and interval.

PEF waveform 400 of FIG. 18 comprises a non-varying pulse train having one or more pulses 402 of equal voltage or equal field strength $E_1$, equal duration $d_1$ and equal interval $I_1$, delivered over time T. As an example, in one embodiment, waveform 400 might have a field strength of 150V/cm, a pulse duration of 2 ms, an interval of 1 second, and 12 pulses in total, though any other parameters may be provided. This waveform may be repeated or modified as desired, for example, in response to monitoring data collected during or after delivery of the waveform. The interval between delivery of individual pulses and/or between delivery of subsequent waveforms may be used to deliver a low voltage signal across monitoring electrodes for monitoring the effects of the PEF therapy, e.g., to measure impedance or conductivity of target or non-target tissue using, for example, the same or different electrodes than were used for PEF therapy delivery. It should be understood that such time gating of monitoring may be utilized with any of the waveforms described hereinafter.

In vitro experimentation has shown that altering various aspects of a PEF waveform can improve cell viability or survival. However, for the purposes of the present invention, it may be desirable to cause irreversible electroporation and cell death in target tissue. Thus, opposite alterations to those known to protect cells may be applied.

Figure 19:
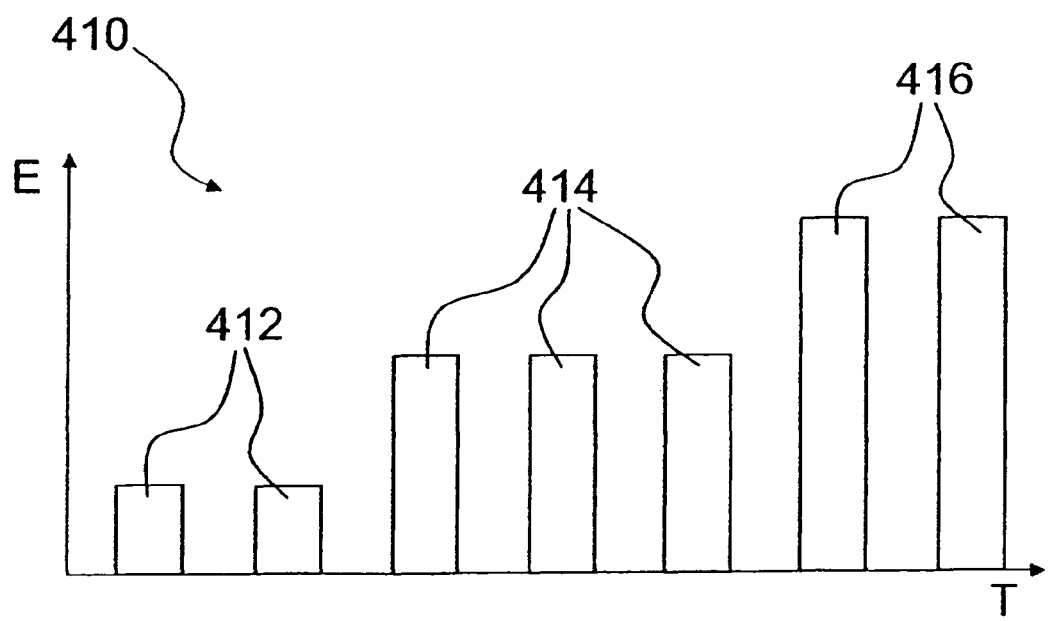
FIG. 19 is a schematic view of another illustrative PEF waveform comprising a pulse train with pulses of increasing field strength or amplitude.

Waveform 410 of FIG. 19 alters the field strength E [V/cm] in a manner that might increase irreversible electroporation. Waveform 410 begins with one or more relatively lower field strength pulses 412, followed by one or more relatively higher field strength pulses 414. Still higher field strength pulses 416 may be applied, etc. Lower field strength pulses 412 may be used to initiate electroporation in target neural tissue with little or no electroporation in non-target surrounding tissues. Once the electroporative effect is initiated in the target tissue, higher field strength pulses 414 and/or 416 expand or increase the number of pores in the target tissue, resulting in cell death. Furthermore, waveforms such as waveform 410 that begin with relatively smaller amplitude (i.e., voltage or field strength) might reduce a sensation of pain felt by the patient and/or may reduce muscle spasm.

Figure 20:
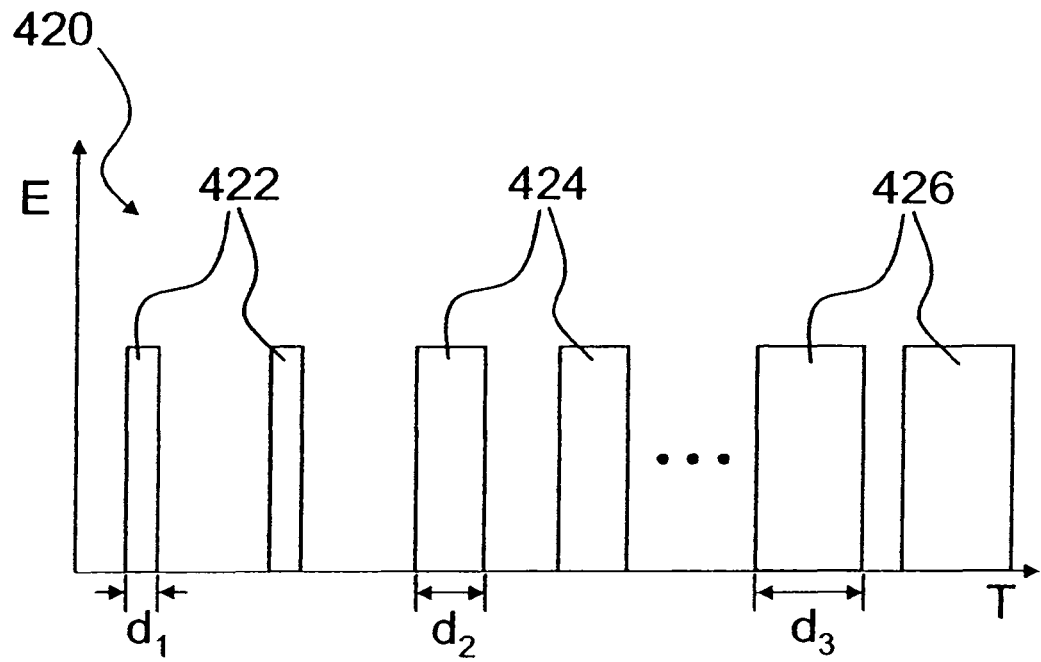
FIG. 20 is a schematic view of yet another illustrative PEF waveform comprising a pulse train with pulses of increasing duration.

In FIG. 20, the pulse duration d of waveform 420 is ramped up or increased to enhance irreversible electroporation of the target tissue. Waveform 420 begins with one or more pulses 422 of relatively shorter duration $d_1$, followed by one or more pulses 424 of relatively longer duration $d_2$. The shorter duration pulses 422 may initiate electroporation in the target tissue with little or no electroporation in non-target surrounding tissues. The longer duration pulses 424 expand or increase the number of pores in the target tissue resulting in cell death. As will be apparent, still longer duration pulses, such as pulses 426 of duration $d_3$, may be provided as desired.

Figure 21:
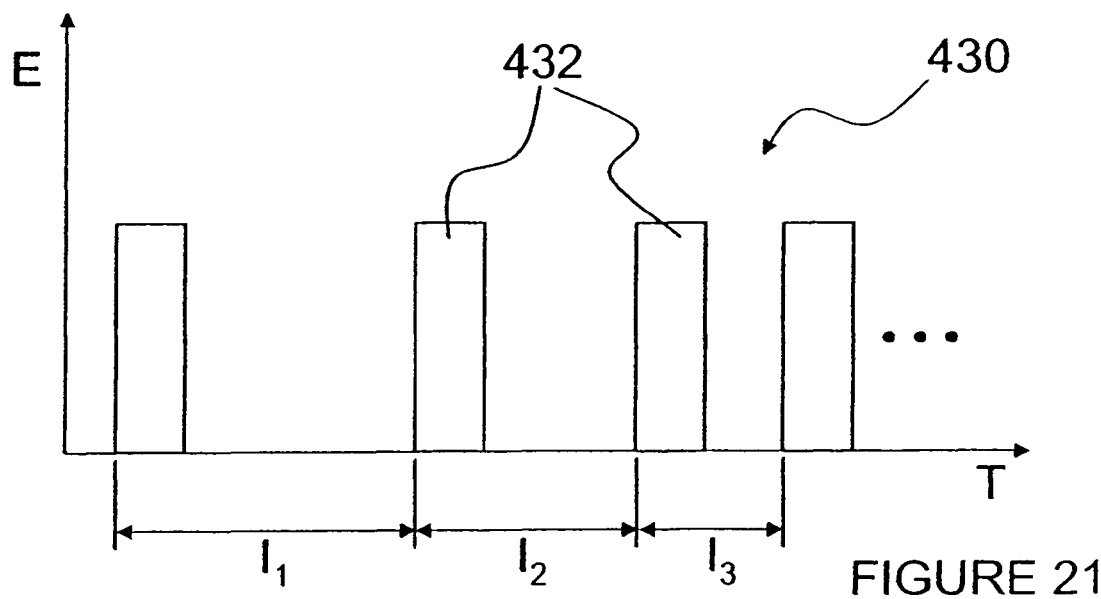
FIG. 21 is a schematic view of an illustrative PEF waveform comprising a pulse train with pulses of decreasing interval.

In FIG. 21, the time interval between pulses of waveform 430 is progressively decreased to enhance irreversible electroporation of the target tissue. Waveform 430 begins with interval $I_1$ between pulses 432. The interval is decreased to $I_2$, $I_3$, etc. It is known that electroporative pores close over time. By decreasing the time between each pulse, pores might expand or increase in number at a higher rate, potentially inducing irreversible electroporation with fewer total pulses.

A preferred pulse train for performing irreversible electroporation may involve a combination of variations in pulse amplitude or field strength, duration, and/or interval, as well as other parameters. In some embodiments, it may be desirable to alter multiple parameters within a single pulse to irreversibly electroporate target tissue while preferentially maintaining the viability of non-target tissue. Parameter variation optionally may be conducted manually or automatically in response to impedance or conductivity monitoring data obtained in the vicinity of the treatment site.

Figure 22:
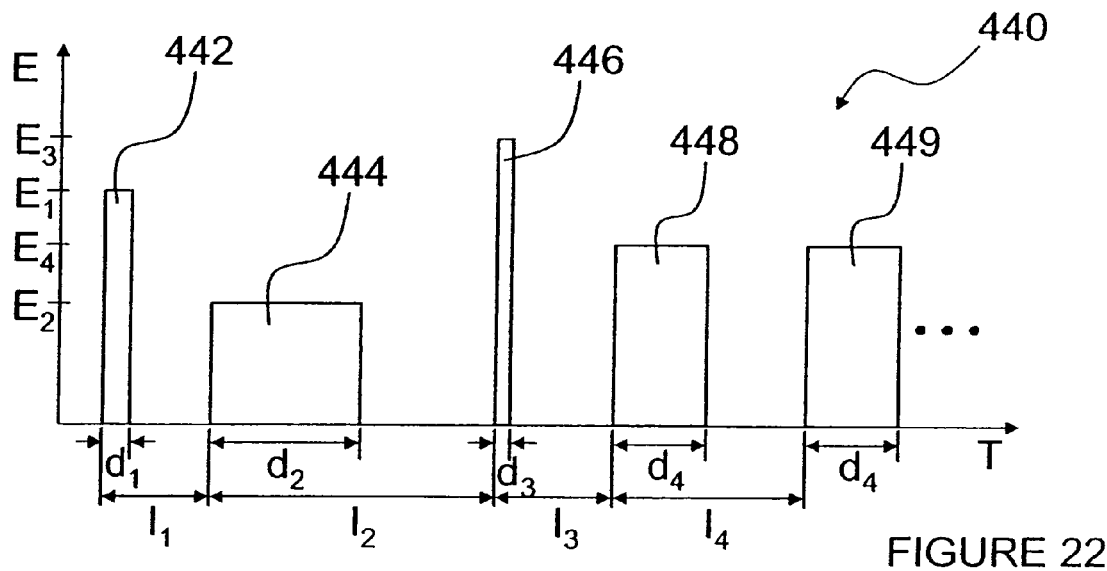
FIG. 22 is a schematic view of an illustrative PEF waveform comprising a pulse train of varying amplitude or field strength, duration, and/or interval.

Waveform 440 of FIG. 22 provides an example of a waveform comprising variation along multiple parameters. Pulse 442 has field strength $E_1$, duration $d_1$ and interval $I_1$. Pulse 442 initiates pore formation in target tissue, such as renal nerves. Preferably, little, no or reduced electroporation is initiated in non-target tissue. Interval $I_1$ may be of a duration sufficient to preclude excessive heating of target or non-target tissue.

Pulse 444 of field strength $E_2$, duration $d_2$ and interval $I_2$, may be used to expand pores initiated by pulse 442. Although field strength $E_2$ is lower than field strength $E_1$, the longer duration $d_2$ may increase the total pore area and/or may generate heat in the target tissue, which may enhance the electroporative effect. Interval $I_2$ may be long enough to dissipate heat generated by pulse 444, or it may be short enough that some elevation in temperature persists upon application of pulse 446.

Pulse 446 of field strength $E_3$, which is larger than field strength $E_2$, may further increase pore area. The relatively shorter pulse duration $d_3$ may reduce heat generation as compared to pulse 444, and thus may require a relatively shorter interval $I_3$ to dissipate generated heat. Optional pulses 448 and 449 of reduced field strength $E_4$, increased duration $d_4$ and increased interval $I_4$ relative to pulse 446 may further expand pores in target tissue, if needed, to achieve irreversible electroporation.

Additional or fewer pulses may be used, as needed. Furthermore, the parameters of the pulses may be varied, as needed. Variations in the number and/or form of the pulses of which waveform 440 is comprised may, for example, be determined in response to monitoring data collected in the vicinity of the treatment site.

Figure 23:
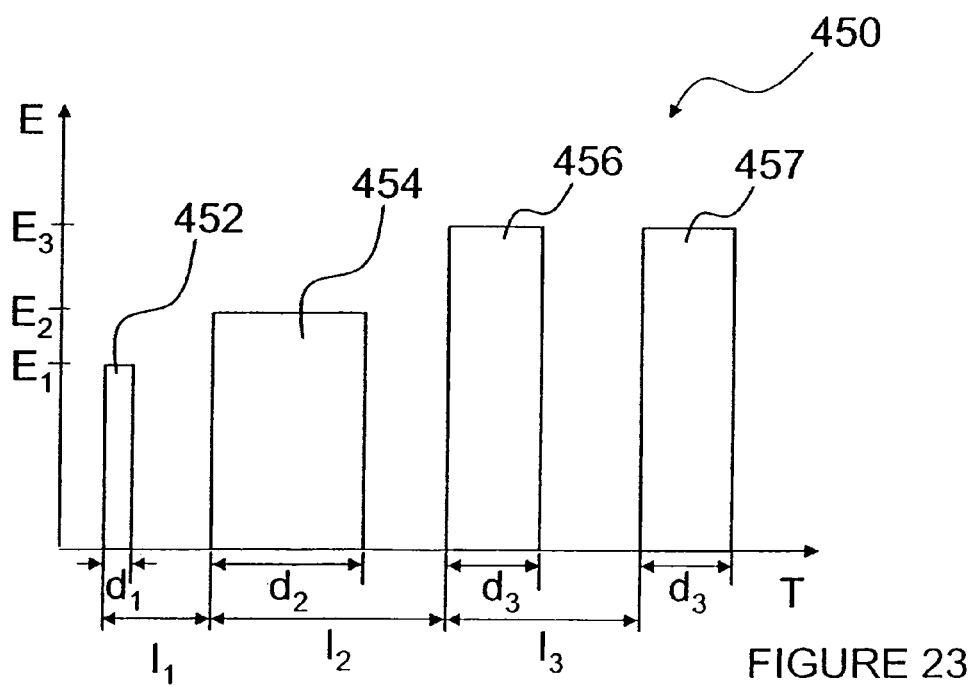
FIG. 23 is a schematic view of an illustrative PEF waveform comprising a pulse train of increasing field strength and varying pulse duration and interval.

With reference to FIG. 23, waveform 450 provides another example of a waveform comprising variation along multiple parameters. Pulse 452 comprises field strength $E_1$, duration $d_1$ and interval $I_1$. The pulse initiates electroporation in target tissue. The pulse interval is sufficient to preclude excessive heat generation in non-target tissue.

Pulse 454 is of larger field strength $E_2$ and longer pulse duration $d_2$ to increase pore surface area in target cell membranes. Interval $I_2$ may or may not equal interval $I_1$. Pulses 456 and 457, which irreversibly electroporate target tissue, are of larger field strength $E_3$ and of shorter pulse duration $d_3$ than the field strength and pulse duration of pulse 454.

The pulses of waveform 450 may induce electroporation in non-target tissue. However, if electroporation is induced in such non-target tissue, the pulse train preferable induces only reversible electroporation in the non-target tissue. Various protective measures may be employed to further protect or repair non-target tissues.

Figure 24:
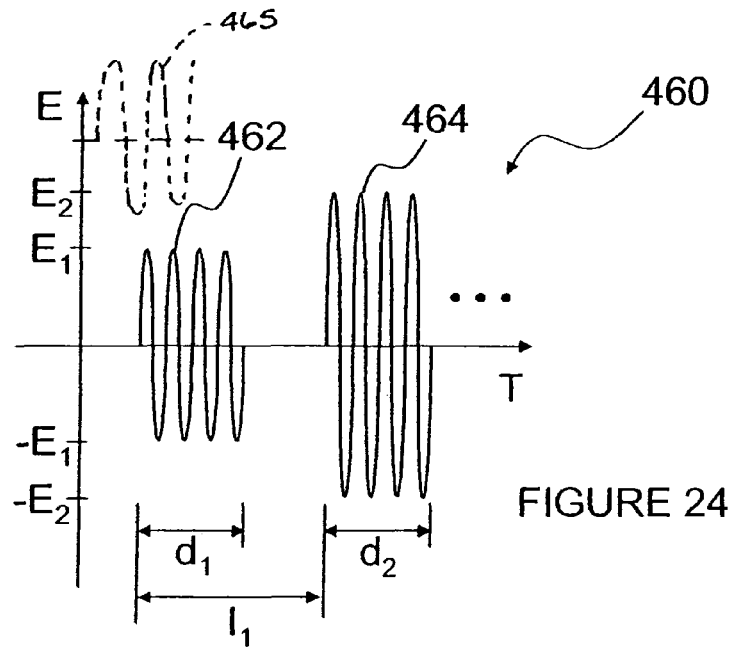
FIG. 24 is a schematic view of an illustrative PEF waveform comprising an AC pulse train of increasing amplitude.

Referring now to FIG. 24, pulsed alternating current waveform 460 also may be utilized. The same alterations to pulse and pulse train parameters may be employed as in the previous DC embodiments to achieve a desired effect, such as alteration of pulse (peak) amplitude or field strength, duration, and/or interval. Additionally, pulse frequency may be altered in an AC waveform. Waveform 460 illustratively comprises AC pulse 462 of lower peak field strength magnitude $E_1$ than the peak field strength magnitude $E_2$ of AC pulse 464. This may also potentially be accomplished by DC-shifted AC waveforms as shown by waveform 465 (broken line) in FIG. 24.

Figure 25A:
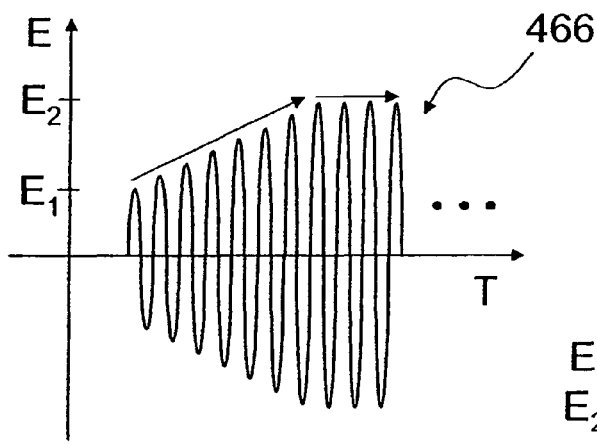
FIGS. 25A and 25B are schematic views of individual AC pulses of illustrative PEF waveforms.
Figure 25B:
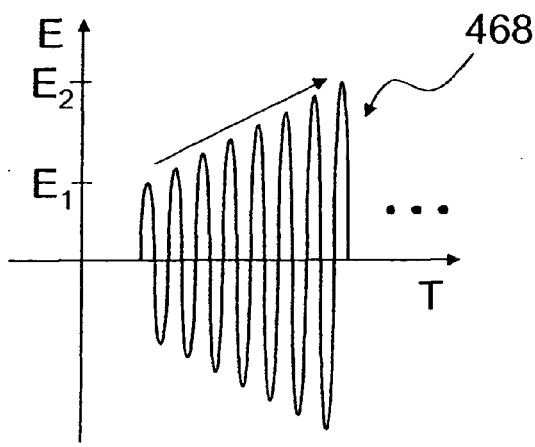

In addition to alteration between pulses, parameter alteration also may be provided within a pulse. In FIG. 25A, pulse 466 comprises a ramp in peak field strength magnitude from initial peak field strength magnitude $E_1$, followed by a period of constant peak field strength magnitude $E_2$. Alternative pulse 468 of FIG. 25B comprises a continuous ramp in peak field strength magnitude from an initial magnitude $E_1$ to a final magnitude $E_2$.

Figure 26:
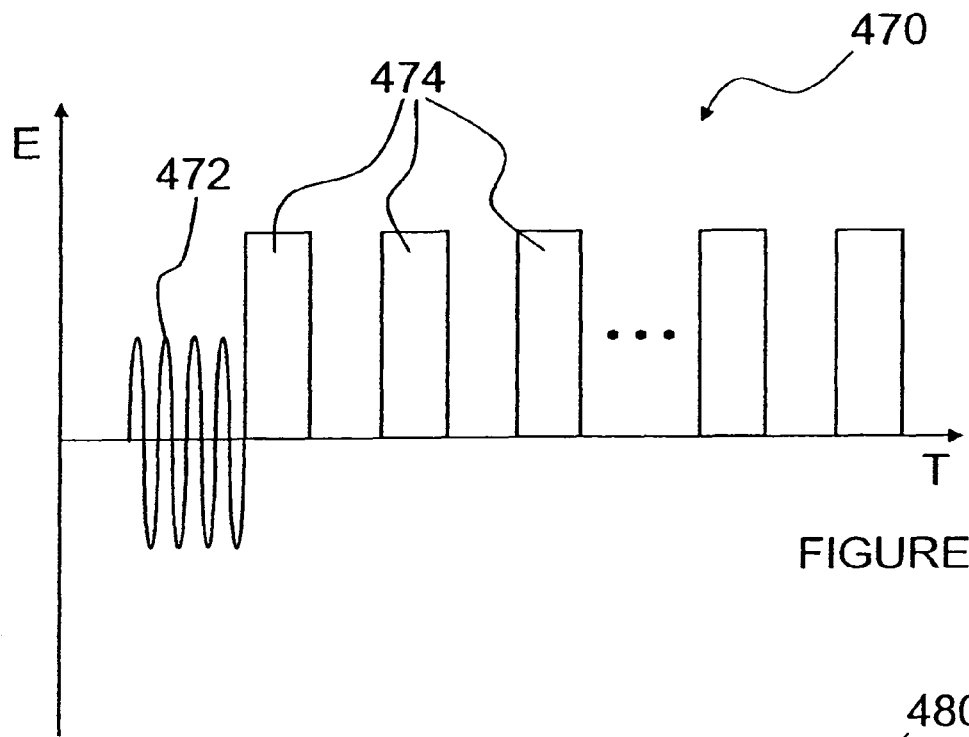
FIG. 26 is a schematic view of an illustrative PEF waveform comprising a composite AC and DC pulse train.
Figure 27:
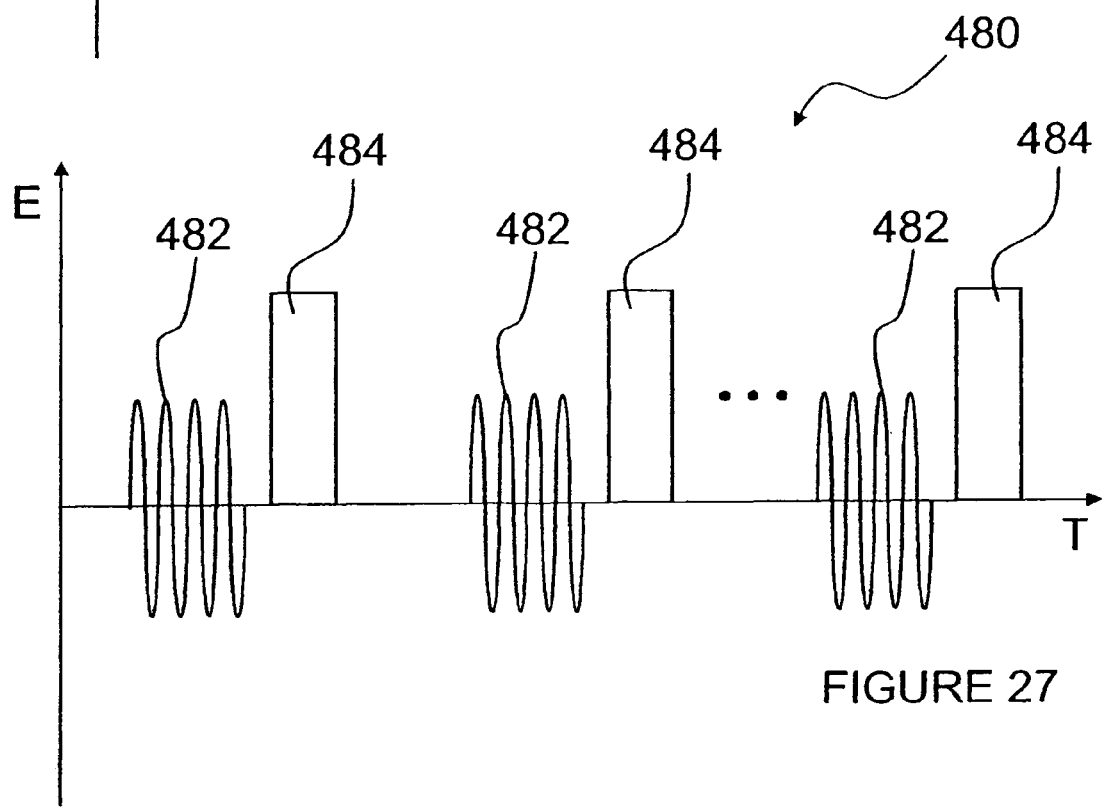
FIG. 27 is a schematic view of an alternative composite AC and DC pulse train.

With reference to FIG. 26, it has been observed in animal studies that application of DC pulses can cause a muscular response wherein vessel spasm and skeletal muscle contraction can occur. It has also been observed that application of a 500 kHz radiofrequency alternating current substantially reduces vessel spasm and muscle contraction. It is expected that alternative AC frequencies would have a similar effect, and 500 kHz should in no way be construed as limiting.

While it may be desirable to use an RF current to reduce or eliminate spasm and muscle contraction, the literature suggests that AC waveforms provide less cell-size specificity. In the case of in vivo electroporation, cell-size specificity may be of significant utility when target cells are larger than non-target cells. FIG. 26 provides a combination AC and DC waveform that is expected to provide both cell-size specificity and reduction in spasm or muscle contraction. Waveform 470 comprises initial AC pulse 472 followed by a series of DC pulses 474. The initial AC pulse may attenuate or abolish adverse muscular responses, while the DC pulses may achieve desired cell-size selectivity.

The peak field strength and/or the duration of the AC pulse may be less than, equal to, or greater than the field strength and/or duration, respectively, of the DC pulses. Furthermore, the parameters of the DC pulses may vary. Preferably, the interval between the AC pulse and the DC pulses is relatively short or is non-existent, such that muscular tissue cannot recover prior to initiation of the DC pulses. Optionally, multiple AC pulses may be provided in combination with one or more DC pulses. Waveform 480 of FIG. 27 comprises multiple AC pulses 482 in combination with multiple DC pulses 484.

Any of the embodiments of the present invention described herein optionally may be configured for infusion of agents into the treatment area before, during or after energy application, for example, to create a working space to facilitate electrode placement, to enhance or modify the neurodestructive or neuromodulatory effect of applied energy, to protect or temporarily displace non-target cells, and/or to facilitate visualization. Additional applications for infused agents will be apparent. If desired, uptake of infused agents by cells may be enhanced via initiation of reversible electroporation in the cells in the presence of the infused agents. The infusate may comprise, for example, fluids (e.g., heated or chilled fluids), air, $CO_2$, saline, heparin or heparinized saline, hypertonic saline, contrast agents, gels, conductive materials, space-occupying materials (gas, solid or liquid), protective agents, such as Poloxamer-188, anti-proliferative agents, Sirolimus, or other drugs and/or drug delivery elements. Variations of the present invention additionally or alternatively may be configured for aspiration. Agent infusion or aspiration may be performed in response to monitoring data obtained in the vicinity of the treatment site.

Although preferred illustrative variations of the present invention are described above, it will be apparent to those skilled in the art that various changes and modifications may be made thereto without departing from the invention. For example, although the variations primarily have been described for use in combination with pulsed electric fields, it should be understood that any other electric field may be delivered as desired. It is intended in the appended claims to cover all such changes and modifications that fall within the true spirit and scope of the invention.

We claim:

1. An apparatus for generating a pulsed electric field waveform for inducing controlled renal neuromodulation, the apparatus comprising:
   a pulse generator; and
   a controller including a medium containing instructions that cause the pulse generator to generate a first electric pulse at a first energy insufficient to induce irreversible electroporation and/or electrofusion, and a second electric pulse at a second energy sufficient to induce irreversible electroporation and/or electrofusion in a neural fiber that contributes to renal function of a patient, wherein the apparatus is configured to deliver the electric pulses generated by the pulse generator from within vasculature of the patient, and wherein the electric pulse energies are determined based at least in part on a diameter of the vasculature in which the electric pulses are delivered.

2. The apparatus of claim 1, wherein the second energy is greater than the first energy.

3. The apparatus of claim 1, wherein the instructions cause the generator to deliver the first electric pulse before delivering the second electric pulse.

4. The apparatus of claim 1, wherein the determined electric pulse energies are increased with increasing vessel diameter.

5. The apparatus of claim 1, wherein the first electric pulse comprises a first pulse duration and the second electric pulse comprises a second pulse duration, and wherein the first pulse duration is different than the second pulse duration.

6. The apparatus of claim 1, wherein the instructions cause the pulse generator to generate at least one additional electric pulse.

7. The apparatus of claim 6, wherein the additional electric pulse is of equal or greater energy than the second energy of the second electric pulse.

8. The apparatus of claim 6, wherein the instructions cause the pulse generator to generate the first, second and additional pulses in direct succession, and wherein the instructions cause the pulse generator to insert a time interval between delivery of the first pulse and the second pulse that is different than a time interval between delivery of the second pulse and the additional pulse.

9. The apparatus of claim 1, wherein the instructions cause the pulse generator to generate a plurality of electric pulses, the plurality including the first and second electric pulses, each electric pulse of the plurality of electric pulses comprising:
a pulse amplitude
a pulse duration; and
a time interval between delivery of subsequent pulses.

10. The apparatus of claim 9, wherein the instructions cause the pulse generator to vary the pulse duration among electric pulses of the plurality of pulses.

11. The apparatus of claim 9, wherein the instructions cause the pulse generator to vary the time interval between deliveries of subsequent pulses among electric pulses of the plurality of pulses.

12. The apparatus of claim 9, wherein the instructions cause the pulse generator to vary the pulse amplitude among electric pulses of the plurality of pulses.

13. The apparatus of claim 9, wherein the plurality of electric pulses generated by the pulse generator comprises electric pulses chosen from the group consisting of DC electric pulses, AC electric pulses, exponentially-decaying electric pulses and combinations thereof.

14. An apparatus for generating a pulsed electric field waveform for inducing controlled renal neuromodulation, the apparatus comprising:
a pulse generator; and
a controller including a medium containing instructions that cause the pulse generator to generate a first electric pulse at a first energy insufficient to induce irreversible electroporation and/or electrofusion, and a second electric pulse at a second energy sufficient to induce irreversible electroporation and/or electrofusion in a neural fiber that contributes to renal function of a patient,
wherein the apparatus is configured to deliver the electric pulses generated by the pulse generator from within vasculature of the patient, and wherein the electric pulse energies are determined based at least in part on whether the apparatus temporarily has blocked blood flow within the vasculature.

15. The apparatus of claim 14, wherein the determined electric pulse energies are decreased when the apparatus temporarily has blocked blood flow within the vasculature.

16. A method for inducing controlled renal neuromodulation, the method comprising:
positioning at least one electrode within vasculature of the patient and proximate to a neural fiber that contributes to renal function of a patient, the neural fiber having a threshold beyond which electroporation is irreversible and/or electrofusion occurs;
delivering a pulsed electric field via the electrode to modulate the neural fiber, wherein the pulsed electric field comprises a first electric pulse with a first energy below the threshold, and a second electric pulse with a second energy above the threshold; and
determining the electric pulse energies based at least in part on a diameter of the vasculature in which the electrode is positioned.

17. The method of claim 16, wherein delivering the pulsed electric field further comprises delivering the first electric pulse before delivering the second electric pulse.

18. The method of claim 16, wherein determining the electric pulse energies further comprises increasing the electric pulse energies as vessel diameter increases.

19. The method of claim 16 further comprising temporarily blocking blood flow within the vasculature in a vicinity of the electrode.

20. The method of claim 19, wherein temporarily blocking blood flow further comprises reducing the electric pulse energies.

21. The method of claim 16 further comprising monitoring electroporation and/or electrofusion in tissue exposed to the pulsed electric field.

22. The method of claim 21 further comprising altering the pulsed electric field in response to monitoring data.

23. The method of claim 22, wherein altering the pulsed electric field further comprises varying at least one parameter of the pulsed electric field in response to the monitoring data.

24. The method of claim 16, wherein delivering the pulsed electric field further comprises orienting the pulsed electric field with a longitudinal dimension of the neural fiber that contributes to renal function.

25. The method of claim 16 further comprising providing the threshold.

26. An apparatus for generating a pulsed electric field waveform for inducing controlled renal neuromodulation, comprising:
a pulse generator; and
a controller including a medium containing instructions that cause the pulse generator to generate a pulsed electric field waveform having waveform parameters configured to induce irreversible electroporation and/or electrofusion in a neural fiber that contributes to renal function of a patient when the waveform is delivered within vasculature of the patient,
wherein at least one of the waveform parameters is determined based on a diameter of the vasculature in which the pulsed electric field waveform is delivered.

27. The apparatus of claim 26, wherein an energy of the pulsed electric field waveform is increased with increasing vessel diameter.

28. The apparatus of claim 26, wherein the instructions cause the pulse generator to vary at least one of the waveform parameters among electric pulses of the waveform.

29. The apparatus of claim 26, wherein the waveform parameters are chosen from the group consisting of energy, field strength, pulse amplitude, pulse shape, pulse duration, interval between subsequent pulses, and combinations thereof.

30. An apparatus for generating a pulsed electric field for controlling neuromodulation in a neural fiber that contributes to renal function of a patient, the neural fiber having a threshold beyond which electroporation is irreversible and/or electrofusion occurs, the apparatus comprising:

a pulsed field generator; and a control system operatively coupled to the pulsed field generator, the control system including a medium containing instructions that cause the pulsed field generator to generate a first pulse at an energy below the threshold and a second pulse at an energy above the threshold, wherein the apparatus is configured to deliver the pulses generated by the pulsed field generator from within vasculature of the patient, and wherein the pulse energies are determined based at least in part on a diameter of the vasculature in which the pulses are delivered.

* * * * *